US009213999B2

(12) United States Patent
Sakurada

(10) Patent No.: US 9,213,999 B2
(45) Date of Patent: *Dec. 15, 2015

(54) PROVIDING IPSCS TO A CUSTOMER

(75) Inventor: Kazuhiro Sakurada, Yokohama (JP)

(73) Assignee: KYOTO UNIVERSITY, Kyoto (JP)

( * ) Notice: Subject to any disclaimer, the term of this patent is extended or adjusted under 35 U.S.C. 154(b) by 4 days.

This patent is subject to a terminal disclaimer.

(21) Appl. No.: 12/484,152

(22) Filed: Jun. 12, 2009

(65) Prior Publication Data

US 2009/0299763 A1    Dec. 3, 2009

Related U.S. Application Data

(63) Continuation-in-part of application No. 12/157,697, filed on Jun. 13, 2008, now Pat. No. 8,211,697.

(60) Provisional application No. 61/040,646, filed on Mar. 28, 2008, provisional application No. 61/061,592, filed on Jun. 13, 2008, provisional application No. 61/061,594, filed on Jun. 13, 2008.

(30) Foreign Application Priority Data

| Jun. 15, 2007 | (JP) | ................................. 2007-159382 |
| Nov. 20, 2007 | (WO) | ................. PCT/EP2007/010019 |
| Jun. 13, 2008 | (WO) | ................. PCT/EP2008/005047 |
| Jun. 13, 2008 | (WO) | ................. PCT/IB2008/002540 |

(51) Int. Cl.
*G01N 33/48* (2006.01)
*C12N 15/00* (2006.01)
*G06Q 50/22* (2012.01)
*C12N 5/074* (2010.01)

(52) U.S. Cl.
CPC .............. *G06Q 50/22* (2013.01); *C12N 5/0696* (2013.01); *C12N 2501/155* (2013.01); *C12N 2501/602* (2013.01); *C12N 2501/603* (2013.01); *C12N 2501/604* (2013.01); *C12N 2501/605* (2013.01); *C12N 2501/606* (2013.01); *C12N 2501/608* (2013.01); *C12N 2502/45* (2013.01); *C12N 2506/00* (2013.01); *C12N 2510/00* (2013.01); *C12N 2799/027* (2013.01)

(58) Field of Classification Search
CPC ........... C12N 5/0696; C12N 2501/602; C12N 2501/603; C12N 2510/00; C12N 2501/604; C12N 2501/606; C12N 2501/605; C12N 2501/608; C12N 2501/155; C12N 2799/027; C12N 2502/45; C12N 2506/00
See application file for complete search history.

(56) References Cited

U.S. PATENT DOCUMENTS

| 4,650,764 A | 3/1987 | Temin et al. |
| 4,861,719 A | 8/1989 | Miller |
| 4,937,190 A | 6/1990 | Palmenberg et al. |
| 5,225,348 A | 7/1993 | Nagata et al. |
| 5,266,491 A | 11/1993 | Nagata et al. |
| 5,268,290 A | 12/1993 | Hasegawa et al. |
| 5,288,514 A | 2/1994 | Ellman |
| 5,324,645 A | 6/1994 | Takahara et al. |
| 5,449,614 A | 9/1995 | Danos et al. |
| 5,519,134 A | 5/1996 | Acevedo et al. |
| 5,525,735 A | 6/1996 | Gallop et al. |
| 5,549,974 A | 8/1996 | Holmes |
| 5,591,624 A | 1/1997 | Barber et al. |
| 5,637,456 A | 6/1997 | Roth et al. |
| 5,652,122 A | 7/1997 | Frankel et al. |
| 5,674,980 A | 10/1997 | Frankel |
| 5,707,618 A | 1/1998 | Armentano et al. |
| 5,716,832 A | 2/1998 | Barber et al. |
| 5,744,320 A | 4/1998 | Sherf et al. |
| 5,817,491 A | 10/1998 | Yee et al. |
| 5,830,725 A | 11/1998 | Nolan et al. |
| 5,834,256 A | 11/1998 | Finer et al. |
| 5,858,740 A | 1/1999 | Finer et al. |
| 5,910,434 A | 6/1999 | Rigg et al. |
| 5,955,331 A | 9/1999 | Danos et al. |
| 6,013,517 A | 1/2000 | Respess et al. |
| 6,017,735 A | 1/2000 | O'hare |
| 6,017,761 A | 1/2000 | Rigg et al. |
| 6,025,192 A | 2/2000 | Beach et al. |
| 6,140,111 A | 10/2000 | Riviere et al. |
| 6,146,874 A | 11/2000 | Zolotukhin et al. |
| 6,153,432 A | 11/2000 | Halvorsen et al. |
| 6,153,745 A | 11/2000 | Williams et al. |

(Continued)

FOREIGN PATENT DOCUMENTS

| AU | 2008201280 A1 | 4/2008 |
| CN | 101250502 A | 8/2008 |

(Continued)

OTHER PUBLICATIONS

Essentials of Stem Cell Biology, R. Lanza et al., eds., Elsevier Academic Press, Amsterdam, 2006, pp. 266-267.*
Miyamoto et al. Reprogramming Events of Mammalian Somatic Cells Induced by Xenopus Iaevis Egg Extracts. Molec. Reproduction Develop., 2007, vol. 74, pp. 1268-1277.*
Stadtfeld et al. Induced pluripotent stem cells generated without viral integration. Science, vol. 322. pp. 945-949.*
Okita et al. Generation of mouse induced pluripotent stem cells without viral vectors. Science. vol. 322, pp. 949-953.*
Gonzales et al. Generation of mouse-induced pluripotent stem cells by transient expression of a single nonviral polycistronic vector. PNAS, 2009, vol. 106, pp. 8918-8922.*
Yamanaka, S. Induction of pluripotent stem cells from mouse fibroblasts by four transcription factors. Cell Prolif. 2008, vol. 41, (Suppl. 1), 51-56.*

(Continued)

*Primary Examiner* — Deborah Crouch
(74) *Attorney, Agent, or Firm* — Knobbe, Martens, Olson & Bear, LLP

(57) ABSTRACT

The present disclosure features methods relating to conducting a stem cell technology business such as a regenerative medicine business based on induced pluripotent stem cells (iPSCs) and cells differentiated from iPSCs. The present disclosure also provides a database of iPSC-derived cells and methods of using the database for tracking customers and samples, as well as methods for marketing and running the business.

4 Claims, 4 Drawing Sheets

(56) References Cited

U.S. PATENT DOCUMENTS

| | | | |
|---|---|---|---|
| 6,203,975 B1 | 3/2001 | Wilson et al. | |
| 6,251,398 B1 | 6/2001 | O'Hare et al. | |
| 6,255,071 B1 | 7/2001 | Beach et al. | |
| 6,312,948 B1 | 11/2001 | Cohen-haguenauer | |
| 6,312,949 B1 | 11/2001 | Sakurada et al. | |
| 6,333,195 B1 | 12/2001 | Respess et al. | |
| 6,365,352 B1 | 4/2002 | Yerramilli et al. | |
| 6,395,546 B1 | 5/2002 | Zobel et al. | |
| 6,451,595 B1 | 9/2002 | Kim et al. | |
| 6,485,959 B1* | 11/2002 | Demetriou et al. | 435/243 |
| 6,521,453 B1 | 2/2003 | Crameri et al. | |
| 6,521,455 B2 | 2/2003 | O'Hare et al. | |
| 6,605,275 B1 | 8/2003 | Boyse et al. | |
| 6,660,514 B1 | 12/2003 | Zolotukhin et al. | |
| 6,773,920 B1 | 8/2004 | Dalby et al. | |
| 6,833,269 B2 | 12/2004 | Carpenter | |
| 6,841,535 B2 | 1/2005 | Divita et al. | |
| 6,872,528 B2 | 3/2005 | Klatzmann et al. | |
| 6,875,578 B2 | 4/2005 | Giuliano et al. | |
| 6,881,825 B1 | 4/2005 | Robbins et al. | |
| 6,910,434 B2 | 6/2005 | Lundgren et al. | |
| 6,995,009 B1 | 2/2006 | Kitamura et al. | |
| 7,029,913 B2 | 4/2006 | Thomson | |
| 7,030,292 B2 | 4/2006 | Yan et al. | |
| 7,070,994 B2 | 7/2006 | Barber et al. | |
| 7,250,255 B2 | 7/2007 | Yamanaka | |
| 7,439,064 B2 | 10/2008 | Thomson et al. | |
| 8,058,065 B2* | 11/2011 | Yamanaka et al. | 435/377 |
| 8,129,187 B2* | 3/2012 | Yamanaka et al. | 435/377 |
| 8,211,697 B2* | 7/2012 | Sakurada et al. | 435/377 |
| 8,278,104 B2* | 10/2012 | Yamanaka et al. | 435/377 |
| 2002/0090722 A1 | 7/2002 | Dominko et al. | |
| 2002/0174013 A1 | 11/2002 | Freeman et al. | |
| 2003/0003574 A1 | 1/2003 | Toma et al. | |
| 2003/0044976 A1 | 3/2003 | Dominko et al. | |
| 2003/0161817 A1 | 8/2003 | Young et al. | |
| 2004/0048297 A1 | 3/2004 | Scherf | |
| 2004/0091936 A1* | 5/2004 | West | 435/7.1 |
| 2004/0137460 A1 | 7/2004 | Yamanaka et al. | |
| 2005/0019801 A1 | 1/2005 | Rubin et al. | |
| 2005/0026133 A1 | 2/2005 | Nakatsuji et al. | |
| 2005/0042595 A1* | 2/2005 | Haas | 435/2 |
| 2005/0079606 A1 | 4/2005 | Tamaki et al. | |
| 2005/0130144 A1 | 6/2005 | Nakatsuji et al. | |
| 2005/0276792 A1* | 12/2005 | Kaminski et al. | 424/93.7 |
| 2006/0030041 A1 | 2/2006 | Furcht et al. | |
| 2006/0084172 A1 | 4/2006 | Muller et al. | |
| 2006/0088599 A1 | 4/2006 | Prasad et al. | |
| 2006/0095319 A1 | 5/2006 | Cardwell | |
| 2006/0110830 A1 | 5/2006 | Dominko et al. | |
| 2006/0292620 A1 | 12/2006 | Yamanaka et al. | |
| 2007/0033061 A1 | 2/2007 | Patten et al. | |
| 2007/0053884 A1 | 3/2007 | Suda et al. | |
| 2007/0155013 A1 | 7/2007 | Akaike et al. | |
| 2007/0202592 A1 | 8/2007 | Kitagawa et al. | |
| 2007/0254884 A1 | 11/2007 | Chen et al. | |
| 2007/0269790 A1 | 11/2007 | Amit et al. | |
| 2008/0003560 A1 | 1/2008 | Nakatsuji et al. | |
| 2008/0076176 A1 | 3/2008 | Dominko et al. | |
| 2008/0085555 A1 | 4/2008 | Asahara et al. | |
| 2008/0132803 A1 | 6/2008 | Friedlander | |
| 2008/0171358 A1 | 7/2008 | Perrault | |
| 2008/0171385 A1 | 7/2008 | Bergendahl et al. | |
| 2008/0206865 A1 | 8/2008 | Zhang et al. | |
| 2008/0233610 A1 | 9/2008 | Thomson et al. | |
| 2008/0274914 A1 | 11/2008 | Yamanaka et al. | |
| 2008/0280362 A1 | 11/2008 | Jaenisch et al. | |
| 2008/0293143 A1 | 11/2008 | Lin et al. | |
| 2008/0299548 A1 | 12/2008 | Yamanaka | |
| 2009/0047263 A1 | 2/2009 | Yamanaka et al. | |
| 2009/0068742 A1 | 3/2009 | Yamanaka | |
| 2009/0191159 A1 | 7/2009 | Sakurada et al. | |
| 2009/0191171 A1 | 7/2009 | Ma | |
| 2009/0227032 A1 | 9/2009 | Yamanaka | |
| 2009/0246875 A1 | 10/2009 | Yamanaka et al. | |
| 2009/0299763 A1 | 12/2009 | Sakurada | |
| 2009/0304646 A1 | 12/2009 | Sakurada et al. | |
| 2009/0324559 A1 | 12/2009 | Sakurada et al. | |
| 2010/0003757 A1 | 1/2010 | Mack | |
| 2010/0021437 A1 | 1/2010 | Isacson | |
| 2010/0062533 A1 | 3/2010 | Yamanaka | |
| 2010/0062534 A1 | 3/2010 | Hochedlinger | |
| 2010/0075421 A1 | 3/2010 | Yamanaka | |
| 2010/0093090 A1 | 4/2010 | Deng | |
| 2010/0105100 A1 | 4/2010 | Sakurada et al. | |
| 2010/0120069 A1 | 5/2010 | Sakurada et al. | |
| 2010/0144031 A1 | 6/2010 | Jaenisch | |
| 2010/0184051 A1 | 7/2010 | Hochedlinger | |
| 2010/0184227 A1 | 7/2010 | Thomson | |
| 2010/0210014 A1 | 8/2010 | Yamanaka | |
| 2010/0216236 A1 | 8/2010 | Yamanaka | |
| 2010/0221827 A1 | 9/2010 | Jaenisch | |
| 2010/0233804 A1 | 9/2010 | Zhou | |
| 2010/0240090 A1 | 9/2010 | Sakurada et al. | |
| 2010/0267135 A1 | 10/2010 | Sakurada et al. | |
| 2010/0279404 A1 | 11/2010 | Yamanaka | |
| 2011/0039332 A1 | 2/2011 | Sakurada et al. | |

FOREIGN PATENT DOCUMENTS

| | | |
|---|---|---|
| CN | 101550428 A | 10/2009 |
| EP | 1384775 | 1/2004 |
| EP | 1403366 A1 | 3/2004 |
| EP | 1970446 A1 | 9/2008 |
| EP | 2096169 A1 | 9/2009 |
| JP | 2-227075 | 9/1990 |
| JP | 2002-065261 | 3/2002 |
| JP | 2003-009854 | 1/2003 |
| JP | 2004-161682 A | 6/2004 |
| JP | 2005-095027 | 4/2005 |
| JP | 2005-359537 | 12/2005 |
| JP | 2008-283972 | 11/2008 |
| WO | WO 95/10619 A2 | 4/1995 |
| WO | WO 95/10619 A3 | 7/1995 |
| WO | WO 97/05265 A1 | 2/1997 |
| WO | WO 00/18885 A1 | 4/2000 |
| WO | WO 00/23567 A2 | 4/2000 |
| WO | WO 00/27995 A1 | 5/2000 |
| WO | WO 00/23567 A3 | 7/2000 |
| WO | WO 01/21767 A2 | 3/2001 |
| WO | WO 01/34776 A1 | 5/2001 |
| WO | WO 01/51616 A2 | 7/2001 |
| WO | WO 01/21767 A3 | 8/2001 |
| WO | WO 01/81549 A2 | 11/2001 |
| WO | WO 00/73423 A1 | 12/2001 |
| WO | WO 02/00871 A2 | 1/2002 |
| WO | WO 02/061033 A2 | 8/2002 |
| WO | WO 02/000871 A3 | 10/2002 |
| WO | WO 02/086129 A1 | 10/2002 |
| WO | WO 02/086134 A2 | 10/2002 |
| WO | WO 02/097090 A1 | 12/2002 |
| WO | WO 03/018780 A1 | 3/2003 |
| WO | WO 02/086134 A3 | 12/2003 |
| WO | WO 2004/081205 A1 | 9/2004 |
| WO | WO 2005/080598 A1 | 9/2005 |
| WO | WO 2005/090557 A1 | 9/2005 |
| WO | WO 2006/035741 A1 | 4/2006 |
| WO | WO 2006/084229 A2 | 8/2006 |
| WO | WO 2006/088867 A2 | 8/2006 |
| WO | WO 2007/026255 A2 | 3/2007 |
| WO | WO 2007/054720 A1 | 5/2007 |
| WO | WO 2007/069666 A1 | 6/2007 |
| WO | WO 2007/097494 A1 | 8/2007 |
| WO | WO 2008/030610 A2 | 3/2008 |
| WO | WO 2008/035110 A1 | 3/2008 |
| WO | WO 2008/038148 A2 | 4/2008 |
| WO | WO 2008/089351 A1 | 7/2008 |
| WO | WO 2008/105566 A1 | 9/2008 |
| WO | WO 2008/105630 A1 | 9/2008 |
| WO | WO 2008/116213 A1 | 9/2008 |
| WO | WO 2008/118820 A2 | 10/2008 |
| WO | WO 2008/124133 A1 | 10/2008 |
| WO | WO 2008/118820 A3 | 11/2008 |
| WO | WO 2008/150814 A2 | 12/2008 |

(56) References Cited

FOREIGN PATENT DOCUMENTS

| | | |
|---|---|---|
| WO | WO 2008/151058 A2 | 12/2008 |
| WO | WO 2008/151058 A3 | 1/2009 |
| WO | WO 2009/006930 A1 | 1/2009 |
| WO | WO 2009/006997 A1 | 1/2009 |
| WO | WO 2009/007852 A2 | 1/2009 |
| WO | WO 2008/150814 A3 | 2/2009 |
| WO | WO 2009/023161 A1 | 2/2009 |
| WO | WO 2009/032194 A1 | 3/2009 |
| WO | WO 2009/032456 A2 | 3/2009 |
| WO | WO 2009/032456 A3 | 4/2009 |
| WO | WO 2009/057831 A1 | 5/2009 |
| WO | WO 2009/061442 A1 | 5/2009 |
| WO | WO 2009/067563 A1 | 5/2009 |
| WO | WO 2009/007852 A3 | 8/2009 |
| WO | WO 2009/096614 A1 | 8/2009 |
| WO | WO 2009/102983 A2 | 8/2009 |
| WO | WO 2009/115295 A1 | 9/2009 |
| WO | WO 2009/133971 A1 | 11/2009 |
| WO | WO 2009/102983 A3 | 12/2009 |
| WO | WO 2009/144008 A1 | 12/2009 |
| WO | WO 2009/149233 A1 | 12/2009 |
| WO | WO 2010/013359 A1 | 2/2010 |
| WO | WO 2010/048567 A1 | 4/2010 |

OTHER PUBLICATIONS

Dimos, et al. Induced pluripotent stem cells generated from patients with ALS can be differentiated into motor neurons. Science. Aug. 29, 2008;321(5893):1218-21.

Hockemeyer, et al. A drug-inducible system for direct reprogramming of human somatic cells to pluripotency. Cell Stem Cell. Sep. 11, 2008;3(3):346-53.

Maherali, et al. A high-efficiency system for the generation and study of human induced pluripotent stem cells. Cell Stem Cell. Sep. 11, 2008;3(3):340-5.

Park, et al. Disease-specific induced pluripotent stem cells. Cell. Sep. 5, 2008;134(5):877-86.

A reprogramming rush. Editorial. Nature. Mar. 27, 2008. 452:388. Published online Mar. 26, 2008.

Adachi et al. Role of SOX2 in maintaining pluripotency of human embryonic stem cells. Genes Cells. May 2010; 15(5):455-70.

Adewumi et al., Characterization of Human Embryonic Stem Cell Lines by the International Stem Cell Initiative, Nat. Biotechnol. 25(7):803-16, 2007.

Adhikary et al. Transcriptional regulation and transformation by Myc proteins. Nat Rev Mol Cell Biol. Aug. 2005;6(8):635-45.

Akimov et al., Bypass of Senescence, Immortalization, and Transformation of Human Hematopoietic Progenitor Cells, Stem Cells 23:1423-33, 2005.

Allergucci et al. Differences between human embryonic stem cell lines. Hum Reprod Update. Mar.-Apr. 2007;13(2):103-20.

Altschul et al. Gapped BLAST and PSI-BLAST: a new generation of protein database search programs. Nucleic Acids Research. 1997;25(17): 3389-3402.

Amit et al., Clonally Derived Human Embryonic Stem Cell Lines Maintain Pluripotency and Proliferative Potential for Prolonged Periods of Culture, Dev. Biol. 227:271-78, 2000.

Amsellem et al., Ex vivo Expansion of Human Hematopoietic Stem Cells by Direct Delivery of the HOXB4 Homeoprotein, Nat. Med. 9(11):1423-27, 2003.

Anderson et al. Transgenic enrichment of cardiomyocytes from human embryonic stem cells. Mol Ther. Nov. 2007; 15(11):2027-36.

Aoi et al. Generation of Pluripotent Stem Cells from Adult Mouse Liver and Stomach Cells. Science. Feb. 14, 2008. Published Online Feb. 14, 2008. Science DO1: 10.1126/science.1154884.

Asahi Shimbun Weekly AERA, The Novel Pluripotent Cells Established by Professor Yamanaka of Kyoto University May change Medical Care, pp. 72-73, Dec. 24, 2009, along with a partial English language translation thereof.

Assady et al. Insulin production by human embryonic stem cells. Diabetes. Aug. 2001;50(8): 1691-7.

Assou et al. A meta-analysis of human embryonic stem cells transcriptome integrated into a web-based expression atlas. Stem Cells. Apr. 2007;25(4):961-73.

Avilion et al., Multipotent Cell Lineages in Early Mouse Development Depend on SOX2 Function, Genes Dev. 17:126-40, 2003.

Bader et al. Leukemia inhibitory factor modulates cardiogenesis in embryoid bodies in opposite fashions. Circ Res. Apr. 14, 2000;86(7):787-94.

Bagutti et al. Differentiation of embryonal stem cells into keratinocytes: comparison of wild-type and beta 1 integrin-deficient cells. Dev Biol. Oct. 10, 1996; 179(1): 184-96.

Bang et al., Deconstructing Pluripotency, Science 320:58-59, 2008.

Barrett et al. NCBI GEO: mining tens of millions of expression profiles—database and tools update. Nucleic Acids Res. Jan. 2007;35(Database issue):D760-S.

Barrett et al., Activation Domains of L-Myc and c-Myc Determine Their Transforming Potencies in Rat Embryo Cells, Mol. Cell. Biol. 12(7):3130-37, 1992.

Bayani et al. Multi-color FISH techniques. Curr. Protoc. Cell Biol. 2004; Chapter 22:Unit 22.5.

Becker-Hapak et al. Protein transduction: generation of full-length transducible proteins using the TAT system. Curr Protoc Cell Biol. May 2003;Chapter 20: Unit 20.2.

Belmonte et al. "Induced pluripotent stem cells and reprogramming: seeing the science through the hype." Nat Rev Genet. Dec. 2009;10(12):878-83.

Bendall et al. IGF and FGF cooperatively establish the regulatory stem cell niche of pluripotent human cells in vitro. Nature. Aug. 30, 2007;448(7157): 1015-21.

Benetti et al., A Mammalian microRNA Cluster Controls DNA Methylation and Telomere Recombination Via RbI2-Dependent Regulation of DNA Methyltransferases, Nat. Struct. Mol. Biol. 15(3):268-79, published online Mar. 2, 2008.

Ben-Shushan et al., Rex-1, A Gene Encoding a Transcription Factor Expressed in the Early Embryo, Is Regulated via Oct-3/4 and Oct-6 Binding to an Octomer Site and a Novel Protein, Rox-1, Binding to an Adjacent Site, Mol. Cell Biol. 18(4):1866-78, 1998.

Berg et al. An argument against a role for Oct4 in somatic stem cells. Cell Stem Cell. Oct. 11, 2007;1(4):359-60.

Bibel et al., "Differentiation of mouse embryonic stem cells into a defined neuronal lineage," Nature Neuroscience, 2004, vol. 7, pp. 1003-1009.

Bigdeli et al., Adaptation of Human Embryonic Stem Cells to Feeder-Free and Matrix-Free Culture Conditions Directly on Plastic Surfaces. J. Biotec., 2008, vol. 133, pp. 146-153.

BioPorter™ Gene Therapy System, Inc., Wako Bio Window 40:7, 2002.

BioPorter™ Protein Delivery Reagent From www.biocarta.com.

Birnbaum et al. Slicing across Kingdoms: Regeneration in Plants and Animals. Cell. Feb. 22, 2008; 132(4):697-710.

Birrer et al., L-myc Cooperates With ras to Transform Primary Rat Embryo Fibroblasts, Mol. Cell. Biol. 8(6):2668-73, 1988.

Blackwood et al., Max: A Helix-Loop-Helix Zipper Protein That Forms a Sequence-Specific DNA-Binding Complex With Myc, Science 251(499*):1211-17, 1991.

Blelloch et al. Generation of Induced Pluripotent Stem Cells in the Absence of Drug Selection. Cell Stem Cell. 2007; 1,245-247.

Block et al., Population Expansion, Clonal Growth, and Specific Differentiation Patterns in Primary Cultures of Hepatocytes Induced by HGF/SF, EGF and TGFα in a Chemically Defined (HGM) Medium, J. Cell Biol. 132(6):1133-49, 1996.

Blow, N. Stem cells: in search of common ground. Nature. Feb. 14, 2008;451 (7180):855-8.

Bonetta, L. European Stem Cell Patents: Taking the moral High Road? Cell. Feb. 22, 2008;132(4):SI4-S16.

Boquest et al. Epigenetic programming of mesenchymal stem cells from human adipose tissue. Stem Cell Rev. 2006;2(4):319-29.

Bortvin et al., Incomplete Reactivation of Oct4-Related Genes in Mouse Embryos Cloned From Somatic Nuclei, Development 130:1673-80, 2003.

Boyer et al. Core Transcriptional Regulatory Circuitry in Human Embryonic Stem Cells. Cell. 2005;122(6):947-956.

(56) References Cited

OTHER PUBLICATIONS

Brambrink et al. Sequential Expression of Pluripotency Markers during Direct Reprogramming of Mouse Somatic Cells. Cell Stem Cell. 2008; 2, 151-159.
Brena et al. Quantitative assessment of DNA methylation: Potential applications for disease diagnosis, classification, and prognosis in clinical settings. J Mol Med. May 2006;84(5):365-77.
Brough et al., An Essential Domain of the c-Myc Protein Interacts With a Nuclear Factor That Is Also Required for E1A-Mediated Transformation, Mol. Cell. Biol. 15(3):1536-44, 1995.
Brüstle et al. Embryonic stem cell-derived glial precursors: a source of myelinating transplants. Science. Jul. 30, 1999;285(5428):754-6.
Burns et al. Diabetes mellitus: a potential target for stem cell therapy. Curr Stem Cell Res Ther. May 2006; 1 (2):255-66.
Buttery et al. Differentiation of osteoblasts and in vitro bone formation from murine embryonic stem cells. Tissue Eng. Feb. 2001;7(1):89-99.
Cai et al. Directed differentiation of human embryonic stem cells into functional hepatic cells. Hepatology. May 2007;45(5): 1229-39.
Campbell et al. Phosphonate Ester Synthesis Using a Modified Mitsunobu Condensation. J. Org. Chem.1994;59: 658-660.
Carey et al., "Reprogramming of murine and human somatic cells using a single polycistronic vector," Proc. Natl. Acad. Sci. USA, Jan. 6, 2009, vol. 106(1), pp. 157-62, Epub. Dec. 24, 2008. Erratum in: Proc. Natl. Acad. Sci. USA, Mar. 31, 2009, Vol.
Cartwright et al. LIF/STAT3 controls ES cell self-renewal and pluripotency by a Myc-dependent mechanism. Development. Mar. 2005; 132(5):885-96.
Chadwick et al. Cytokines and BMP-4 promote hematopoietic differentiation of human embryonic stem cells. Blood. Aug. 1, 2003; 102(3):906-15.
Chambers et al., Functional Expression Cloning of Nanog, A Pluripotency Sustaining Factor in Embryonic Stem Cells, Cell 113:643-55, 2003.
Chang et al. The c-Myc transactivation domain is a direct modulator of apoptotic versus proliferative signals. Mol Cell Biol. Jun. 2000;20(12):4309-19.
Chang et al., Embryonic Stem Cells/Induced Pluripotent Stem Cells, Stem Cells, 2009, vol. 27, pp. 1042-1049.
Check, E., Simple Recipe Gives Adult Cells Embryonic Powers, Nature 442:11, Jul. 6, 2006.
Chen et al. Analogous Organic-Synthesis of Small-Compound Libraries—Validation of Combinatorial Chemistry in Small-Molecule Synthesis. Journal of the American Chemical Society. 1994;116(6):2661-2662.
Chen et al. From stem cells to oligodendrocytes: prospects for brain therapy. Stem Cell Rev. Dec. 2007;3(4):280-8.
Cheng et al., Mammalian Grb2 Regulates Multiple Steps in Embryonic Development and Malignant Transformation, Cell 95:793-803, 1998.
Childs et al. Regression of metastatic renal-cell carcinoma after nonmyeloablative allogeneic peripheral-blood stem-cell transplantation. N Engl J Med. Sep. 14, 2000;343(11):750-8.
Chin et al. Induced pluripotent stem cells and embryonic stem cells are distinguished by gene expression signatures. Cell Stem Cell. Jul. 2, 2009;5(1): 111-23.
Cho et al. An unnatural biopolymer. Science. Sep. 3, 1993;261 (5126): 1303-5.
Cinalli et al. Germ Cells are Forever. Cell. Feb. 22, 2008; 132(4):559-562.
CIRM Public Release. $24 Million in New Stem Cell Research Funding Awarded to 25 California Institutions. California Institute for Regenerative Medicine (4 pages). Jun. 27, 2008.
CIRM: Summaries of Review for Applications to RFA 07-05. California Institute for Regenerative Medicine Web site. 2007. Available at: http://www.cirm.ca.gov/RFAIrfa__07-05/. Accessed Jul. 1, 2008.
Cline et al. Randomize Gene Sequences with New PCR Mutagenesis Kit. Strategies Newsletter. 2000; 13: 157-161.
Cohen et al., "Ooplasmic Transfer in Mature Human Oocytes," Molecular Human Reproduction, 1998, vol. 4, pp. 269-280.
Correction printed in Nature 447:897, Jun. 21, 2007.
Cosmo Bio News 49:5, 2005 (catalog of ES cell culture medium).
Coutts et al. Stem cells for the treatment of spinal cord injury. Exp Neurol. Feb. 2008;209(2):368-77.
Cowan et al. Nuclear Reprogramming of Somatic Cells After Fusion with Human Embryonic Stem Cells. Science, 2005, vol. 309, pp. 1369-1374.
Cowan et al., Derivation of Embryonic Stem-Cell Lines From Human Blastocysts, N. Engl. J. Med. 350:1353-56, 2004.
Cowling et al. Mechanism of transcriptional activation by the Myc oncoproteins. Semin Cancer Biol. Aug. 2006; 16(4):242-52.
Cyranoski et al. Simple switch turns cells embryonic. Nature. 2007; 447:618-619.
Cyranoski, D. Stem cells: 5 things to know before jumping on the iPS bandwagon. Nature. 2008;452(7186)406-408.
Cyranoski. Japan ramps up patent effort to keep iPS lead. Nature. 2008; 453(7198):962-3.
Daley et al. Prospects for Stem Cell Based Therapy. Cell. Feb. 22, 2008; 132(4):544-548.
Daley, et al., "Broader implications of defining standards for the pluripotency of iPSCs." Cell Stem Cell. Mar. 6, 2009;4(3):200-1; author reply 202.
D'Amour et al. Efficient differentiation of human embryonic stem cells to definitive endoderm. Nat Biotechnol. Dec. 2005;23(12):1534-41.
D'Amour et al. Production of pancreatic hormone-expressing endocrine cells from human embryonic stem cells. Nat Biotechnol. Nov. 2006;24(11): 1392-401.
Dang et al., The Biology of the Mammalian Kruppel-Like Family of Transcription Factors, Int. J. Biochem. Cell Biol. 32:1103-21, 2000.
Dani, et al. Differentiation of embryonic stem cells into adipocytes in vitro. J Cell Sci. Jun. 1997;110 (Pt 11):1279-85.
Deb, et al. Embryonic Stem Cells: From Markers to Market. Feb. 2008; 11(1): 19-37.
Denker, H. W. Human embryonic stem cells: the real challenge for research as well as for bioethics is still ahead of us. Cells Tissues Organs. 2008;187(4):250-6.
Dewitt et al. "Diversomers": an approach to nonpeptide, nonoligomeric chemical diversity. Proc Natl Acad Sci USA. Aug. 1, 1993;90(15):6909-13.
D'Ippolito et al. Marrow-isolated adult multilineage inducible (MIAMI) cells, a unique population of postnatal young and old human cells with extensive expansion and differentiation potential. J Cell Sci. Jun. 15, 2004; 117(Pt 14):2971-81.
Do et al., "Nuclei of Embryonic Stem Cells Reprogram Somatic Cells," Stem Cells, 2004, vol. 22, pp. 941-949.
Durcova-Hills et al. Induced reprogramming of human somatic cells into pluripotency: a new way how to generate pluripotent stem cells. Differentiation. Apr. 2008;76(4):323-5.
Ebert, L. Yamanaka scooped on iPS (stem cell) patent?!. TMCNews reports on Jan. 4, 2009. Available at http://ipbiz.blogspot.com/2009/01/yamanaka-scooped-on-ips-stemcell.html. Accessed May 19, 2009.
Ehrich et al. Quantitative high-throughput analysis of DNA methylation patterns by base-specific cleavage and mass spectrometry. Proc Natl Acad Sci USA. Nov. 1, 2005; 102(44): 15785-90.
Eisen et al. Cluster analysis and display of genome-wide expression patterns. Dec. 8, 1998;95(25): 14863-14868.
Elefanty, A. Ed. In this Issue . . . Stem Cell Research. 2008; 1:87.
Essentials of Stem Cell Biology, R. Lanza et al. Ed., 2006, Elsevier Academic Press, pp. 266-267.
Evans et al. Krüppel-like factor 4 is acetylated by p300 and regulates gene transcription via modulation of histone acetylation. J Biol Chem. Nov. 23, 2007;282(47): 33994-4002.
Evans et al., Establishment in Culture of Pluripotential Cells From Mouse Embryos, Nature 292:154-56, 1981.
Examination Report issued in Australian Patent Application No. 2006325975, Apr. 18, 2011.
Extended European Search Report issued in connection with European Patent Application No. 10154819.6, Jun. 10, 2010.
Extended European Search Report issued in connection with European Patent Application No. EP 06834636.0, Mar. 11, 2009.

(56) References Cited

OTHER PUBLICATIONS

Extended European Search Report issued in connection with European Patent Application No. EP 10154817.0, Jun. 10, 2010.
Extended European Search Report issued in connection with European Patent Application No. EP 10154821.2, Jun. 10, 2010.
Felgner et al. Lipofection: a highly efficient, lipid-mediated DNA-transfection procedure. Proc Natl Acad Sci USA. Nov. 1987;84(21):7413-7.
Feng et al., Reprogramming of Fibroblasts Into Induced Pluripotent Stem Cells With Orphan Nuclear Receptor Esrrb, Nature Cell Biology 11:197-203, 2009.
Ferrer-Costa et al. PMUT: a web-based tool for the annotation of pathological mutations on proteins. Bioinformatics. Jul. 15, 2005:21(14):3176-8.
Forsyth et al. Human Embryonic Stem Cell Telomere Length Impacts Directly on Clonal Progenitor Isolation Frequency. Rejuvenation Research. Feb. 2008;11(1):5-17.
Gallop et al. Applications of combinatorial technologies to drug discovery. 1. Background and peptide combinatorial libraries. J Med Chem. Apr. 29, 1994;37(9): 1233-51.
Ghaleb et al. Krüppel-like factors 4 and 5: the yin and yang regulators of cellular proliferation. Cell Res. Feb. 2005; 15(2):92-6.
Goswami et al. Embryonic stem cell therapy. IDrugs. Oct. 2007;10(10):713-9.
Griffiths-Jones et al., miRBase: Tools for microRNA Genomics, Nucleic Acids Research 36:D154-D158, published online Nov. 8, 2007.
Gu et al. Opposite regulation of gene transcription and cell proliferation by c-Myc and Max. Proc Nat! Acad Sci USA. Apr. 1, 1993;90(7):2935-9.
Ha et al. Cryopreservation of human embryonic stem cells without the use of a programmable freezer. Hum Reprod. Jul. 2005;20(7): 1779-85.
Hakelien et al. Reprogramming Fibroblasts to Express T-Cell Functions Using Cell Extracts. Nature Biotechnology, May 2002, vol. 20, pp. 460-466.
Hanna et al. Direct Reprogramming of Terminally Differentiated Mature B Lymphocytes to Pluripotency. Cell. Apr. 18, 2008;133: 250-264. Erratum in: Cell. 2008; 134(2):365.
Hanna et al., Direct Reprogramming of Terminally Differentiated Mature B Lymphocytes to Pluripotency, Cell 133:250-264, Apr. 17, 2008.
Hanna et al., Treatment of Sickle Cell Anemia Mouse Model With iPS Cells Generated From Autologous Skin, Science4 318(5858):1920-23, published online Dec. 6, 2007.
Hasegawa et al., Efficient Multicistronic Expression of a Transgene in Human Embryonic Stem Cells, Stem Cells 25:7107-12, 2007.
Hatfield et al., Stem Cell Division is Regulated by the microRNA Pathway, Nature 435(7044):974-978.
Heng et al. Incorporating protein transduction domains (PTD) within intracellular proteins associated with the 'stemness' phenotype. Novel use of such recombinant 'fusion' proteins to overcome current limitations of applying autologous adult stem cells in regenerative medicine? Med. Hypoth. Eden Press, 2005, vol. 64, pp. 992-996.
Hermann et al. Efficient generation of neural stem cell-like cells from adult human bone marrow stromal cells. J Cell Sci. Sep. 1, 2004; 117(Pt 19):4411-22.
Herold et al., Negative Regulation of the Mammalian UV Response by Myc Through Association with Miz-1, Mol. Cell 10(3):509-21, 2002.
Highfield, R. Dolly creator Proflan Wilmut shuns cloning. Available at http://www.telegraph.co.uk/earth/main.jhtml?xml=/earth/2007/11/16/scidolly116.xml. Accessed Nov. 12, 2008.
Hong et al., "Suppression of induced pluripotent stem cell generation by the p53-p21 pathway." Nature. Aug. 27, 2009;460(7259):1132-5.
Horikawa et al., Different Cis-Regulation of Human Versus Mouse TERT Gene Expression in vivo: Identification of a Human-Specific Repressive Element, proc. Natl. Acad. Sci. U.S.A. 102(51):18437-42, 2005.
Houbaviy et al., Embryonic Stem Cell-Specific MicroRNAs, Developmental Cell 5(2):351-58, 2003.
Hsiao et al., Marking Embryonic Stem Cells With a 2A Self-Cleaving Peptide: A NKX2-5 Emerald GFP BAC Reporter, PLoS ONE 3(7):e2532, 2008.
Huangfu et al., Efficient Induction of Pluripotent Stem Cells Using Small Molecule Compounds. Companion manuscript to U.S. Appl. No. 61/029,287.
Huangfu et al., Induction of Pluripotent Stem Cells by Defined Factors is Greatly Improved by Small-Molecule Compounds, Nature Biotechnology 26(7):795-97, 2008.
Huangfu et al., Induction of Pluripotent Stem Cells From Primary Human Fibroblasts With Only Oct4 and Sox 2, Nature Biotechnology 26:1269-1275, 2008.
Humphries, C., Reprogrammed Stem Cells Work on Parkinson's: A Study in Rodents Suggests that Skin Cells Can Be Transformed into Neurons to Treat Neurodegeneration, Technology Review, published by MIT, Apr. 8, 2008: http://www.technologyreview.com/printer.
Hwang et al., Evidence of Pluripotent Human Embryonic Stem Cell Line Derived From a Cloned Blastocyst, Science 303: 1669-74, 2004.
Hwang et al., Patient-Specific Embryonic Stem Cells Derived From Human SCNT Blastocycts, Science 308:1777-83, 2005.
Hyun et al. New advances in iPS cell research do not obviate the need for human embryonic stem cells. Cell Stem Cell. Oct. 11, 2007;1(4):367-8.
International Search Report issued with respect to PCT/JP2009/058873, mailed Jul. 7, 2009.
ltskovitz-Eldor et al., Differentiation of Human Embryonic Stem Cells Into Embryoid Bodies Comprising the Three Embryonic Germ Layers, Mol. Med. 6(2):88-95, 2000.
Itsykson et al. Derivation of neural precursors from human embryonic stem cells in the presence of noggin. Mol Cell Neurosci. Sep. 2005;30(1):24-36.
Jaenisch et al. Stem Cells, the Molecular Circuitry of Pluripotency and Nuclear Reprogramming. Cell. Feb. 22, 2008; 132(4):567-582.
Jahagirdar et al. Multipotent adult progenitor cell and stem cell plasticity. Stem Cell Rev. 2005;1(1):53-9.
Janssens et al. Autologous bone marrow-derived stem-cell transfer in patients with ST-segment elevation myocardial infarction: double-blind, randomised controlled trial. Lancet. Jan. 14, 2006;367(9505):113-21.
Jiang et al. A core Klf circuitry regulates self-renewal of embryonic stem cells. Nat Cell Biol. Mar. 2008; 10(3):353-60.
Jiang et al. In vitro derivation of functional insulin-producing cells from human embryonic stem cells. Cell Res. Apr. 2007; 17(4):333-44.
Jiang et al. Pluripotency of mesenchymal stem cells derived from adult marrow. Nature. Jul. 4, 2002;418(6893):41-9.
Jikken Igaku (Experimental Medicine) 24:814-19, 2006, along with an English language translation thereof.
Johnston et al. Minimum requirements for efficient transduction of dividing and nondividing cells by feline immunodeficiency virus vectors. J Virol. Jun. 1999;73(6):4991-5000.
Kaji et al., Virus-Free Induction of Pluripotency and Subsequent Excision of Reprogramming Factors, Nature, Mar. 1, 2009, vol. 458, Issue 7239, pp. 771-775.
Kamachi, et at. Mechanism of regulatory target selection by the SOX high-mobility-group domain proteins as revealed by comparison of SOX1/2/3 and SOX9. Mol Cell Biol. Jan. 1999;19(1):107-20.
Kanegae et al. Efficient gene activation in mammalian cells by using recombinant adenovirus expressing site-specific Cre recombinase. Nucleic Acids Res. Oct. 11, 1995;23(19):3816-21.
Kanellopoulou et al., Dicer-Deficient Mouse Embryonic Stem Cells Are Defective in Differentiation and Centromeric Silencing, Genes & Development 19:489-501, 2005.
Kawasaki et al. Induction of midbrain dopaminergic neurons from ES cells by stromal cell-derived inducing activity. Neuron. Oct. 2000;28(1):31-40.
Kehat et al. Human embryonic stem cells can differentiate into myocytes with structural and functional properties of cardiomyocytes. J Clin Invest. Aug. 2001; 108(3):407-14.
Kim et al. Ex vivo characteristics of human amniotic membrane-derived stem cells. Cloning Stem Cells. 2007 Winter; 9(4):581-94.

(56) References Cited

OTHER PUBLICATIONS

Kim et al., Generation of Human Induced Pluripotent Stem Cells by Direct Delivery of Reprogramming Proteins, Cell Stem Cell 4:472-476, 2009.

Kim et al., Oct4-Induced Pluripotency in Adult Neural Stem Cells, Cell 136:411-419, 2009.

Kim et al., Pluripotent Stem Cells Induced From Adult Neural Stem Cells by Reprogramming with Two Factors, Nature 454:656-650, 2008.

Kitamura et al. Retrovirus-mediated gene transfer and expression cloning: powerful tools in functional genomics. Exp Hematol. Nov. 2003;31(11):1007-14.

Kitamura, T. New experimental approaches in retrovirus-mediated expression screening. Int J Hematol. Jun. 1998 ;67(4):351-9.

Klingemann, H. Discarded stem cells with a future? Expert Opin Biol Ther. Dec. 2006 ;6(12): 1251-4.

Knoblich, J.A. Mechanisms of Asymmetric Stem Cell Division. Cell. Feb. 22, 2008; 132(4):583-597.

Koch et al. Transduction of human embryonic stem cells by ecotropic retroviral vectors. Nucl Acids Res. 2006; 34, e120.

Kohge et al. Promotion of antigen-specific antibody production in murine B cells by a moderate increase in histone acetylation. Biochem Pharmacol. Nov. 15, 1998;56(10): 1359-64.

Kohlhase et al., Cloning and Expression Analysis of Sall4, The Murine Homologue of the Gene Mutated in Okihiro Syndrome, Cytogenet. Genome Res. 98:274-77, 2002.

Kopsidas et al. RNA mutagenesis yields highly diverse mRNA libraries for in vitro protein evolution. BMC Biotechnol. Apr. 11, 2007;7:18.

Koyanagi et al., Screening and Functional Analysis of microRNAs which involve in Reprogramming, of Murine Somatic Cells, The Journal of Biochemistry, vol. 79, No. 11, Abstract 1T-7-7 From the 80th Annual Meeting of the Japanese Biochemical Society, Novemb.

Kramer et al. Embryonic stem cell-derived chondrogenic differentiation in vitro: activation by BMP-2 and BMP-4. Mech Dev. Apr. 2000;92(2):193-205.

Krausz, E. High-content siRNA screening. Mol Biosyst. Apr. 2007;3(4):232-40.

Krosl et al., In vitro Expansion of Hematopoietic Stem Cells by Recombinant TAT-HOXB4 Protein, Nat. Med 9(11):1428-32, 2003.

Kubicek et al., Reversal of H3K9me2 by a Small-Molecule Inhibitor for the G9a Histone Methyltransferase, Molecular Cell 25:473-81, 2007.

Kunath et al. FGF stimulation of the Erk1/2 signalling cascade triggers transition of pluripotent embryonic stem cells from self-renewal to lineage commitment. Development. Aug. 2007;134(16):2895-902.

Kuroda et al. Octamer and Sox Elements Are Required for Transcriptional cis Regulation of Nanog Gene Expression. Mol Cell Biol. Mar. 2005; 25(6):2475-2485.

Kyoto Shimbun (Japanese Newspaper) article of Apr. 16, 2008, columns 1-3, along with a partial English language translation thereof.

Laflamme et al, Cardiomyocytes Derived From Human Embryonic Stem Cells in Pro-Survival Factors Enhance Function of Infarcted Rat Hearts, Nat. Biotechnol. 25(9):1015-24, 2007.

Laird et al. Stem Cell Trafficking in Tissue Development, Growth, and Disease. Cell. Feb. 22, 2008; 132(4):612-630.

Lanza et al. (Eds.) Essentials of Stem Cell Biology. Elsevier Academic Press. 2006. (Table of Contents only).

Lee et al. Efficient generation of midbrain and hindbrain neurons from mouse embryonic stem cells. Nat Biotechnol. Jun. 2000;18(6):675-9.

Lemken et al. Evidence for intercellular trafficking of VP22 in living cells. Mol Ther. Feb. 2007;15(2):310-9.

Lengner et al. The pluripotency regulator Oct4: a role in somatic stem cells? Cell Cycle. Mar. 2008 ;7(6):725-8.

Lewitzky et al., "Reprogramming somatic cells towards pluripotency by defined factors." Curr Opin Biotechnol. Oct. 2007;18(5):467-73.

Li et al. Small dsRNAs induce transcriptional activation in human cells. Proc Natl Acad Sci. 2006; 103, 17337-17342.

Li et al., Leukaemia Disease Genes: Large-Scale Cloning and Pathway Predictions, Nat. Genet. 23(3):348-353, 1999.

Liao et al., Enhanced Efficiency of Generating Induced Pluripotent Stem (iPS) Cells From Human Somatic Cells by a Combination of Six Transcription Factors, Cell Research 18:600-603, doi: 10.1038/cr.2008.51, published online Apr. 15, 2008.

Lieschke et al. Development of functional macrophages from embryonal stem cells in vitro. Exp Hematol. Apr. 1995;23(4):328-34.

Lin et al., Mir-302 Reprograms Human Skin Cancer Cells into a Pluripotent ES-Cell-Like State, RNA 14:1-10, 2008.

Lin-Goerke et al. PCR-based random mutagenesis using manganese and reduced dNTP concentration. Biotechniques. Sep. 1997;23(3):409-12.

Link et al. Therapeutic protein transduction of mammalian cells and mice by nucleic acid-free lentiviral nanoparticles. Nucleic Acids Res. Jan. 30, 2006;34(2):e16.

Littlewood et al. A modified oestrogen receptor ligand-binding domain as an improved switch for the regulation of heterologous proteins. Nucleic Acids Res. May 25, 1995;23(10):1686-90.

Liu, S. iPS Cells: a More Critical Review. Stem Cells Dev. Jun. 2008;17(3):391-7.

Loh et al. The Oct4 and Nanog transcription network regulates pluripotency in mouse embryonic stem cells. Nat Genet. Apr. 2006;38(4):431-40.

Loriot et al., Five New Human Cancer-Germline Genes Identified Among 12 Genes Expressed in Spermatogonia, Int. J. Cancer 105:371-76, 2003.

Loudig et al. Transcriptional co-operativity between distant retinoic acid response elements in regulation of Cyp26A1 inducibility. Biochem J. Nov. 15, 2005;392(Pt 1):241-8.

Lowry et al. Generation of human induced pluripotent stem cells from dermal fibroblasts. Proc Natl Acad Sci USA. Feb. 26, 2008; 105(8):2883-8.

Ludwig et al. Derivation of human embryonic stem cells in defined conditions. Nat Biotechnol. Feb. 2006;24(2):185-7.

Lumelsky et al. Differentiation of embryonic stem cells to insulin-secreting structures similar to pancreatic islets. Science. May 18, 2001;292(5520):1389-94.

Lunde et al. Zebrafish pou5f1/pou2, homolog of mammalian Oct4, functions in the endoderm specification cascade. Curr Biol. Jan. 6, 2004;14(1):48-55.

Lungwitz et al. Polyethylenimine-based non-viral gene delivery systems. Eur J Pharm Biopharm. Jul. 2005;60(2):247-66.

Maherali et al. Directly reprogrammed fibroblasts show global epigenetic remodeling and widespread tissue contribution. Cell Stem Cell. Jun. 7, 2007;1(1):55-70.

Mali et al. Improved efficiency and pace of generating induced pluripotent stem cells from human adult and fetal fibroblasts. Stem Cells. Aug. 2008;26(8):1998-2005.

Marchetto et al. Transcriptional signature and memory retention of human-induced pluripotent stem cells. PLoS One. Sep. 18, 2009;4(9):e7076.

Marson et al., Wnt Signaling Promotes Reprogramming of Somatic Cells to Pluripotency, Cell Stem Cell 3:132-35, 2008.

Martin, Isolation of a Pluripotent Cell Line From Early Mouse Embryos Cultured in Medium Conditioned by Teratocarcinoma Stem Cells, Proc. Natl. Acad. Sci. U.S.A. 78(12):7634-38, 1981.

Maruyama et al., Differential Roles for Sox15 and Sox2 in Transcriptional Control in Mouse Embryonic Stem Cells, J. Biol., Chem. 280(26):24371-79, 2005.

Masaki et al. Heterogeneity of pluripotent marker gene expression in colonies generated in human iPS cell induction culture. Stem Cell Research. 2008; 1:105-115.

Masaki et al. Tendency of Pluripotential marker gene expression in colonies derived from human neonatal fibroblasts induced by the human iPS cell method. Stem Cell Researchr. 2008. doi: 10.1016/j.scr.2008.01.001 (Accepted Manuscript).

Mathe et al. Computational approaches for predicting the biological effect of p53 missense mutations: a comparison of three sequence analysis based methods. Nucleic Acids Res. Mar. 6, 2006;34(5):1317-25.

(56) References Cited

OTHER PUBLICATIONS

Matsuda et al. STAT3 activation is sufficient to maintain an undifferentiated state of mouse embryonic stem cells. Embo J. Aug. 2, 1999;18(15):4261-9.
McMahon et al., The Wnt-1 (int-1) Proto-Oncogene Is Required for Development of a Large Region of the Mouse Brain, Cell 62:1073-85, 1990.
Meiner et al, Disruption of the Acyl-CoA: Cholesterol Acyltransferase Gene in Mice: Evidence Suggesting Multiple Cholesterol Esterification Enzymes in Mammals, Proc. Natl. Acad. Sci. U.S.A. 93:14041-46, 1996.
Meissner et al. Direct reprogramming of genetically unmodified fibroblasts into pluripotent stem cells. Nat Biotech. 2007; 25, 1177-1181.
MicroRNA Jikken Purotokoru (microRNA Experimental Protocol), pp. 20-35, 2008, Yodosha Co., Ltd.
Mikkelsen et al. Dissecting direct reprogramming through integrative genomic analysis. Nature. Jul. 3, 2008;454(7200):49-55. Erratum in: Nature. 2008;454(7205):794.
Mitsui et al., The Homeoprotein Nanog Is Required for Maintenance of Pluripotency in Mouse Epiblast and ES Cells, Cell 113:631-42, 2003.
Miura et al. "Variation in the safety of induced pluripotent stem cell lines." Nat Biotechnol. Aug. 2009;27(8):743-5.
Miyagishi et al. Strategies for generation of an siRNA expression library directed against the human genome. Oligonucleotides. 2003;13(5):325-33.
Miyoshi et al. Development of a self-inactivating lentivirus vector. J Virol. Oct. 1998;72(10):8150-7.
More California Dough—$23 Million—Rolls Out the Door for Stem Cell Research. California Stem Cell Report Web Site. 2005. Available at: http://californiastemcellreport.blogspot.com/2008/06/more-dough-25-million-rolls-out-door-in.html. Accessed Jul. 1.
Morgenstern et al. Advanced mammalian gene transfer: high titre retroviral vectors with multiple drug selection markers and a complementary helper-free packaging cell line. Nucleic Acids Res. Jun. 25, 1990; 18(12):3587-3596.
Morita et al. Plat-E: An Efficient and Stable System for Transient Packaging of Retroviruses, Gene Ther. 7:1063-66, 2000.
Morizane et al. From bench to bed: the potential of stem cells for the treatment of Parkinson's disease. Cell Tissue Res. Jan. 2008;331(1):323-36.
Morling et al. Enhanced transduction efficiency of retroviral vectors coprecipitated with calcium phosphate. Gene Ther. Sep. 1995;2(7):504-8.
Morrison, S.J. Stem Cells and Niches: Mechanisms that Promote Stem Cell Maintenance throughout Life. Cell. Feb. 22, 2008; 132(4):598-611.
Mummery et al. Differentiation of human embryonic stem cells to cardiomyocytes: role of coculture with visceral endoderm-like cells. Circulation. Jun. 3, 2003; 107(21):2733-40.
Murry et al. Differentiation of Embryonic Stem Cells to Clinically Relevant Populations: Lessons from Embryonic Development. Cell. Feb. 22, 2008; 132(4):661-680.
Nagano et al., "Large-Scale Identification of Proteins Expressed in Mouse Embryonic Stem Cells," Proteomics 5:1346-1361, 2005.
Nagy et al. Embryonic stem cells alone are able to support fetal development in the mouse. Development. Nov. 1990;110(3):815-21.
Nakagawa et al., "Promotion of direct reprogramming by transformation-deficient Myc." Proc Natl Acad Sci U S A. Aug. 10, 2010;107(32):14152-7.
Nakagawa et al., Generation of Induced Pluripotent Stem Cells Without Myc From Mouse and Human Fibroblasts, Nat. Biotechnol. 26(1):101-06, published online Nov. 30, 2007.
Nakatake et al. Klf4 cooperates with Oct3/4 and Sox2 to activate the Lefty1 core promoter in embryonic stem cells. Mol Cell Biol. Oct. 2006;26(20):7772-82.
Naldini et al. In vivo gene delivery and stable transduction of nondividing cells by a lentiviral vector. Science. Apr. 12, 1996;272(5259):263-7.
Needleman et al. A general method applicable to the search for similarities in the amino acid sequence of two proteins. J Mol Biol. Mar. 1970;48(3):443-53.
Négre et al. Lentiviral vectors derived from simian immunodeficiency virus. Curr Top Microbiol Immunol. 2002;261:53-74.
Newton, Attracting World's Attention. Pluripotent Cells Are Generated From Human Skin. What is the 'iPS Cell' That Can Be Used Not Only in the Regeneration Therapy but Also in the Tailor-Made Therapy, pp. 70-75, Feb. 2008, along with a partial Engli.
Ng et al. Predicting the effects of amino acid substitutions on protein function. Annu Rev Genomics Hum Genet. 2006;7:61-80.
Nichols et al., Formation of Pluripotent Stem Cells in the Mammalian Embryo Depends on the POU Transcription Factor Oct4, Cell 95:379-91, 1998.
Nienhuis et al., Genotoxicity of Retroviral Integration in Hematopoietic Cells, Mol. Ther. 13(6):1031-49, 2006.
Niwa et al. Self-renewal of pluripotent embryonic stem cells is mediated via activation of STAT3. Genes Dev. Jul. 1, 1998;12(I3):2048-60.
Niwa et al., Efficient Selection for High-Expression Transfectants With a Novel Eukaryotic Vector, Gene 108(2):193-99,1991.
Nolte et al., Transduction of Pluripotent Human Hematopoietic Stem Cells Demonstrated by Clonal Analysis After Engraftment in Immune-Deficient Mice, Proc. Natl. Acad. Sci. USA 93(6):2414-19, 1996.
Office Action issued in connection with Chinese Patent Application No. 200680048227.7, Sep. 9, 2010.
Office Action issued in connection with European Patent Application No. EP 06834636.0, Apr. 30, 2010.
Office Action issued in connection with European Patent Application No. EP 06834636.0, Oct. 25, 2010.
Office Action issued in connection with Israeli Patent Application No. 191903, Aug. 19, 2010.
Office Action issued in connection with Japanese Patent Application No. JP 2009-056747, mailed Jun. 2, 2009.
Office Action issued in connection with Japanese Patent Application No. JP 2009-056748, mailed Jun. 2, 2009.
Office Action issued in connection with Japanese Patent Application No. JP 2009-056749, mailed Jun. 4, 2009.
Office Action issued in connection with Japanese Patent Application No. JP 2009-056750, mailed Jun. 2, 2009.
Office Action issued in connection with New Zealand Patent Application No. 569530, Apr. 20, 2010.
Office Action issued in connection with Singapore Patent Application No. 200804231-9, Apr. 13, 2010.
Office Action issued in connection with Singapore Patent Application No. 200901803-7, Jan. 22, 2010.
Official Action issued in connection with Eurasian Patent Application No. 200870046, Nov. 9, 2009.
Official Action issued in connection with Eurasian Patent Application No. 201000858, Jul. 14, 2010.
Official Action issued in connection with Japanese Patent Application No. JP 2009-056748, mailed Nov. 4, 2009.
Official Rejection issued in connection with Japanese Patent Application No. JP 2009-056748, mailed Feb. 23, 2010.
Official Rejection issued in connection with Japanese Patent Application No. JP 2009-056749, mailed Nov. 4, 2009.
Ohnuki et al., "Generation and characterization of human induced pluripotent stem cells." Curr Protoc Stem Cell Biol. Jun. 2009;Chapter 4:Unit 4A.2.
Okabe et al., Green Mice as a Source of Ubiquitous Green Cells, FEBS Letters, 1997, vol. 407, pp. 313-319.
Okamoto et al., A Novel Octamer Binding Transportation Factor is Differentially Expressed in Mouse Embryonic Cells, Cell 60:461-72, 1990.
Okita et al. Generation of germline-competent induced pluripotent stem cells. Nature Jul. 19, 2007; 448(7151)313-17.
Okita et al. Intracellular Signaling Pathways Regulating Pluripotency of Embryonic Stem Cells. Current Stem Cell Research & Therapy. 2006;1:103-111.
Okita et al., "Generation of mouse-induced pluripotent stem cells with plasmid vectors." Nat Protoc. 2010;5(3):418-28.

(56) References Cited

OTHER PUBLICATIONS

Okita et al., "Induction of pluripotency by defined factors." Exp Cell Res. Oct. 1, 2010;316(16):2565-70. Epub Apr. 24, 2010.
Okita et al., Generation of Mouse Induced Pluripotent Stem Cells Without Viral Vectors, Science 322(5903):949-53, published online Oct. 9, 2008.
Okuda et al., UTF1, A Novel Transcriptional Coactivator Expressed in Pluripotent Embryonic Stem Cells and Extra-Embryonic Cells, EMBO J. 17(7):2019-32, 1998.
Okumura-Nakanishi et al., "Oct-3/4 and Sox2 Regulate Oct-3/4 Gene in Embryonic Stem Cells," The Journal of Biological Chemistry 280(7):5307-5317, Feb. 18, 2006.
Onishi et al. Applications of retrovirus-mediated expression cloning. Exp Hematol. Feb. 1996;24(2):324-9.
Orkin et al. Hematopoiesis: An Evolving Paradigm for Stem Cell Biology. Cell. Feb. 22, 2008;132(4):631-644.
Osuna et al. Protein evolution by codon-based random deletions. Nucleic Acids Res. Sep. 30, 2004;32(17):e136.
Padmanabhan et al. Visualization of telomerase reverse transcriptase (hTERT) promoter activity using a trimodality fusion reporter construct. J Nucl Med. Feb. 2006;47(2):270-7.
Park et al. Reprogramming of human somatic cells to pluripotency with defined factors. Nature. 2008;451(7175):141-146.
Park, A. Stem-cell research: The quest resumes. Time Magazine. Feb. 9, 2009. Available at http://www.time.com/time/health/article/0,8599,1874717,00.html. Accessed Jun. 3, 2009.
Parson, A.B. Stem Cell Biotech: Seeking a Piece of the Action. Cell. Feb. 22, 2008; 132(4):511-513.
Pearson et al. Improved tools for biological sequence comparison. Proc Natl Acad Sci USA. Apr. 1988;85(8):2444-8.
Pearson, W.R. Rapid and sensitive sequence comparison with FASTP and FASTA. Methods Enzymol. 1990;183:63-98.
Peister et al., Gene Ther, Jan. 2004, vol. 11, Issue 2, pp. 224-228.
Pera, M.F. On the Road to Reprogramming. Stem Cell Research. 2008; 1:103-104.
Pomp et al. Generation of peripheral sensory and sympathetic neurons and neural crest cells from human embryonic stem cells. Stem Cells. Aug. 2005;23(7):923-30.
Postic et al., Dual Roles for Glucokinase in Glucose Homeostasis as Determined by Liver and Pancreatic β Cell-Specific Gene Knockouts Using Cre Recombinase, J. Biol. Chem 274(1):305-15.
Pralong et al. Cell fusion for reprogramming pluripotency: toward elimination of the pluripotent genome. Stem Cell Rev. 2006;2(4):331-40.
Prelle et al. Overexpression of insulin-like growth factor-II in mouse embryonic stem cells promotes myogenic differentiation. Biochem Biophys Res Commun. Nov. 2, 2000;277(3):631-8.
Qin et al., Direct Generation of ES-Like Cells From Unmodified Mouse Embryonic Fibroblasts by Oct4/Sox2/Myc/K1f4, Cell Res. 17(11):959-62, 2007.
Quenneville et al., Mol. Ther., Oct. 2004, vol. 10, Issue 4, pp. 679-687.
Rambhatla et al. Generation of hepatocyte-like cells from human embryonic stem cells. Cell Transplant. 2003;12(1):1-11.
Rao, M. Conserved and divergent paths that regulate self-renewal in mouse and human embryonic stem cells. Dev Biol. Nov. 15, 2004;275(2):269-86.
Ratajczak et al. Bone-marrow-derived stem cells—our key to longevity? J. Appl. Genet. 2007;48(4):307-319.
Reubinoff et al. Neural progenitors from human embryonic stem cells. Nat Biotechnol. Dec. 2001;19(12):1134-40.
Riviére et al. Effects of retroviral vector design on expression of human adenosine deaminase in murine bone marrow transplant recipients engrafted with genetically modified cells. Proc Natl Acad Sci USA. Jul. 18, 1995;92(15):6733-7.
Rodda et al. Transcriptional regulation of nanog by OCT4 and SOX2. J Biol Chern. Jul. 1, 2005;280(26):24731-7.
Rodriguez et al. Manipulation of OCT4 levels in human embryonic stem cells results in induction of differential cell types. Exp Biol Med (Maywood). Nov. 2007;232(10):1368-80.
Root et al. Genome-scale loss-of-function screening with a lentiviral RNAi library. Nat Methods. Sep. 2006;3(9):715-9.
Rosenfeld et al. Adenovirus-mediated transfer of a recombinant alpha 1-antitrypsin gene to the lung epithelium in vivo. Science. Apr. 19, 1991;252(5004):431-4.
Rossant, J. Stem Cell and Early Lineage Development. Cell. Feb. 22, 2008; 132(4):527-531.
Rossant, J. Stem Cells: The Magic Brew. Nature. Jul. 19, 2007;448, 260-262.
Rossi et al. Stem Cells and the Pathways to Aging and Cancer. Cell. Feb. 22, 2008; 132(4):681-696.
Rubin, L. Stem Cell and Drug Discovery: The Beginning of a New Era? Cell. Feb. 22, 2008; 132(4):549-552.
Ryan et al., POU Domain Family Values: Flexibility, Partnerships, and Developmental Codes, Genes Dev. 11:1207-25, 1997.
Sadowski et al. GAL4-VP16 is an unusually potent transcriptional activator. Nature. Oct. 6, 1988;335(6190):563-;4.
Sakai et al., A Transgenic Mouse Line That Retains Cre Recombinase Activity in Mature Oocytes Irrespective of the cre Transgene Transmission, Biochem. Biophys. Res. Commun. 237(2):318-24, 1997.
Saldanha et al. Assessment of telomere length and factors that contribute to its stability. Eur J Biochem. Feb. 2003;270(3):389-403.
Salmon et al., Reversible Immortalization of Human Primary Cells by Lentivector-Mediated Transfer of Specific Genes, Mol. Ther. 2(4):404-14, 2000.
Sato et al., Maintenance of Pluripotency in Human and Mouse Embryonic Stem Cells Through Activation of Wnt Signaling by a Pharmacological GSK-3-Specific Inhibitor, Nat. Med. 10(1):55-63, 2004.
Schepers et al., Twenty Pairs of Sox: Extent, Homology, and Nomenclature of the Mouse and Human Sox Transcription Factor Gene Families, Dev. Cell 3:167-70, 2002.
Scherr et al. Gene silencing by small regulatory RNAs in mammalian cells. Cell Cycle. Feb. 1, 2007;6(4):444-9.
Schuldiner et al. Induced neuronal differentiation of human embryonic stem cells. Brain Res. Sep. 21, 2001;913(2):201-5.
Schwenk et al. Hybrid embryonic stem cell-derived tetraploid mice show apparently normal morphological, physiological, and neurological characteristics. Mol Cell Biol. Jun. 2003;23(11):3982-9.
Science magazine names top 10 breakthroughs of 2008. Available at http://arstechnica.com/old/content/2008/12/isciencei-names-top-10-scientific-breakthroughs-of-2008.ars. Accessed May 19, 2009.
Shah, R. Pharmacogenetics in drug regulation: promise, potential and pitfalls. Philos Trans R Soc Lond B Biol Sci. Aug. 29, 2005; 360(1460):1617-1638.
Shao et al., Generation of iPS Cells Using Defined Factors Linked Via the Self-Cleaving 2A Sequences in a Single Open Reading Frame, Cell Res., Mar. 2009, vol. 19, Issue 3, pp. 296-312.
Shi et al., A Combined Chemical and Genetic Approach for the Generation of Induced Pluripotent Stem Cells, Cell Stem Cell 2:525-28, 2008.
Shi et al., Induction of Pluripotent Stem Cells From Mouse Embryonic Fibroblasts by Oct4 and Klf4 With Small-Molecule Compounds, Cell Stem Cell 3:568-74, 2008.
Silva et al. Capturing Pluripotericy. Cell. Feb. 22, 2008; 132(4):532-536.
Silva et al. Profiling essential genes in human mammary cells by multiplex RNAi screening. Science. Feb. 1, 2008;319(5863):617-20.
Silva et al., Promotion of Reprogramming to ground State Pluripotency by Signal Inhibition, PLoS Biology 6910):2237-47, 2008.
Sinkkonen et al., MicroRNAs Control de novo DNA Methylation Through Regulation of Transcriptional Repressors in Mouse Embryonic Stem Cells, Nat. Struct. Mol. Biol. 15(3):259-267, published online Mar. 2, 2008.
Skottman et al. Culture conditions for human embryonic stem cells. Reproduction. Nov. 2006;132(5):691-8.
Soldner et al., Parkinson's Disease Patient-Derived Induced Pluripotent Stem Cells Free of Viral Reprogramming Factors, Cell, Mar. 6, 2009, vol. 136, Issue 5, pp. 964-977.
Sottile et al. In vitro osteogenic differentiation of human ES cells. Cloning Stem Cells. 2003;5(2):149-55.

(56) References Cited

OTHER PUBLICATIONS

Spencer et al., E-Cadherin Inhibits Cell Surface Localization of the Pro-Migratory 5T4 Oncofetal Antigen in Mouse Embryonic Stem Cells, Mol. Biol. Cell 18:2838-51, 2007.
Spivakov et al., Epigenetic Signatures of Stem-Cell Identify, Nat. Rev. Genet. 8(4):263-271, 2007.
Stadler et al. Small RNAs: Keeping Stem Cells in Line. Cell. Feb. 22, 2008; 132(4):563-566.
Stadtfeld et al., Induced Pluripotent Stem Cells Generated Without Viral Integration, Science 322(5903):945-49, published online Sep. 25, 2008.
Stadtfeld, M. Defining molecular cornerstones during fibroblast to iPS cell reprogramming in mouse. Cell Stem Cell. Mar. 6, 2008;2(3):230-40.
Stem Cells Made to Mimic Disease, BBC News, http://newsvote.bbc.co.uk/mpapps/pagetools/print/news.bbc.co.uk/2/hi/health/7334365.stm, Apr. 7, 2008.
Stewart et al. Mechanisms of self-renewal in human embryonic stem cells. Eur J Cancer. Jun. 2006;42(9):1257-72.
Stojkovic et al. Derivation, growth and applications of human embryonic stem cells. Reproduction. Sep. 2004;128(3):259-67.
Strelchenko et al. Embryonic stem cells from morula. Methods Enzymol. 2006;418:93-108.
Suh et al., Human Embryonic Stem Cells Express a Unique Set of microRNAs, Developmental Biology 270:488-498, 2004.
Sumi et al. Apoptosis and differentiation of human embryonic stem cells induced by sustained activation of c-Myc. Oncogene. Aug. 16, 2007;26(38):5564-76.
Surani et al., A New Route to Rejuvenation, nature 443:284-285, Sep. 21, 2006.
Tada et al., Nuclear Reprogramming of Somatic Cells by in vitro Hybridization With ES Cells, Current Biology 11(19):1553-58, 2001.
Takahashi et al. Induction of pluripotent stem cells from adult human fibroblasts by defined factors. Cell. Nov. 30, 2007;131(5):861-72.
Takahashi et al. Induction of pluripotent stem cells from fibroblast cultures. Nat Protoc. 2007;2(12):3081-9.
Takahashi et al. Induction of pluripotent stem cells from mouse embryonic and adult fibroblasts by defined factors. Cell. Aug. 25, 2006; 126(4):663-676.
Takahashi et al., Induced Pluripotent Stem Cells, Jikken Igaku (Experimental Medicine) 26(5):35-40, 2008.
Takahashi et al., Role of ERas in Promoting Tumour-Like Properties in Mouse Embryonic Stem Cells, Nature 423:541-45, 2003.
Takahashi, K. et al. "Human induced pluripotent stem cells on autologous feeders." PLoS One. Dec. 2, 2009;4(12):e8067.
Takeda et al., Characterization of Dental Pulp Stem Cells of Human Tooth Germs, Journal of Dental Research, 2008, vol. 87, pp. 676-681.
Takeda et al., Human Oct3 Gene Family: cDNA Sequences, Alternative Splicing, Gene Organization, Chromosomal Location, and Expression at Low Levels in Adult Tissues, Nucleic Acids Research 20(17):4613-4620, 1992.
Tan et al. Changing viral tropism using immunoliposomes alters the stability of gene expression: implications for viral vector design. Mol Med. Mar.-Apr. 2007; 13(3-4):216-26.
Tantin et al. High-throughput biochemical analysis of in vivo location data reveals novel distinct classes of POU5FI(Oct4)/DNA complexes. Genome Res. Apr. 2008;18(4):631-9.
Taranger et al., Induction of Dedifferentiation, Genomewide Transcriptional Programming, and Epigenetic reprogramming by Extracts of Carcinoma and Embryonic Stem Cells, Mol. Biol. Cell 16:5719-35, 2005.
Tateno et al., Heterogeneity of Growth Potential of Adult Rat Hepatocytes in vitro, Hepatology 31(1):65-74, 2000.
The Japan Times. Bayer team makes stem cells from skin. Apr. 12, 2008. Available at http://search.japantimes.co.jp/cgi-bin/nn20080412a5.html. Accessed May 19, 2009.
Thomson et al. Embryonic Stem Cell Lines Derived from Human Blastocysts. Science. Nov. 1998;282(5391):1145.
Time. The Top 10 Everything of 2008-1. First Neurons Created from ALS Patients. Available at http://www.time.com/time/specials/2008/top10/article/0,30583,1855948_1863993,00.html. Accessed Dec. 15, 2008.
Tokuzawa et al. Utilization of Digital Differential Display to Identify Novel Targets of Oct3/4. In: Turksen, K., ed. Embryonic Stem Cell Protocols: vol. I: Isolation and Characterization. Humana Press; 2nd ed. Edition. Feb. 15, 2006: 223-231.
Tokuzawa et al., Fbx15 Is a Novel Target of Oct3/4 but is Dispensible for Embryonic Stem Cell Self-Renewal and Mouse Development, Mol. Cell Biol. 23(8):2699-718, 2003.
Trompeter, et. al. Rapid and highly efficient gene transfer into natural killer cells by nucleofection. J Immunol Methods. Mar. 1, 2003 ;274(1-2):245-56.
Troyanskaya et al. Nonparametric methods for identifying differentially expressed genes in microarray data. Bioinformatics. 2002;18(11): 1454-1461.
Tsai et al. In vivo immunological function of mast cells derived from embryonic stem cells: an approach for the rapid analysis of even embryonic lethal mutations in adult mice in vivo. Proc Natl Acad Sci USA. Aug. 1, 2000;97(16):9186-90.
Tsubooka et al. "Roles of Sall4 in the generation of pluripotent stem cells from blastocysts and fibroblasts." Genes Cells. Jun. 2009;14(6):683-94.
Tsunoda, Y., et al., The Recent Progress on Nuclear Transfer in Mammals, Zoological Science 17:1177-1184, 2000.
Tzukerman et al. Identification of a novel transcription factor binding element involved in the regulation by differentiation of the human telomerase (hTERT) promoter. Mol Biol Cell. Dec. 2000;11(12):4381-91.
Ulloa-Montoya et al. Comparative transcriptome analysis of embryonic and adult stem cells with extended and limited differentiation capacity. Genome Biol. 2007;8(8):R163.
Vallier et al. Activin/Nodal and FGF pathways cooperate to maintain pluripotency of human embryonic stem cells. J Cell Sci. Oct. 1, 2005;118(Pt 19):4495-509.
Vermeesch et al. Guidelines for molecular karyotyping in constitutional genetic diagnosis. Eur J Hum Genet. Nov. 2007;15(11):1105-14.
Verrey et al., CATs and HATs: The SLC7 Family of Amino Acid Transporters, Pflugers Archive-European Journal of Physiology, DOI 10.1007/s00424-003-1086-Z, pp. 1-23, published online Jun. 11, 2003.
Vintersten et al., Mouse in Red: Red Fluorescent Protein Expression in Mouse ES Cells, Embryos, and Adult Animals, Genesis 4041-46, 2004.
Viswanathan et al., Selective Blockade of MicroRNA Processing by Lin28, Science 320:97-100, 2008.
Vogel, G. Breakthrough of the year. Reprogramming Cells. Science. Dec. 19, 2008;322(5909): 1766-7.
Wadia et al., Protein Transduction Technology, Curr. Opin. Biotechnol. 13:52-56, 200.
Wagner et al. Mesenchymal stem cell preparations—comparing apples and oranges. Stem Cell Rev. Dec. 2007;3(4):239-48.
Wakao et al., "Multilineage-Differentiating Stress-Enduring (Muse) Cells Are a Primary Source of Induced Pluripotent Stem Cells in Human Fibroblasts," PNAS Early Edition, pp. 1-6, May 31, 2011, available at www.pnas.org/cgi/content/short/1100816108.
Wakayama et al., Differentiation of Embryonic Stem Cell Lines Generated From Adult Somatic Cells by Nuclear Transfer, Science 292:740-43, 2001.
Wakayama et al., Full-Term Development of Mice From Enucleated Oocytes Injected With Cumulus Cell Nuclei, Nature 394:369-74, 1998.
Wang et al. Inhibition of caspase-mediated anoikis is critical for bFGF-sustained culture of human pluripotent stem cells. J Biol Chem. Oct. 16, 2009. [Epub ahead of print].
Wang et al., A Protein Interaction Network for Pluripotency of Embryonic Stem Cells, Nature 444:364-68, 2006.
Watanabe et al. A ROCK inhibitor permits survival of dissociated human embryonic stem cells. Nat Biotechnol. 2007; 25, 681-686.
Watson et al. Identifying Genes Regulated in a Myc-dependent Manner. J Biol Chem. Oct. 4, 2002;277(40):36921-30.

(56) References Cited

OTHER PUBLICATIONS

Werbowetski-Ogilvie et al. Characterization of human embryonic stem cells with features of neoplastic progression. Nat Biotechnol. Jan. 2009;27(1):91-7.
Wernig et al. c-Myc is dispensable for direct reprogramming of mouse fibroblast. Cell Stem Cell. 2008; 2, 10-12.
Wernig et al. In vitro reprogramming of fibroblasts into a pluripotent ES-cell-like state. Nature. Jul. 19, 2007;448:318-324.
Wernig et al. Neurons derived from reprogrammed fibroblasts functionally integrate into the fetal brain and improve symptoms of rats with Parkinson's disease. Proc Natl Acad Sci USA. Apr. 15, 2008;105(15):5856-61.
Wernig et al., Neurons Derived From Reprogrammed Fibroblasts Functionally Integrate Into the Fetal Brain and Improve Symptoms of Rats With Parkinson's Disease, Proc. Natl. Acad. Sci. U.S.A. 105(15):5856-5861, 2008.
What are adult stem Cells? Stem Cell Information. The National Institutes of Health resource for stem cell research. 2007. Available at: http://stemcells.nih.gov/info/basics/basics4.asp. Accessed Jun. 4, 2007.
Wilmut et al., Viable Offspring Derived From Fetal and Adult Mammalian Cells, Nature 385:810-13, 1997.
Woltjen et al., PiggyBac Transposition Reprograms Fibroblasts to Induced Pluripotent Stem Cells, Nature, Mar. 1, 2009, vol. 458, Issue 7239, pp. 766-770.
Wu et al. Origins and Fates of Cardiovascular Progenitor Cells. Cell. Feb. 22, 2008; 132(4):537-543.
Wu et al., Sall4 Interacts With Nanog and Co-Occupies Nanog Genomic Sites in Embryonic Stem Cells, J. Biol., Chem., 281(34):24090-24094, 2000.
Xu et al. BMP4 initiates human embryonic stem cell differentiation to trophoblast. Nat Biotechnol. Dec. 2002;20(12):1261-4.
Xu et al. Random mutagenesis libraries: optimization and simplification by PCR. Biotechniques. Dec. 1999;27(6):1102, 1104, 1106, 1108.
Xu et al., Basic FGF and Suppression of BMP Signaling Sustain Undifferentiated Proliferation of Human ES Cells, Nat. Methods 2(3):185-90, 2005.
Yamanaka et al., "Nuclear reprogramming to a pluripotent state by three approaches." Nature. Jun. 10, 2010;465(7299):704-12.
Yamanaka et al., Mouse Sen'iga Saibo Kara Yudo Tansosei Kansaibo o Tsukuru (Induction of Pluripotent Stem Cells From Mouse Fibroblast Cultures) Tanpakushitsu Kakusan Koso (Protein, Nucleic Acid and Enzyme) 51(15):2346-51, 2006.
Yamanaka S., "An interview with . . . Shinya Yamanaka. Interview by Mary Muers." Nat Rev Genet. Jun. 2010;11(6):390.
Yamanaka S., "Patient-specific pluripotent stem cells become even more accessible" Cell Stem Cell. Jul. 2, 2010;7(1):1-2.
Yamanaka S., "Pluripotency and nuclear reprogramming." Philos Trans R Soc Lond B Biol Sci. Jun. 27, 2008;363(1500):2079-87.
Yamanaka S., "Symposium: Nuclear reprogramming and the control of differentiation in mammalian embryos. Introduction." Reprod Biomed Online. Jan. 2008;16(1):11-2.
Yamanaka, Pluripotency of Differentiation and miRNA, The Journal of Biochemistry, vol. 79, No. 11, Abstract 3BT17 From the 80th Annual Meeting of the Japanese Biochemical Society, Nov. 25, 2007, along with an English language translation thereof.
Yamanaka, S. Induction of Pluripotent stem cells from mouse fibroblasts by four transcription factors. Cell Prolif. 2008;41 (Suppl. 1): 51-56.
Yamanaka, S. Strategies and new developments in the generation of patient-specific pluripotent stem cells. Cell Stem Cell. Jun. 7, 2007;1(1):39-49.
Yamanaka, S., "A fresh look at iPS cells." Cell. Apr. 3, 2009;137(1):13-7.
Yamanaka, S., "Ekiden to iPS Cells." Nat Med. Oct. 2009;15(10):1145-8.
Yamanaka, S., "Elite and stochastic models for induced pluripotent stem cell generation." Nature. Jul. 2, 2009;460(7251):49-52.
Yamanaka, S., "Induction of Pluripotency by Defined Factors—The History of iPS Cells", Gairdner Award acceptance speech, presented on or about Oct. 29, 2009.
Yamanaka, S., "Induction of Pluripotency by Defined Factors", lecture presented on or about Oct. 29, 2009.
Yamane et al. Derivation of melanocytes from embryonic stem cells in culture. Dev. Dyn. 1999;216:450-458.
Yamashita et al. Flk1-positive cells derived from embryonic stem cells serve as vascular progenitors. Nature. Nov. 2, 2000;408(6808):92-6.
Yang et al., Nuclear Reprogramming of Cloned Embryos and Its Implications for Therapeutic Cloning, Nat. Genet. 39(3):295-302, 2007.
Yee et al. Generation of high-titer pseudotyped retroviral vectors with very broad host range. Methods Cell Biol. 1994;43 Pt A:99-112.
Ying et al., BMP Induction of ID Proteins Suppresses Differentiation and Sustains Embryonic Stem Cell Self-Renewal in Collaboration With STAT3, Cell 115:281-92, 2003.
Ying et al., The MicroRNA: Overview of the RNA Gene That Modulates Gene Functions, Methods in Molecular Biology, MicroRNA Protocols, vol. 342, pp. 1-18, Humana Press, 2006.
Yoshida et al. "Hypoxia enhances the generation of induced pluripotent stem cells." Cell Stem Cell. Sep. 4, 2009;5(3):237-41. Epub Aug. 27, 2009.
Yoshida et al., "Recent stem cell advances: induced pluripotent stem cells for disease modeling and stem cell-based regeneration." Circulation. Jul. 6, 2010;122(1):80-7.
Yu et al. Induced pluripotent stem cell lines derived from human somatic cells. Science. Dec. 21, 2007;318(5858):1917-20.
Yu et al., Human Induced Pluripotent Stem Cells Free of Vector and Transgene Sequences, Science 324:797-801, 2009.
Yuasa et al. Transient inhibition of BMP signaling by Noggin induces cardiomyocyte differentiation of mouse embryonic stem cells. Nat Biotechnol. May 2005;23(5):607-11.
Zhan et al. Conservation and variation of gene regulation in embryonic stem cells assessed by comparative genomics. Cell Biochem Biophys. 2005;43(3):379-405.
Zhang et al. In vitro differentiation of transplantable neural precursors from human embryonic stem cells. Nat Biotechnol. Dec. 2001;19(12):1129-33.
Zhang et al., MicroRNA: A New Player in Stem Cells, Journal of Cellular Physiology 209:266-269, 2006.
Zhao et al. Mechanisms and Functional Implications of Adult Neurogenesis. Cell. Feb. 22, 2008; 132(4):645-660.
Zhao et al., "Two Supporting Factors Greatly Improve the Efficiency of Human iPSC Generation" *Cell Stem Cell* 3:475-79, 2008.
Zhou et al., Generation of Induced Pluripotent Stem Cells Using Recombinant Proteins, Cell Stem Cell 4:381-384, 2009.
Ziegler et al., The Cationic Cell-Penetrating Peptide $CPP^{TAT}$ Derived From the HIV-1 Protein TAT is Rapidly Transported into Living Fibroblasts: Optical, Biophysical, and Metabolic Evidence, Biochemistry 44:138-148, published online Dec. 14, 2004.
Bongso, A., et al., Isolation and Culture of Inner Cell Mass Cells From Human Blastocysts, Human Reproduction 9(11):2110-2117, 1994.
Crouch, D.H., et al., Multiple Phenotypes Associated With Myc-Induced Transformation of Chick Embryo Fibroblasts Can Be Dissociated by a Basic Region Mutation, Nucleic Acids Research 24(16):3216-3221, 1996.
International Search Report and Written Opinion issued in PCT/JP2011/051685.
Nakagawa, M., et al., Promotion of Direct Reprogramming by Transformation-Deficient Myc., Proc. Natl. Acad. Sci. USA *107*(32):14152-14157, Aug. 2010.
Sarid, J., et al., Evolutionarily Conserved Regions of the Human c-Myc Protein Can Be Uncoupled From Transforming Activity, Proc. Natl. Acad. Sci. USA *84*(1):170-173, 1987.
European Examination Report on EP 07 856 194.1, issued Sep. 29, 2011.
Examination Report dated Oct. 15, 2012, issued in connection with European Patent Application No. 10154821.2.
Examination Report dated Oct. 23, 2012, issued in connection with European Patent Application No. 10154819.6.

(56) References Cited

OTHER PUBLICATIONS

Li, H., et al., Pluripotent Stem Cells From the Adult Mouse Inner Ear, Nature Medicine 9(10):1293-1299, Oct. 2003.
First Office Action dated Aug. 31, 2012 in corresponding Chinese patent application No. 200880100396.X.
Rybouchkin, A., et al., Role of Histone Acetylation in Reprogramming of Somatic Nuclei Following Nuclear Transfer, Biology of Reproduction 74:1083-1089, 2006.
Examination report dated Dec. 11, 2012 and issued to related European application No. 10154817.0.

* cited by examiner

Figure 1 Sample

Figure 2  Database

User Interface

Kit

PROVIDING IPSCS TO A CUSTOMER

CROSS-REFERENCE

This application is a continuation-in-part of U.S. application Ser. No. 12/157,967 now U.S. Pat. No. 8,211,679, filed Jun. 13, 2008, which claims the benefit of U.S. Provisional Application No. 61/040,646, filed Mar. 28, 2008, and which also claims the benefit of International Application No. PCT/EP2007/010019, filed Nov. 20, 2007, and which also claims the benefit of Japanese Application No. JPO-2007-159382, filed Jun. 15, 2007; this application also claims the benefit of International Application No. PCT/IB2008/002540, filed Jun. 13, 2008, International Application No. PCT/EP2008/005047, filed Jun. 13, 2008, U.S. Provisional Application No. 61/061,592, filed Jun. 13, 2008, and U.S. Provisional Application No. 61/061,594, filed Jun. 13, 2008, all of which are herein incorporated by reference in their entirety.

BACKGROUND OF THE INVENTION

Regenerative medicine includes therapies designed to aid the repair, replacement, or regeneration of damaged cells, tissues, or organs. One branch of regenerative medicine includes therapies that rely on embryonic stem cells (ES), which have the potential to give rise to a diverse range of cell types. ES-based therapies have the promise of treating a variety of health conditions including degenerative diseases, proliferative diseases, hereditary diseases, injuries, and organ failures. However, the progress of such therapies has been hindered by a range of factors including the possibility of immune rejection of ES cells derived from a donor who is immunologically incompatible with the recipient, as well as ethical and legal concerns.

SUMMARY OF THE INVENTION

Provided herein are methods for providing or conducting a regenerative medicine business or stem cell technology service comprising providing a service for obtaining a sample of human postnatal tissue or cells from a customer, donor, or third party; and generating or obtaining induced pluripotent stem cells (iPSCs) from the sample. In some embodiments, the cells obtained from the sample are induced stem cells, or induced multipotent stem cells. In some embodiments, the method further comprises manipulating the sample in order to force expression of: (a) one or more of the following polypeptides: Oct3/4, Sox2, Klf4, and c-Myc, or polypeptides; or (b) one or more of the following polypeptides: a polypeptide greater than 70% identical to Oct3/4, a polypeptide greater than 70% identical to Sox2, a polypeptide greater than 70% identical to Klf4, and a polypeptide greater than 70% identical to c-Myc. In some embodiments, the method comprises forcing expression of Oct3/4, Sox2, and Klf4 polypeptides. In some embodiments, the method further comprises a sample, wherein the sample is obtained at the donor's residence, a hospital, clinic, doctor's office, a blood bank, blood mobile, cell-banking facility, fertility clinic, health-care facility or other regenerative medicine business or business related to iPS cell technology.

In some embodiments, the sample is comprised of one or more of the following: fibroblasts, dermal fibroblasts, bone marrow derived mononuclear cells, skeletal muscles cells, adipose cells, peripheral blood mononuclear cells, macrophages, hepatocytes, keratinocytes, hair follicle dermal cells, gastric epithelial cells, lung epithelial cells, synovial cells, kidney cells, skin epithelial cells, and somatic cells. In some embodiments, the sample is comprised of one or more of the following: cells collected from an infant near birth or delivery, placenta, and umbilical cord blood.

In some embodiments, the method further comprises the step of differentiating the iPS cell into one or more of the following: a neural stem cell, a liver stem cell, a hematopoietic stem cell, or a cardiac stem cell; a hepatocyte, a cardiomyocyte, a neuron, an oligodendrocyte, an astrocyte, a dopaminergic neuron, a neuron, a motor neuron, or a pancreatic beta cell; one or more of the following types of tissue: skin, eye, liver, kidney, lung, pancreas, intestine, muscle, ligament, joint, or limb; and any cell, organ, tissue, or limb.

Also provided herein are methods for conducting a stem cell technology business, comprising providing a service for accepting and logging in a sample from a customer, donor, or third party, wherein the sample comprises one or more induced pluripotent stem cells (iPSCs) or one or more cells differentiated from an iPSC cell.

In some embodiments, the method further comprises differentiating the one or more iPS cells into one or more of the following: (a) a neural stem cell, a liver stem cell, a hematopoietic stem cell, or a cardiac stem cell; (b) a hepatocyte, a cardiomyocyte, a neuron, an oligodendrocyte, an astrocyte, a dopaminergic neuron, neuron, motor neuron, or pancreatic beta cells; (c) one or more of the following types of tissue: skin, eye, liver, kidney, lung, pancreas, intestine, muscle, ligament, joint, or limb; and (d) any cell, organ, tissue, or limb.

In some embodiments, the method further comprises culturing, expanding, or maintaining the one or more iPSCs or the one or more cells differentiated from an iPSC. In some embodiments, the method further comprises storing the sample in a freezer or incubator, or subjecting the sample to cryogenic freezing. In some embodiments, the method further comprises a donor wherein the donor comprises: an individual suffering from a disease or disorder, an individual who is genotypically wild-type at the locus of a gene identified as relevant to a specific disease or disorder, or an individual who anticipates developing, or is at risk of developing, a disease or disorder. In some embodiments, the disease or disorder is hereditary. In some embodiments, the customer is suffering from one or more of the following diseases or conditions: neurodegenerative disorders; neurological disorders such as cognitive impairment, and mood disorders; auditory disease such as deafness; osteoporosis; cardiovascular diseases; diabetes; metabolic disorders; respiratory diseases; drug sensitivity conditions; eye diseases such as macular degeneration; immunological disorders; hematological diseases; kidney diseases; proliferative disorders; genetic disorders, traumatic injury, stroke, organ failure, or loss of limb. In some embodiments, the method further comprises obtaining information from the donor, wherein obtaining information comprises determining donor biographical or demographic data including one or more of the following: age, sex, race, ethnic background, medical history, diseases or conditions suffered, or anticipated diseases or conditions.

In some embodiments, the method further comprises analyzing donors, wherein analyzing comprises determining donor molecular profiles including one or more of the following: SNP, InDel, VNTR, RFLP profiles; gene expression profiles; protein expression profile, HLA-type, genomic sequence. In some embodiments, the method further comprises analyzing samples for malignant or pre-malignant changes. In some embodiments, the method further comprises analyzing samples wherein the analyzing comprises analyzing the sample for gene expression or for morphogenic characteristics. In some embodiments, the method further comprises consulting a database comprising one or more of the following: (a) data relating to donors or samples; (b) customer data; (c) sample inventory; and (d) sample history.

In some embodiments, the method further comprises methods of searching for a sample in the database based on one or more of the following criteria: donor's physician; storage location; biographical data; demographic data; genomic sequence data; SNP, InDel, or VNTR profile; disease state of the donor or sample, cell or tissue type; HLA-type; medical history; or sample history. In other embodiments, the method further comprises retrieving, marketing, or selling a sample based upon the results of a database search. In some aspects, provided herein are kits for acquisition and storage of samples in a manner compatible with the methods of the regenerative medicine business comprising one or more of the following: (a) a means for obtaining a sample of somatic cells from a donor; (b) reagents and materials for storage of somatic cells in a manner suitable for induction of iPSCs; and (c) instructions for use of the kit. In some embodiments, the method further comprises a means for recording donor and sample information. In some embodiments, the method further comprises one or more of the following:
(a) reagents and materials for culturing somatic cells, iPSCs and cells derived thereof including one or more of the following: cell culture media, antibiotics, and cell culture dishes; (b) a means for generating iPSCs from somatic cells including one or more of the following: plasmids encoding induction factors (IFs), transfection reagents, and recombinant viruses; a means of recording donor and sample information; a means of inputting donor and sample information into a database; and a temporary license for the use of iPSC technology.

INCORPORATION BY REFERENCE

All publications and patent applications mentioned in this specification are hereby incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

I. Overview

Figure 1:
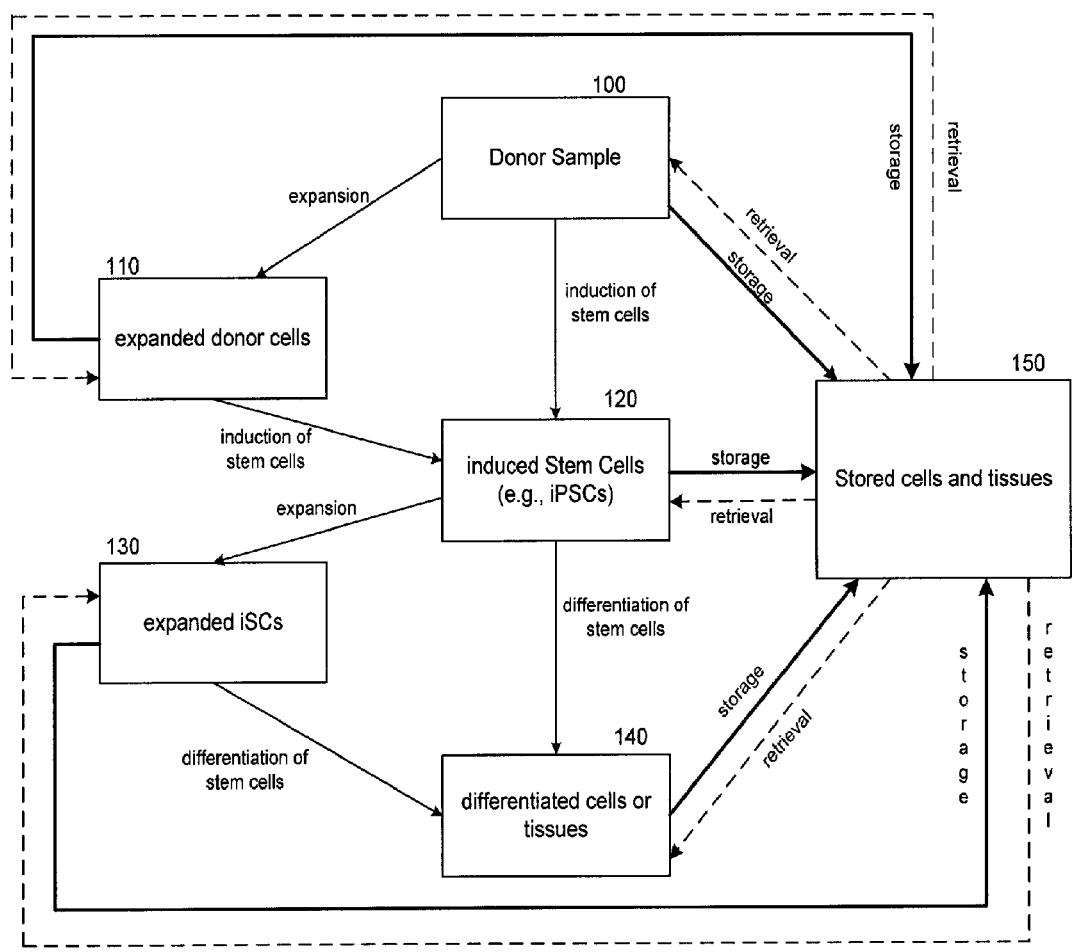
FIG. 1: is an overview of methods of storage and handling of biological samples for a regenerative medicine business based on iSC technology (e.g., iPSC or iMSC technology).

The present disclosure features methods for running a regenerative medicine or other cell-based business using induced pluripotent stem cells (iPSCs) (also known as "iPS cells") including related methods, kits, and compositions. A regenerative medicine business using iPSC technology may fulfill an unmet need with regard to the current lack of large scale availability of induced stem cells to the general population. In addition, the use of iPSC technology may minimize or alleviate some legal and ethical problems associated with other stem cell technologies such as embryonic stem cells. In some cases, a regenerative business may provide iPSCs to an individual (e.g., customer, patient, physician, medical professional, scientist, etc.) or to an entity (e.g., hospital, pharmaceutical company, healthcare facility, HMO, etc.) for the purpose of replacing, regenerating, enhancing, or otherwise influencing the growth or character of tissue in an in vitro, in vivo, or in situ setting. In some cases, the iPSCs, or cells differentiated from iPSCs, are transplanted into a patient or individual seeking treatment. In some cases, the iPSCs are used to generate panels of cells, e.g., panels of genetically-heterogenous cells, for use in drug-screening platforms.

Methods described in this disclosure include methods and compositions for obtaining and storing cells from a donor or third party for the purpose of inducing a somatic cell (e.g., a differentiated somatic cell or undifferentiated somatic cell) to become a pluripotent stem cell. Methods of the present invention further include generating iPSCs from the obtained or stored cells, and generating differentiated cells and tissues from the iPSCs. The present invention further provides methods and compositions relating to the storage and banking of the iPSCs or of cells and tissues differentiated from the iPSCs. Such methods also may include storing and/or banking iPSCs, or storing and/or banking cells differentiated from iPSCs. Methods described herein also include methods for billing and receiving payment from donors, customers (e.g., pharmaceutical companies), and third parties (e.g., insurance agencies) for products and services of the regenerative medicine business.

Kits provided in the present invention include, a kit for the purpose of obtaining storing and shipping donor samples, a kit for the purpose of generating iPSCs and optionally storing the iPSCs or generating differentiated cells or tissues from the generated iPSCs, and a kit for providing and using iPSCs or differentiated cells and tissues derived from iPSCs to a donor, client, or third party such as a medical professional. The present invention also provides cell-replacement therapies for treatment of various conditions including diseases and conditions associated with tissue degeneration and injury.

Methods disclosed herein include using, consulting, operating or receiving information/data from a searchable database containing information on donors, samples and/or stored biological materials, including panels of iPSCs or panels of cells differentiated from iPSCs. In some cases, the disclosed methods (e.g., general methods, business methods) may also comprise receiving information, data, and/or results generated from a searchable database containing information about donors, samples and/or stored biological materials including panels of iPSCs, or panels of cells differentiated from iPSCs, or providing a service for receiving information, data, and/or results generated from a searchable database containing information about donors, samples and/or stored biological materials including panels of iPSCs, or panels of cells differentiated from iPSCs. In addition, business methods disclosed herein include using or operating a searchable database containing information on donors and stored biological materials. Business methods of the present invention include, a searchable database containing information on donors and stored biological materials. Business methods or other methods provided herein further include methods of marketing and selling the products and services of the regenerative medicine business including but not limited to cell and tissue storage, generation of iPSCs, generation of iPSCs, and generation of differentiated cells and tissues.

The term pluripotent stem cell has a meaning understood in the art, and includes the ability of a cell to differentiate into cell types of all three lineages or germ layers (viz. endoderm, ectoderm, and mesoderm). The term multipotent has a meaning understood in the art, and includes the ability of a cell to differentiate into multiple cell types. It is also understood that multipotent cells may be more restricted in their ability to differentiate than pluripotent cells. The term "iSCs", as used herein, refer to iPSCs or to induced multipotent stem cells (iMSCs). At times, the term "iPS" or "iPS cell" may be used instead of "iPSC"; similarly, at times the term "iMS" or "iMS cell" may be used instead of "iMSC". The methods and compositions described herein that are applicable to iPSCs are also applicable to induced stem cells (iSCs) and iMSCs.

iSCs (e.g., iPSCs or iPMCs) can be established from cells comprising the genome of the patient (autologous) or an individual with a close genetic match to the patient, thus reducing the potential for immunologic rejection of transplanted cells or tissues. At other times, iSCs (e.g., iPSCs or iPMCs) can be generated from or established from cells that are not closely-genetically matched to a patient. The iSCs (e.g., iPSCs or iPMCs) may also be characterized as capable of long term self renewal and/or possessing a normal karyotype.

One goal of regenerative medicine is to provide, administer, or transplant essentially any cell, tissue, or organ to an individual with minimal risk of immunological rejection. Currently transplantation is indicated when: 1) tissues and organs are available in reasonable number, 2) tissues and organs can be effectively harvested and transplanted 2) and patients are judged likely to survive the harsh regimen of immunosuppressive drugs often required to inhibit rejection.

A regenerative medicine business based on iPSC technology could circumvent one or more of the issues related to transplantation. For example, iPSCs have the ability to differentiate into multiple types of cells or tissues. Therefore, provided that viable cells from an individual are available, essentially all tissues, systems, and organs can be provided in large quantities. This advantage of having of iPSCs available from a single donor sample in large quantities also provides the particular advantage that such a sample may be available to a number of other clients related or unrelated to the original donor, with minimal risk of exhaustion of the original sample.

In many cases, obtaining viable brain, liver, neural, or pancreatic tissue may be extremely difficult and dangerous. However, harvesting of cells (e.g., cells from skin, blood, hair follicles, scalp, etc.) for use in iPSC technology can often be performed by a skilled artisan. For example, a skilled artisan may harvest cells from skin, blood, etc., and such cells may later be used to generate or establish iPSCs or iMSCs, which cells may later be differentiated into more mature cell-types, e.g., neural progenitor cells, neurons, pancreatic beta cells, hepatocytes, cardiomyocytes. In addition, because the cells, tissues, and organs may ultimately derive from the same individual receiving the material, the likelihood of rejection may be minimized. In other cases the cells tissues and organs may ultimately derive from an individual who is related to the recipient, or an individual who is unrelated to the recipient but matches one or more HLA haplotype markers. In still other cases, iPSCs or iMSCs or differentiated cells and tissues thereof derive from an individual with no known relationship to the recipient. Furthermore, because a donated sample becomes a good source of stem cells and differentiated tissue, a regenerative medicine business or stem cell technology (SCT) business based on iSC technology may either its store large quantities of such cells. The business may also generate a catalogue or database of biological material, which would, among other things, contain information regarding the samples, such as quantity, lot number, and the like, and also would contain identifying information and other relevant information relating to the samples. Often, such cells may be annotated with identifying information related to the donor of the sample or intended recipient, as further described herein.

The methods described herein also allow the use of iSCs (e.g., iPSCs or iMSCs) to generate material for research and development purposes or for further study or analysis. Currently, potential therapeutic compounds are typically tested against immortal cell lines, or animal models due to the unavailability of large numbers of reproducible primary human cells and tissues. These immortal cell lines and animal models significantly differ from true human model systems, and the results may not correlate with the outcome of clinical trials. This greatly increases the cost of developing new drugs and therapeutics as well as the time required. For example, a researcher studying liver toxicity of a number of compounds may wish to test these compounds on a human primary liver cell line. It would be advantageous for the researcher to test many cell lines derived from different individuals because they may exhibit differing sensitivity to the compounds due to the varying genetic background of the individual donors. Unfortunately, primary cell lines have a limited replication potential. Therefore, only a limited number of compounds can be tested on a given cell line, and each test can only be replicated a limited number of times.

The methods of the present invention allow large-scale and perhaps even unlimited generation of primary human cells and tissues from specific individuals. Therefore, panels of standardized or nonstandardized primary human cell lines, tissues, and organs can be generated from donor samples. These panels can be used as a platform to test a large, even massive, number of compounds, drugs, or potential therapeutics. Such panels may enable the generation of reproducible results on the efficacy and toxicity of potential therapeutics, in the context of the variable genetic background of the human population, in a manner that may be currently impractical. In some cases, the panels are generated from random donor samples. In other cases, the panels are categorized by some criteria such as age, sex, race, genetic background, genomic profile, disease state, or gene expression profile.

FIG. 1 illustrates the initial steps of the business methods herein. As shown in FIG. 1, biological material may be stored at any point during the process of running the regenerative medicine business (or stem cell technology business) from storage of the donor sample (100), storage of expanded somatic cells (110), storage of iSCs (e.g., iPSCs or iMSCs) (120), storage of expanded induced cells (e.g., iPSCs or iMSCs) (130), and storage of differentiated cells, tissues or organs (140). This may reduce the time required to generate the desired material for a client or individual. This process may also improve the generation of iSCs (e.g., iPSCs or iMSCs) and products derived thereof.

Figure 2:
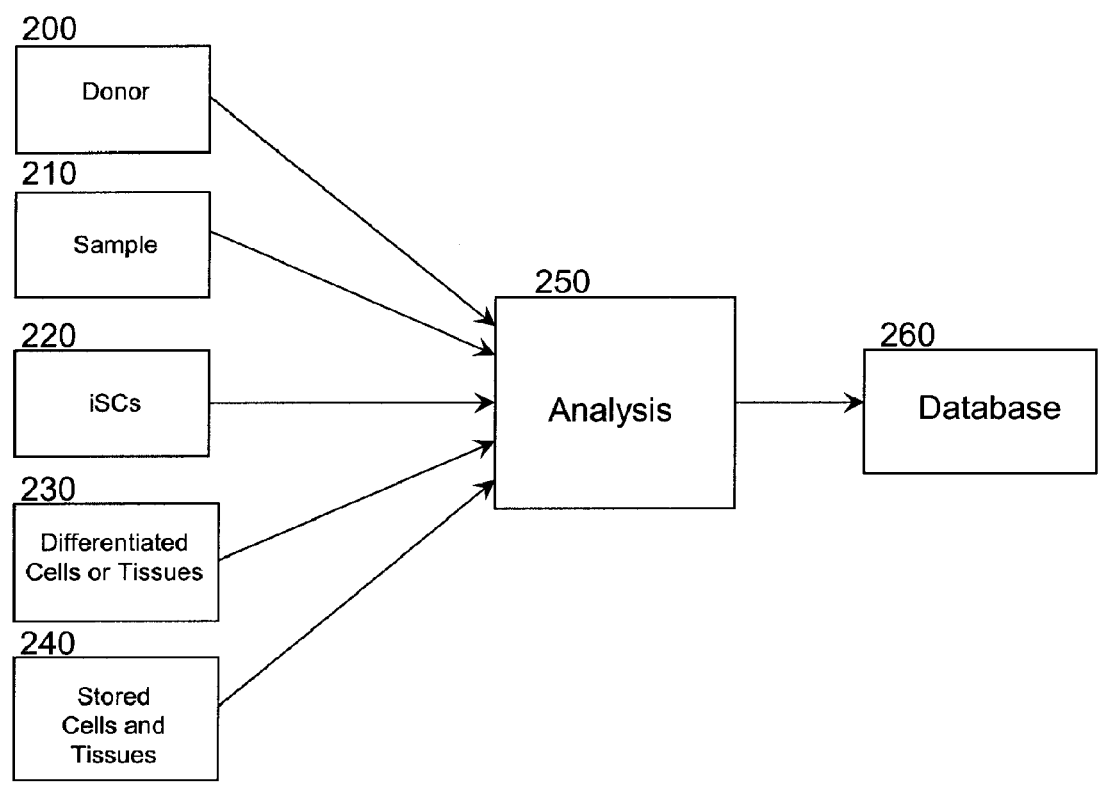
FIG. 2: is an overview of the information contained in a database constructed by the regenerative medicine business.

FIG. 2 illustrates the use of sample analysis and database construction for a regenerative medicine business or other business based on iSC (e.g., iPSCs or iMSCs) technology. As shown in FIG. 2, information concerning donors, clients, patients and samples may be stored in a database or set of databases. This information can include but is not limited to donor information, client information, physician information, and sample information. As also shown in FIG. 2, donors, clients, and samples may be analyzed to extract out information (250) and this information may be used to populate the database (260). For example, a donor's age, sex, disease state, and genomic profile may be determined and stored in the database. Similarly, the location, storage date, HLA-type, gene expression profile, cell type, and sample history may be determined and stored in the database.

Figure 3:
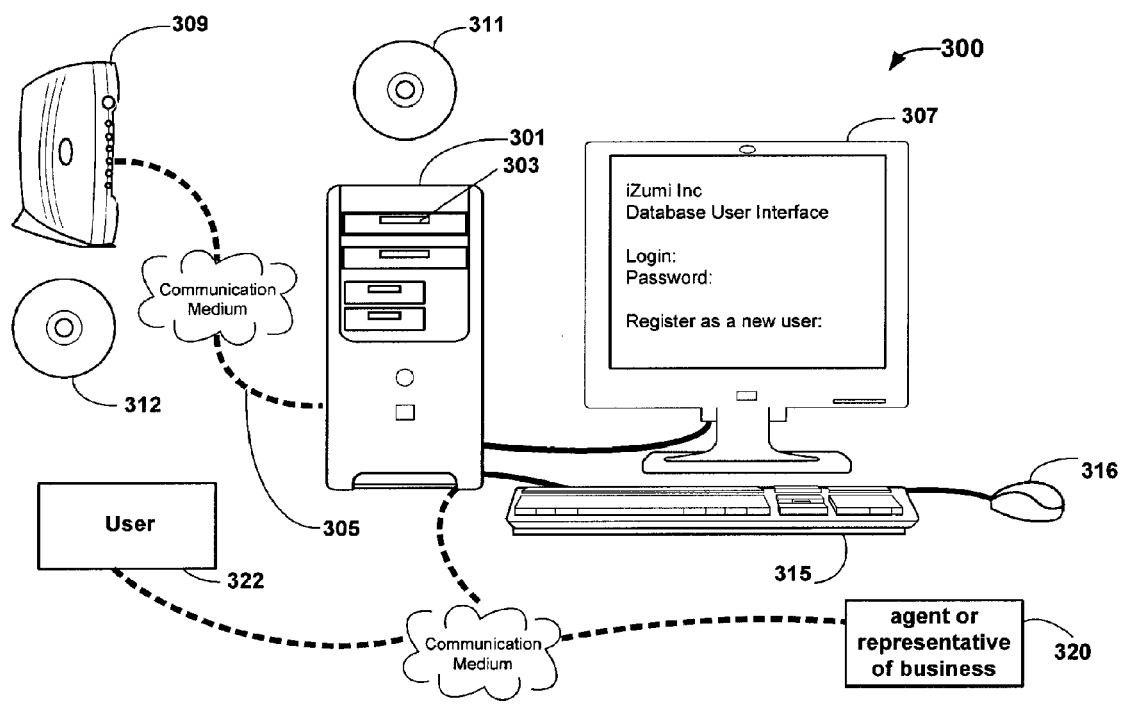
FIG. 3: is an example of accessing the database of the regenerative medicine business to obtain samples.

FIG. 3 illustrates an example of the database user interface of the present invention. In this example, the user interface resides on a computer (301), which may have a standard visual display (307) and keyboard (315) and mouse inputs (316). In some examples, the input may be by the route of pushing regions or spots on a touch screen. In some cases, the database may reside on the same computer as the user interface (301) as fixed or removable media (including computer-readable media) (311), or on a separate computer or server (309). A client (322) or representative of the business (320) may utilize this user interface to access the database through a communication medium such as a computer network. Search criteria may be input using mouse and keyboards. Search queries may be transmitted to the database, and the results displayed visually (307). In one embodiment of the user interface, results may be further narrowed by including additional or alternative search criteria.

Figure 4:
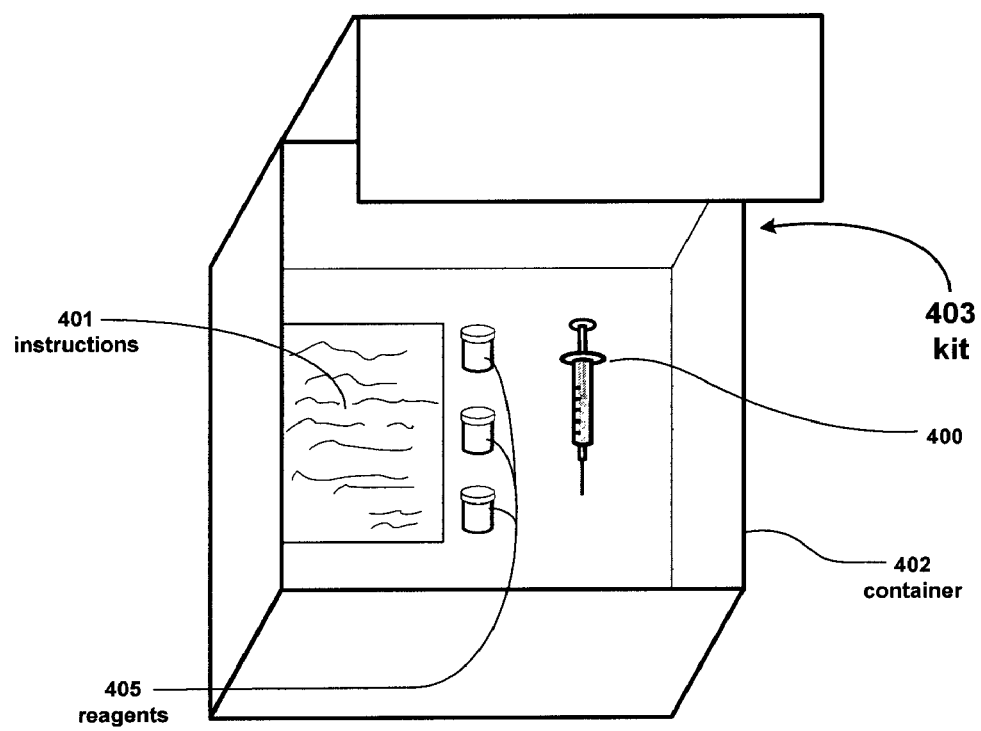
FIG. 4: is an example of a kit provided by the regenerative medicine business.

FIG. 4 illustrates a kit or kits supplied by the regenerative medicine business (or stem cell technology business). In one embodiment, the kit includes a means for sample acquisition, storage and transport. In one example of this embodiment, a sample is obtained via scraping of the dermal layer of an individual using item 400. In another example, item 400 is a finger pricking device. The sample may then be contacted with reagents (405) for storing sample in a manner compatible with the methods of the regenerative medicine business or stem cell technology business herein. Reagents anticipated in 405 include but are not limited to heparin, phytohemagglutinin, glycerol, human or animal serum, serum substitute, cell growth medium, buffers, or any reagent which allows the preservation of at least one living somatic cell from the sample. The kit further includes a set of instructions (401) for sample kit use including instructions for acquiring sample, instructions for contacting sample with storage reagents, instructions for storing sample, and instructions for transporting a sample to a storage facility.

In another embodiment of FIG. 4, the kit includes a means of generating and optionally storing or differentiating iSCs (e.g., iPSCs or iMSCs) from somatic cells. Said kit includes containers containing reagents (405) including but not limited to for example one or more of the following: plasmids or purified virus suitable for generation of iSCs (e.g., iPSCs or iMSCs); transfection reagents; somatic cells; suitable cell culture reagents such as media, and antibiotics; and reagents for differentiating iSCs (e.g., iPSCs or iMSCs) into desired cell types. Said kit also includes instructions (401) for use of the kit.

In another embodiment of FIG. 4, the kit includes containers containing differentiated cells, tissues, iPSCs, or iMSCs of the present invention (405), a means for administering the cells to an individual (400), and instructions for use of the kit (401).

II. Sample

The method of running a regenerative medicine business using iPSC technology, or other stem cell technology business, may begin with acquiring biological material in the form of living somatic cells or tissue. The present disclosure makes use of the word sample to refer to the biological material acquired from a donor or any cells, iSCs, iPSCs, iMSCs, or tissues derived thereof.

A. Sample Donor

Potential sample donors of the present invention include any animal. The term animal includes any mammal such as primates, rodents, dogs, pigs, cows, sheep, horses, rabbits, and cats. In a preferred embodiment, potential sample donors include humans. Potential sample donors of the present invention are further described in U.S. application Ser. No. 12/157,967, filed Jun. 13, 2008; First Inventor Kazuhiro Sakurada, filed Jun. 12, 2009, both of which are hereby incorporated by reference in their entirety.

The donor may be requested or required to allow the regenerative medicine business or stem cell technology business the right to sell or provide in whole or in part the donor's samples or derivatives thereof to other customers of the business. A donor may further be requested or required to allow marketing of the donor's samples or derivatives thereof. A donor who does not wish to relinquish ownership or marketing rights to his biological sample may be required to pay an increased fee for the products or services of the business. In some cases, the regenerative medicine business, or stem cell technology business, may provide a monetary incentive for donors to provide material to other clients in the form of profit sharing, credit for future services, or a fee for use of material.

B. Sample Type

The method of running a regenerative medicine business or stem cell technology business may require obtaining living cells. Some preferred embodiments include somatic cells. Examples of somatic cells include, but are not limited to fibroblasts, bone marrow-derived mononuclear cells, skeletal muscle cells, adipose cells, peripheral blood mononuclear cells, macrophages, hepatocytes, keratinocytes, oral keratinocytes, hair follicle dermal cells, gastric epithelial cells, lung epithelial cells, synovial cells, kidney cells, skin epithelial cells or osteoblasts. It is further understood that cells such as red blood cells and platelets that lack a nucleus and are thus unable to replicate are unsuitable for the methods of the present invention. In some cases the donor sample is not a partially, wholly, or substantially purified hematopoietic stem cell. Methods and related compositions for collection of biological material suitable for running a regenerative medicine business based on iSC (e.g., iPSC or iMSC) technology or other stem cell technology business are further described in U.S. application Ser. No. 12/157,967, filed Jun. 13, 2008; First Inventor Kazuhiro Sakurada, which is hereby incorporated by reference.

Since environmentally induced mutations in somatic cells are present at low rates in young individuals, preferred biological material for the cell bank are cord blood, the umbilical cord, the placenta, amniotic fluid, and neonatal tissues such as bone marrow, muscle, and blood.

In some embodiments, the sample is an amount of blood from a donor from about 500 ml to about 1 ul including the range from 400 ml to 5 ul, 200 ml to 5 ul, 100 ml to 5 ul, 50 ml to 5 ul, 25 ml to 5 ul, 10 ml to 5 ul, and 1 ml to 5 ul including about 5 ul, 10 ul, 20 ul, 50 ul, 100 ul, 200 ul, 400 ul, 500 ul, 1 ml, 2 ml, 5 ml, 10 ml, 20 ml, 50 ml, 100 ml, and 200 ml. In an exemplary embodiment, the sample is blood from a finger prick. In other embodiments the sample is from bone marrow, skin, muscle, adipose tissue, peripheral blood, foreskin, skeletal muscle, or smooth muscle.

C. Sample Source and Acquisition

Sample acquisition may be performed by an employee, representative, or agent of the regenerative medicine business or stem cell technology business. For example, a donor may visit the location of the business and provide a biological sample as described herein. The employee, representative, or agent may be a nurse, doctor, genetic counselor, medical technician, customer service representative, sales representative or any other employee or agent of the business. The present invention refers to the terms employee, agent, or representative as equivalent terms to be used interchangeably.

An agent of the regenerative medicine business or stem cell technology business may perform the sample acquisition at the residence of the donor or at a third party location such as a clinic, a fertility clinic, a health spa, a doctor's office, a health fair, a blood mobile, or any other location in which the donor may wish to provide a sample such as the donor's residence. In other cases sample acquisition may be performed by a third party such as a family physician, genetic counselor, other medical professional, sales representative, family member, or any other third party. In still other cases the sample acquisition may be performed by an employee or agent of a third party business or concern including but not limited to an agent or representative of a health spa, a cell banking facility, a fertility clinic, a clinic, a hospital, a blood bank, or a cord blood bank. It is also understood that the sample may or may not have originally been obtained for the purpose of using the services of the regenerative medicine business or stem cell technology business described herein.

The third party may or may not perform the sample acquisition using a kit provided or sold by the regenerative medicine business, stem cell technology business a medical supplier, pharmacy, or store. The third party may acquire the sample at a place of business, or at the residence of the donor or at any other location. Similarly, sample acquisition may be performed by the donor at any location. The donor may or may not perform the sample acquisition using a kit provided by the regenerative medicine business or stem cell technology business. Such a kit may be sold to the donor through a third party such as a store, a pharmacy, a doctors office or any third party licensed to sell a kit for obtaining a sample intended for use by a regenerative medicine business using iPSC technology or other stem cell technology business.

The act of accepting a sample can be understood to mean the physical act of taking possession of the sample by either the regenerative medicine business, stem cell technology business, or by a third party such as a cell-banking facility, medical professional, a fertility clinic, a clinic, a hospital, a blood bank, or a cord blood bank.

The biological sample may be acquired, stored, and transported to the regenerative medicine business, stem cell technology business, or a third party. The sample must be acquired stored and transported in a manner that preserves the viability of at least one cell but preferably all the cells in the sample, including any range between one cell and all cells in the sample. Methods for storage and transport of the sample are known in the art and may include placing the sample in a suitable growth or homeostasis inducing medium, or storing the sample in a cryogenic state. In some cases, blood samples are contacted with phytohemagglutinin or heparin or both prior, during or after storage. The somatic cells may also be provided as cryopreserved compositions containing a cryopreservation medium and a population of human somatic cells, from a third party cell-banking facility or a fertility clinic. Methods for acquiring, storing, and transporting suitable samples are described in U.S. application Ser. No. 12/157,967, filed Jun. 13, 2008; First Inventor Kazuhiro Sakurada, which is hereby incorporated by reference in its entirety.

The methods of storage may be any method including the methods described herein, e.g., using cryopreservation medium. Some exemplary cryopreservation media include the "Cryopreservation Medium For Primate ES Cells" (ReproCELL, Tokyo, Japan) or mFreSR™ (StemCell Technologies, Vancouver, Calif.). The cells preferably are rapidly frozen in liquid nitrogen, and stored in a liquid nitrogen storage vessel. Other suitable cryopreservation media and methods for cryopreservation/thawing of cells generated by the methods described herein are provided in, e.g., U.S. patent application Ser. Nos. 10/902,571 and 11/142,651. See also, Ha et al., (2005), Hum. Reprod., 20(7):1779-1785; and U.S. application Ser. No. 12/157,967, filed Jun. 13, 2008; First Inventor Kazuhiro Sakurada, all of which are incorporated by reference in their entirety.

D. Sample Storage

The regenerative medicine business or stem cell technology business described in the present disclosure may store samples for use by donors and other potential customers. It is understood that biological samples, tissues, or cells may be stored at any point in the process of running the business. For example: samples may be stored immediately upon acquisition; after expansion of somatic cells, iSCs, iPSCs, or differentiated cells; after generation of iSCs or iPSCs; after differentiation of iSCs or iPSCs; or after generation of differentiated tissues.

Biological samples can be stored in any manner that allows maintenance of the sample in a manner suitable for generation of iPSCs. Cells and tissues can be stored in any manner that is compatible with the methods of running a regenerative medicine business or stem cell technology business. For example the sample, or cells isolated from the sample, can be cryopreserved directly after receipt or acquisition of the sample by the methods described in the present disclosure. In other cases, cells are stored in an incubator or maintained by culturing.

The samples may or may not be stored directly at the business location or by an employee or agent of the business. Samples may be stored by a third party including but not limited to: a clinic, a fertility clinic, a hospital, a cell-banking facility, a cord-blood bank, a blood bank, a physician, or any entity capable of storing samples suitable for the regenerative medicine business or stem cell technology business. For example, the sample may be 1) acquired by the donor using a kit supplied by the regenerative medicine business or stem cell technology business and sold through an intermediary such as a pharmacy 2) shipped to a third party cell-banking facility, researcher, or medical professional, and 3) cryogenically preserved upon receipt of the sample by the cell-banking facility, researcher, or medical professional. In some cases, the somatic cells are expanded, ex vivo, prior to cryopreservation. In other cases the somatic cells are expanded after cryopreservation. Suitable methods and reagents for storage or cryopreservation of cells or tissues for running a regenerative medicine business based on iPSC technology (as well as iSC or iMSC technology) or stem cell technology business are described in U.S. application Ser. No. 12/157,967, filed Jun. 13, 2008; First Inventor Kazuhiro Sakurada, which is hereby incorporated by reference. In some cases, the donor or payee may be billed for sample acquisition and or storage. The payee can include but is not limited to a customer of the business, a physician, an insurance provider, a non profit group, or a government entity such as Medicaid.

III. Donor and Sample Analysis

The regenerative medicine business or other stem cell technology business may analyze one or more of the following: donors, samples, customers, and potential customers. The results of these analyses may be used to populate a database or set of databases for use by the business, donors, customers, potential customers, or third parties. The donor, customer, or potential customer may be analyzed to obtain identifying information such as the name, social security number, age, race, ethnicity, gender, national origin, disease-status of the donor or diseases for which the donor may be pre-disposed.

Methods of determining susceptibility to diseases or conditions by examining genomic or gene expression data are provided in U.S. application Ser. No. 12/157,967, filed Jun. 13, 2008; First Inventor Kazuhiro Sakurada, filed on Jun. 13, 2008; First Inventor Kazuhiro Sakurada, which is hereby incorporated by reference.

Exemplary diseases or conditions the donor may suffer or be anticipated to suffer include but are not limited to: neurodegenerative disorders; neurological disorders such as stroke, cognitive impairment, and mood disorders; auditory disease such as deafness; osteoporosis; cardiovascular diseases; diabetes; metabolic disorders; respiratory diseases; drug sensitivity conditions; eye diseases such as macular degeneration; immunological disorders; hematological diseases; kidney diseases; proliferative disorders; genetic disorders, traumatic injury, stroke, organ failure, or loss of limb.

Examples of neurodegenerative disorders include, but are not limited to, Alexander's disease, Alper's disease, Alzheimer's disease, amyotrophic lateral sclerosis, ataxia telangiectasia, Batten disease, bovine spongiform encephalopathy, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, prion diseases, Refsum's disease, Sandhoffs disease, Schilder's disease, subacute combined degeneration of spinal cord secondary to pernicious anaemia, schizophrenia, spinocerebellar ataxia, spinal muscular atrophy (SMA), Steele-Richardson-Olszewski disease, and tabes dorsalis.

Examples of immunological disorders include but are not limited to acquired immune deficiency, leukemia, lymphoma, hypersensitivities (allergy), autoimmune diseases, and severe combined immune deficiency.

Examples of autoimmune diseases include but are not limited to acute disseminated encephalomyelitis, addison's disease, ankylosing spondylitis, antiphospholipid antibody syndrome, autoimmune hemolytic anemia, autoimmune hepatitis, bullous pemphigoid, coeliac disease, dermatomyositis, diabetes mellitus type 1, diabetes mellitus type 2, Goodpasture's syndrome, Graves' disease, Guillain-Barrè syndrome, Hashimoto's disease, idiopathic thrombocytopenic purpura, lupus erythematosus, multiple sclerosis, myasthenia gravis, pemphigus, pernicious anaemia, polymyositis, primary biliary cirrhosis, rheumatoid arthritis, Sjögren's syndrome, temporal arthritis (also known as "giant cell arthritis"), vasculitis, Wegener's granulomatosis.

Examples of cardiovascular diseases include but are not limited to aneurysm, angina, arrhythmia, atherosclerosis, cardiomyopathy, calcific aortic valve disease (CAVD), cerebrovascular accident (stroke), cerebrovascular disease, congenital heart disease, congestive heart failure, myocarditis, valve disease coronary, artery disease dilated, cardiomyopathy, diastolic dysfunction, endocarditis, high blood pressure (hypertension), hypertrophic cardiomyopathy, mitral valve prolapse, myocardial infarction (heart attack), and venous thromboembolism.

Examples of metabolic disorders include but are not limited to acid lipase disease, amyloidosis, Barth Syndrome, biotinidase deficiency, carnitine palmitoyl transferase deficiency type II, central pontine myelinolysis, metabolic diseases of muscle including muscular dystrophy, Farber's Disease, glucose-6-phosphate dehydrogenase deficiency, gangliosidoses, trimethylaminuria, Lesch-Nyhan syndrome, lipid storage diseases, metabolic myopathies, methylmalonic aciduria, mitochondrial myopathies, mucopolysaccharidoses, mucolipidoses, mucolipidoses, mucopolysaccharidoses, multiple CoA carboxylase deficiency, nonketotic hyperglycinemia, Pompe disease, propionic acidemia, type I glycogen storage disease, urea cycle disorders, hyperoxaluria, and oxalosis.

Examples of proliferative disorders include but are not limited to one or more of the following: carcinomas, sarcomas, lymphomas, leukemias, germ cell tumors, blastic tumors, prostate cancer, lung cancer, colorectal cancer, bladder cancer, cutaneous melanoma, breast cancer, endometrial cancer, and ovarian cancer.

Further examples of diseases or disorders may be found in U.S. application Ser. No. 12/157,967, filed Jun. 13, 2008; First Inventor Kazuhiro Sakurada, filed on Jun. 13, 2008; First Inventor Kazuhiro Sakurada, all of which are hereby incorporated by reference. It is also anticipated that the methods of the present invention include marketing and selling products and services for the treatment of diseases and disorders including, but not limited to, those mentioned herein.

Susceptibility or pre-disposition to a disease or condition may be determined by examining factors other than genomic or gene expression data. These factors include but are not limited to one or more of the following: engaging in dangerous activities such as smoking, scuba diving, or rock climbing for example; family history such as a history of obesity, drug dependence, depression, diabetes, or other diseases or conditions that are known to occur or have occurred in related family members; and medical history. In some cases, the donor is analyzed for the presence of cytomegalovirus specific antibodies (CMV serologic status).

The database may also contain or include other identifying information of the stored tissue or cells. For example, the identifying information may be a molecular profile, or set of molecular profiles. The term molecular profile is understood to mean partial, whole, or substantially-whole genomic profiles, e.g., genome sequences, SNP, CNV, VNTR, or InDel profiles, gene expression profiles, or protein expression profiles. Methods and compositions for determining and analyzing molecular profiles are provided in U.S. application Ser. No. 12/157,967, filed Jun. 13, 2008; First Inventor Kazuhiro Sakurada, filed on Jun. 12, 2009; First Inventor Kazuhiro Sakurada, both of which are hereby incorporated by reference in their entirety.

The identifying information may include cell-type, tissue type, and sample history. Sample history may include date of sample acquisition; method of sample acquisition; origin of sample; number of times sample has been sub-cultured; method of storage; date of storage; length of time sample has been stored; derivatives of the sample; history of derivatives of the sample; customers or third parties that have requested or received samples or derivatives thereof; customers or third parties that have been billed or paid for samples; derivatives, or services rendered; and manipulations performed on the sample. Manipulations performed on the sample may include, but are not limited to, expansion, storage, generation of iPSCs, iSCs or differentiation of iPSCs or iSCs.

Donated cells or tissue, or derivatives thereof, may analyzed prior to or after storage. The biological sample may be assayed by a number of methods known to the art, including but not limited to: molecular profiling, gene expression analysis; whole or partial genomic sequencing; protein expression analysis; determination of the HLA serotype or genotype; SNP, VNTR, CNV, or InDel profiling; analysis of methylation patterns; karyotype analysis; or analysis of malignant or premalignant changes. In some cases, the sample may be assayed for the presence of viral, fungal, or bacterial contamination. The results of these analyses may be included as information in the database.

Assays may be performed after manipulation of the sample such as generation of iPSCs (or iSCs), or differentiation. In some cases assays are performed both before and after manipulation of the sample. It is also understood that for some analyses, analysis of the sample and analysis of the donor are equivalent. In some cases, the donor, a third party, or payee thereof may be billed for the analyses of the cells, tissues, or donors of the present disclosure. The assays may also be performed by a third party such as a cell banking facility, physician, hospital, clinical laboratory, laboratory, contract research organization, or other testing facility.

Samples, or derivatives thereof such as iPSCs may also be analyzed for markers of pluripotency, multipotency or embryonic stem cell markers. Such markers are known to the art and are described in U.S. application Ser. No. 12/157,967, filed Jun. 13, 2008; First Inventor Kazuhiro Sakurada, which is herein incorporated by reference in its entirety. It is further understood that new markers may become known to the art and that the methods of the present invention also apply to such new markers.

The donor, samples or derivatives thereof may be analyzed for malignant or pre-malignant changes. Such changes are known to the art and include but are not limited to one or more of the following: aberrant expression or mutations in p53, Ki67, ras, cox-2, bcl-2, or any gene that contributes to progression towards malignancy; and morphological changes. Analysis for such changes may include comparison of genomic or gene expression data to a database of known markers of malignancy, pre-malignancy, proliferative disorders, or other diseases or conditions including but not limited to the disease to gene expression mapper database (http://dgem.cs.iupui.edu), and the online mendelian inheritance in man database (www.ncbi.nlm.nih.gov/omim/). It is understood that the number of known markers of malignancy and pre-malignancy is increasing, and the methods of the present invention are expected to also apply to markers that are not currently known to the art, but that are later discovered or made known.

In some embodiments, iPSC technology may be used to provide personalized guidance for therapeutic interventions. Samples, or cells or tissues derived thereof may be analyzed by determining a dose response, inhibitory concentration, effective concentration, maximum tolerated dose, or lethal dose for a given therapeutic agent on a cellular phenotype for a given individual. For example, an individual may be diagnosed with a proliferative disorder such as hepatocellular carcinoma. The individual may provide a sample to the regenerative medicine business, stem cell technology business or a third party. Said sample may be used to generate heptocytes. Said hepatocytes may then be used to screen compounds or therapeutic agents for toxicity, or inhibition of proliferation.

In some embodiments the regenerative medicine business or stem cell technology business may provide iPSCs, iMSCs, differentiated cells, or tissues to subjects other than, or even unrelated to the original donor. In such cases, it may be advantageous to determine the compatibility between a donor's sample and a subject. In order to determine compatibility, samples and subjects may be analyzed for human leukocyte antigen (HLA) type.

HLA-type refers to the unique set of proteins called human leukocyte antigens. These proteins are present on each individual's cells and allow the immune system to recognize 'self' from 'foreign'. Administration of cells or tissues that are recognized as foreign can lead to compatibility problems such as immuno-rejection or graft versus host disease (GVHD). Accordingly, HLA type is particularly important in organ and tissue transplantation.

There are six major HLAs (HLA-A, HLA-B, HLA-C, HLA-DR, HLA-DP, and HLA-DQHLA). Each HLA antigen has multiple isoforms in the human population, and each individual can have two different isoforms for each HLA due to the diploid nature of our genome. Therefore, a perfect match would match twelve out of twelve isoforms. A cell or tissue donated from the same individual as, or an identical twin of, the intended recipient would have a perfect HLA-type and is referred to as allogenic or autologous. It is also understood that certain factors including but not limited to ethnic background and race correlate with certain HLA-types.

Many major and minor HLA isoforms exist and it is understood that a suitable match may include a match between a subset of the major HLAs, all the major HLAs, some or all major and minor HLAs or any combination known to the art that mitigates immuno-rejection or GVDH. It is also understood that specific guidelines for what constitutes a good HLA-type match depends on many factors. Therefore, judgment must be made by one skilled in the art to assess the suitability of a given cell or tissue sample for transplant into a given individual.

HLA-type can be determined using so-called low resolution methods, for example by sero-typing, or using antibody based methods. Sero-typing is based on antibody recognition of HLA-types. Sero-typing can distinguish between 28 different HLA-A genes, 59 HLA-B genes and 21 HLA-C genes. A perfect match by sero-typing methods would be a so-called six out of six match referring to the two alleles for each HLA (A,B, and C) present in each individual. In certain cases, a five out of six match or less may be considered a good match as determined by one skilled in the art.

Other low or medium resolution methods to determine HLA-type examine the HLA isoforms of the individual, but do not rely on determining the actual sequence of an individual's HLA alleles. Often, the donor is related to the individual receiving the sample, in this case sero-typing alone or in combination with other low or medium resolution methods may be sufficient to determine if a sample is suitable for transplantation. In other cases a five out of six or lower match is readily found, but a perfect match is not. In such cases it may be advantageous to use cells or tissues with a lower match rather than expend time and effort to find a better HLA-type match.

High resolution methods involve examining the specific sequence of the HLA genes or gene expression products (protein or RNA). High resolution methods can distinguish between thousands of different isoforms. Due to the time and expense of performing high-resolution HLA-typing, it may or may not be desirable to perform this analysis until such time as it is deemed necessary to confirm a suitable match. For example, an individual may search the database of the regenerative medicine business or stem cell technology business and find 1000 suitable perfect sero-typed HLA matches. In this example, 1000 samples would be very expensive to test for high resolution HLA-type. However, these matches may be further grouped by geographic location of the donor, age, sex, race, ethnic background or any other criteria that increases the likelihood of a high resolution HLA-type match (e.g. ethnic background), or increases the desirability of the sample (e.g. a young donor age). The 1000 samples from the original search may thus be narrowed down to a few likely candidates suitable for high resolution HLA-typing. HLA-typing may then be performed by the regenerative medicine business, stem cell technology business or a third party.

IV. Sample Manipulation

A. Cell Culture

The methods of the present invention include culturing of cells from donor samples. These cells include somatic cells obtained from donors, iPSCs generated from these somatic cells, and differentiated cells generated from the iPSCs. Detailed methods of cell culture suitable for running a regenerative medicine business based on iSC technology or stem cell technology business or other stem cell technology business are described in application U.S. application Ser. No. 12/157,967, filed Jun. 13, 2008; First Inventor Kazuhiro Sakurada, which is herein incorporated by reference in its entirety. Tissues, cell, or iSCs (e.g., iPSCs or iMSCs) may be cultured or expanded at any point during the process of running the regenerative medicine business or other stem cell technology business prior to, or after storage. Methods incorporated by reference include methods for obtaining and culturing cells from bone marrow, skin, skeletal muscle, adipose tissue, and blood.

B. Induction

Methods for generation of iPSCs from somatic cells involves forced expression of a set of polypeptides or induction factors (IFs). IFs currently known to the art include but are not limited to polypeptides encoded by the genes: c-Myc, Oct3/4, Sox2, and Klf4. In addition, small molecule compounds such as histone deacetylace inhibitors may be used or a combination of IFs and small molecules may be used to generate iPSCs. The somatic cells may be used directly, i.e., without culturing or passaging, in the referenced induction methods; or, the somatic cells may be cultured and/or passaged prior to their use in the referenced induction methods. The induced cells may be induced from the somatic cells of a postnatal donor or non-embryonic donor as described in U.S. application Ser. No. 12/157,967, filed Jun. 13, 2008; First Inventor Kazuhiro Sakurada, which is herein incorporated by reference in its entirety. The induced stem cells may be generated from any cell-type including but not limited to those described.

IPSCs or iSCs may be used directly for differentiation or regenerative medicine. In other cases, iPSCs or iSCs may be stored by the regenerative medicine business, stem cell technology business or a third party. Alternatively, iPSCs or iSCs may be expanded using culturing methods described in U.S. application Ser. No. 12/157,967, filed Jun. 13, 2008; First Inventor Kazuhiro Sakurada, which is herein incorporated by reference in its entirety, prior to or after storage. iSCs may be stored in any manner which preserves their multipotent or pluripotent capabilities including cryogenic storage, and culturing. In some cases the donor, potential recipient of the iPSCs or derivatives thereof, or payee may be billed for generation and or delivery of iPSCs or differentiated cells or tissues. In some cases a kit may be marketed and sold which includes a means for generation of iPSCs.

During the induction process, forced expression of certain polypeptides is carried out in cultured cells for a period of time, after which the induced cells are screened for a number of morphological and gene expression properties that characterize multipotent and pluripotent stem cells. Induced cells that meet these screening criteria may then be subcloned and expanded. In some cases, the cells to be induced may be cultured for a period of time prior to the induction procedure. Alternatively, the cells to be induced may be used directly in the induction process without a prior culture period. In some embodiments, the type of cell culture medium used is the same or very similar before, during, and after the induction process. In other cases, different cell culture media are used at different points. For example, one type of culture medium may be used directly before the induction process, while a second type of media is used during the induction process. At times, a third type of culture medium is used during the induction process.

Cells may be cultured in medium supplemented with a particular serum. In some embodiments, the serum is fetal bovine serum (FBS). The serum can also be fetal calf serum (FCS). In some cases, the serum may be Human AB serum. Mixtures of serum may also be used, e.g. mixture of FBS and Human AB, FBS and FCS, or FCS and Human AB.

Culture of cells may be carried out under a low serum culture conditions prior to, during, or following induction. A "low serum culture condition" refers to the use of a cell culture medium containing a concentration of serum ranging from 0% (v/v) (i.e., serum-free) to about 5% (v/v), e.g., 0% to 2%, 0% to 2.5%, 0% to 3%, 0% to 4%, 0% to 5%, 0.1% to 2%, 0.1% to 5%, 0.1%, 0.5%, 1%, 1.2%, 1.5%, 2%, 2.5%, 3%, 3.5%, or 4%. In some embodiments, the serum concentration is from about 0% to about 2%. In some cases, the serum concentration is about 2%. In some cases, the serum concentration is preferably 2% or less. In other embodiments, cells are cultured under a "high serum condition," i.e., greater than 5% serum to about 20% serum, e.g., 6%, 7%, 8%, 10%, 12%, 15%, or 20%. Culturing under high serum conditions may occur prior to, during, and/or after induction.

Some representative media that the cells can be cultured in include: MAPC, FBM, ES, MEF-conditioned ES (MC-ES), and mTeSR™ (available, e.g., from StemCell Technologies, Vancouver, Canada), See Ludwig et al (2006), Nat Biotechnol, 24(2):185-187. In other cases, alternative culture conditions for growth of human ES cells are used, as described in, e.g., Skottman et al (2006), Reproduction, 132(5):691-698. In some embodiments, the cells are cultured in MAPC, FBM, MC-ES, or mTeSR™ prior to and/or during the introduction of induction factors to the cells; and the cells are cultured in MC-ES or mTeSR™ medium later in the induction process.

MAPC (2% FBS) Medium may comprise: 60% Dulbecco's Modified Eagle's Medium-low glucose, 40% MCDB 201, Insulin Transferrin Selenium supplement, (0.01 mg/ml insulin; 0.0055 mg/ml transferrin; 0.005 µg/ml sodium selenite), 1× linolenic acid albumin (1 mg/mL albumin; 2 moles linoneic acid/mole albumin), 1 nM dexamethasone, 2% fetal bovine serum, 1 nM dexamethasone, 10-4 M ascorbic acid, and 10 pg/ml gentamycin.

FBM (2% FBS) Medium may comprise: MCDB202 modified medium, 2% fetal bovine serum, 5 µg/ml insulin, 50 mg/ml gentamycin, and 50 ng/ml amphotericin-B.

ES Medium may comprise: 40% Dulbecco's Modified Eagle's Medium (DMEM) 40% F12 medium, 2 mM L-glutamine, 1× non-essential amino acids (Sigma, Inc., St. Louis, Mo.), 20% Knockout Serum Replacement™ (Invitrogen, Inc., Carlsbad, Calif.), and 10 µg/ml gentamycin.

MC-ES medium may be prepared as follows. ES medium is conditioned on mitomycin C-treated murine embryonic fibroblasts (MEFs), harvested, filtered through a 0.45-µM filter, and supplemented with about 0.1 mM β mercaptoethanol, about 10 ng/ml bFGF or FGF-2, and, optionally, about 10 ng/ml activin A. In some cases, irradiated MEFs are used in place of the mitomycin C-treated MEFs.

When either low or high serum conditions are used for culturing the cells, one or more growth factors such as fibroblast growth factor (FGF)-2; basic FGF (bFGF); platelet-derived growth factor (PDGF), epidermal growth factor (EGF); insulin-like growth factor (IGF); or insulin can be included in the culture medium. Other growth factors that can be used to supplement cell culture media include, but are not limited to one or more: Transforming Growth Factor □-1 (TGF □-1), Activin A, Noggin, Brain-derived Neurotrophic Factor (BDNF), Nerve Growth Factor (NGF), Neurotrophin (NT)-1, NT-2, or NT 3. In some cases, one or more of such factors is used in place of the bFGF or FGF-2 in the MC-ES medium or other cell culture medium.

In some cases, the concentration of growth factors in the culture media described herein (e.g., MAPC, FBM, MC-ES, mTeSR™) is from about 2 ng/ml to about 20 ng/ml, e.g., about 2 ng/ml, 3 ng/ml, 4 ng/ml, 5 ng/ml, 6 ng/ml, 7 ng/ml, 8 ng/ml, 10 ng/ml, 12 ng/ml, 14 ng/ml, 15 ng/ml, 17 ng/ml, or 20 ng/ml. In some embodiments, the concentration of bFGF or FGF2 is from about 2 ng/ml to about 5 ng/ml; from about 5 ng/ml to about 8 ng/ml; from about 9 ng/ml to about 11 ng/ml; from about 11 ng/ml to about 15 ng/ml; or from about 15 ng/ml to about 20 ng/ml.

The growth factors may be used alone or in combination. For example, FGF-2 may be added alone to the medium; in another example, both PDGF and EGF are added to the culture medium.

In some examples, following initiation of the forced expression of genes or polypeptides (e.g., immediately after a retroviral infection period) in cells, the "induced cells" are maintained in MC-ES medium as described herein.

In some embodiments, cells are maintained in the presence of a rho, or rho-associated, protein kinase (ROCK) inhibitor to reduce apoptosis. In some cases, an inhibitor of Rho associated kinase is added to the culture medium. For example, the addition of Y-27632 (Calbiochem; water soluble) or Fasudil (HA1077: Calbiochem), an inhibitor of Rho associated kinase (Rho associated coiled coil-containing protein kinase) may be used to culture the human pluripotent and multipotent stem cells of the present invention. In some cases the concentration of Y-27632 or Fasudil, is from about 5 µM to about 20 µM, e.g., about 5 µM, 10 µM, 15 µM, or 20 µM.

The cells may be cultured for about 1 to about 12 days e.g., 2 days, 3 days, 4.5 days, 5 days, 6.5 days, 7 days, 8 days, 9 days, 10 days, or any other number of days from about 1 day to about 12 days prior to undergoing the induction methods described herein.

In some cases, the induced cells are cultured in complete ES medium in a 37□C, 5% CO2 incubator, with medium changes about every 1 to 2 days. In some embodiments, induced the induced cells are cultured and observed for about 14 days to about 40 days, e.g., 15, 16, 17, 18, 19, 20, 23, 24, 27, 28, 29, 30, 31, 33, 34, 35, 36, 37, 38 days, or any other period from about 14 days to about 40 days prior to identifying and selecting clones comprising "induced cells" based on morphological characteristics. Morphological characteristics for identifying induced cell clones include, but are not limited to, a small cell size with a high nucleus-to-cytoplasm ratio; formation of small monolayer colonies within the space between parental cells (e.g., between fibroblasts).

The cells may be plated at a cell density of about 1×103 cells/cm2 to about 1×104 cells/cm2, e.g., 2×103 cells/cm2, 3.5×103 cells/cm2, 6×103 cells/cm2, 7×103 cells/cm2, 9×103 cells/cm2, or any other cell density from about $1 \times 10^3$ cells/cm2 to about $1 \times 10^4$ cells/cm2.

The cells can be plated and cultured directly on tissue culture-grade plastic. Alternatively, cells are plated and cultured on a coated substrate, e.g., a substrate coated with fibronectin, gelatin, matrigel™, collagen, or laminin. Suitable cell culture vessels include, e.g., 35 mm, 60 mm, 100 mm, and 150 mm cell culture dishes, 6-well cell culture plates, and other size-equivalent cell culture vessels. In some cases, the cells are cultured with feeder cells. For example, the cells may be cultured on a layer, or carpet, of MEFs.

Media with low concentrations of serum may be particularly useful to enrich for undifferentiated stem cells. The undifferentiated cells cultured under low serum conditions may or may not share certain properties with MSCs, MAPCs, and/or MIAMI cells. Differences in phenotype may be due, in part, to culture methods used to obtain MSCs, MAPCs and MIAMI cells. For example, MSCs are often obtained by isolating the non-hematopoeitic cells (e.g., interstitial cells) adhering to a plastic culture dish when tissue, e.g., bone marrow, fat, muscle, or skin etc., is cultured in a culture medium containing a high-concentration serum (5% or more). However, even under these culture conditions, a very small number of undifferentiated cells can be maintained, especially if the cells were passaged under certain culture conditions (e.g., low passage number or low-density culturing).

In some embodiments, in order to culture and grow human pluripotent stem cells induced from the undifferentiated stem cells of the present invention present in a human postnatal tissue, it is preferred that the cells are subcultured every 5 to 7 days in a culture medium containing the additives described herein on a MEF-covered plastic culture dish or a matrigel-coated plastic culture dish. In some cases, the cells may be cultured at a low density, which may be accomplished by splitting the cells from about 1:6 to 1:3 or by plating the cells at $10^3$ cells/cm$^2$ to $3 \times 10^4$ cells/cm$^2$.

Primary culture ordinarily occurs immediately after the cells are isolated from a donor, e.g., human. The primary cells can be subjected to a second subculture, a third subculture, a fourth subculture, and greater than four subcultures. A "second" subculture describes primary culture cells subcultured once, a "third" subculture describes primary cultures subcultured twice, a "fourth" subculture describes primary cells subcultured three times, etc. The culture techniques described herein may generally include culturing from the period between the primary culture and the fourth subculture, but other culture periods may also be employed. Preferably, cells are cultured from primary culture to second subculture.

Inducing a cell to become multipotent or pluripotent can be accomplished in numerous ways. In some embodiments, the methods for induction of pluripotency or multipotency in one or more cells include forcing expression of a set of induction factors (IFs). In some cases, the set of IFs includes one or more: an Oct3/4 polypeptide, a Sox2 polypeptide, a Klf4 polypeptide, or a c-Myc polypeptide. In some cases, the set does not include a c-Myc polypeptide. For example, the set of IFs can include: an Oct3/4 polypeptide, a Sox2 polypeptide, and a Klf4 polypeptide, but not a c-Myc polypeptide. In some cases, the set of IFs does not include polypeptides that might increase the risk of cell transformation.

In some cases, the set may include a c-Myc polypeptide. In certain cases, the c-Myc polypeptide is a constitutively active variant of c-Myc. In some instances, the set includes a c-Myc polypeptide capable of inducible activity, e.g., a c-Myc-ER polypeptide, see, e.g., Littlewood, et al. (1995) Nucleic Acid Res. 23(10):1686-90.

In other cases, the set of IFs may include: an Oct3/4 polypeptide, a Sox2 polypeptide, and a Klf4 polypeptide, but not a TERT polypeptide, a SV40 Large T antigen polypeptide, HPV16 E6 polypeptide, a HPV16 E7 polypeptide, or a Bmil polypeptide. In some cases, the set of IFs does not include a TERT polypeptide. In some cases, the set of IFs does not include a SV40 Large T antigen. In other cases, the set of IFS does not include a HPV 16 E6 polypeptide or a HPV 16 E7 polypeptide.

In some cases, the set of IFs includes three IFs, wherein two of the three IFs are an Oct3/4 polypeptide and a Sox2 polypeptide. In other cases, the set of IFs includes two IFs, wherein the two polypeptides are a c-Myc polypeptide and a Sox2 polypeptide In some cases, the set of induction factors is limited to Oct 3/4, Sox2, and Klf4 polypeptides. In other cases, the set of induction factors may be limited to a set of four IFs: an Oct3/4 polypeptide, a Sox2 polypeptide, a Klf4 polypeptide, and a c-Myc polypeptide.

A set of IFs may include IFs in addition to an Oct 3/4, a Sox2, and a Klf4 polypeptide. Such additional IFs include, but are not limited to Nanog, TERT, LIN28, CYP26A1, GDF3, FoxD3, Zfp42, Dnmt3b, Ecat1, and Tcl1 polypeptides. In some cases, the set of additional IFs does not include a c Myc polypeptide. In some cases, the set of additional IFs does not include polypeptides that might increase the risk of cell transformation.

Forced expression of IFs may be maintained for a period of at least about 7 days to at least about 40 days, e.g., 8 days, 9 days, 10 days, 11 days, 12 days, 13 days, 14 days, 15 days, 16 days, 17 days, 18 days, 19 days, 20 days, 21 days, 25 days, 30 days, 33 days, or 37 days.

C. Gene Therapy

Introduction of heterologous transgenes (HTs) may be used to provide a beneficial oligonucleotide, gene, or set of genes for the purpose of correcting a genetic defect or providing an enhanced function. HTs can be used to mitigate a known genetic defect that is understood in the art to increase the likelihood of developing, or contribute directly to, a disease or condition. It is also understood that it may be advantageous to introduce HTs into cells or tissues at any time both before and after the generation of iPSCs. It is further understood that HTs may be introduced into cells or tissues in vivo or in vitro. Methods for the use of suitable mammalian expression vectors for the introduction of HTs are known the art and are described in U.S. Pat. Nos. 7,318,919, 5,399,346, 7,157,098, 7,074,772, 7,018,826, 6,743,620, which is hereby incorporated by reference. The regenerative medicine business or other stem cell technology business may perform, analyze, and confirm the introduction of HTs, or the service may be performed by a third party. In any case, the business of the present invention may bill the customer, or a third party for services rendered.

In one example of the use of HTs, the gene CCR5 encoding a human cell surface protein may be replaced with the heterologous transgene CCR5 variant known as CCR5 delta 32. Gene replacement can be done by specific integration of a replacement transgene into the genome of the target cell, or by spliceosome-mediated RNA trans-splicing. Cells with this replacement transgene, when administered to an individual in the form of iMSCs capable of providing partial or complete immune system function in an individual, enable enhanced protection in that individual against infection by the human immuno-deficiency virus (HIV) and a decreased likelihood of developing acquired immune deficiency after exposure to HIV.

Similar methods to accomplish this protection against HIV exposure via the use of HTs in combination with iPSCs will be evident to those skilled in the art based on the above description. For example, instead of replacing CCR5 with CCR5 delta 32, cells can be transfected with a vector encoding a hairpin RNA that silences only wild-type CCR5 and transfected with a vector that forces the expression of CCR5 delta 32 either before or after generation of iPSCs. Other methods to silence endogenous genes are known to those skilled in the art and can be employed to the same effect including but not limited to: antisense oligonucleotides, triple helix forming oligonucleotides, or ribozymes. It is also recognized that those skilled in the art will also be able to identify other variants of CCR5 or other genes such as CD4, or CXCR4 that enable protection from HIV exposure. It further recognized that this approach, possibly utilizing alternative transgenes, may be generally useful by those skilled in the art for protection against infection by any virus or infectious agent that requires a specific host gene to infect or replicate.

Forced expression of HTs in combination with the use of iPSCs can also be used to treat a genetic defect or disease allele. The individual to be treated may or may not be currently suffering from a genetic disease. Cells may be transfected with a vector containing nucleic acid that acts to specifically silence a deleterious dominant disease gene or allele, but not a wild-type allele. Such a silencing nucleic acid may take the form of a vector encoding for an oligonucleotide, such as a short hairpin RNA molecule, an antisense oligonucleotide, or a triple helix forming oligonucleotide that specifically silences the disease causing mutation. In other cases a transgene encoding for a ribozyme or an oligonucleotide promoting spliceosome-mediated RNA trans-splicing may be used.

Forced expression of HTs in combination with the use of iPSCs can also be used to treat a genetic defect or disease allele by providing a missing or insufficient function, gene, or gene product to an individual. For example, iPSCs induced from a sample donated by an individual suffering from a factor VIII deficiency may be transfected with a wild-type factor VIII gene and administered to the individual or recipient. In another case, the donor is an HLA-type match to, or family member of, the recipient. In still other cases, the donor and recipient are unrelated.

In a specific embodiment, a donor carrying a variant of the human gene breast cancer 1 early onset or BRCA1 that is known to increase the likelihood of developing breast cancer may elect to undergo an autologous transplant of differentiated breast tissue derived from iPSCs after a prophylactic mastectomy. A heterologous transgene may be used to replace the deleterious BRCA1 gene variant by any of the methods disclosed above with a variant that does not contribute to the likelihood of developing early onset breast cancer in the donated somatic cells prior to or after generation of iPSC. Variations of this approach will be evident to those skilled in the art based on the present description. For example, mutations in the gene RPE65 lead to blindness. Differentiated cells of the retina generated from donor derived iPSCs that express a wild-type RPE65 allele may be used to treat this condition by administering the differentiated cells to the patient.

Similarly, gene therapy in combination with use of iPSCs and/or differentiated cells and tissues thereof may be used for mitigating a variety of genetic factors or diseases including but not limited to one or more of following: Alzheimer's disease, Parkinson's disease, cystic fibrosis, hemophilia, diabetes, multiple sclerosis, liver disease, kidney disease, cardiac disease, Crohn's disease, severe combined immune deficiency, arthritis, rheumatoid arthritis, metabolic disorders, a proliferative disease such as cancer, or any disease or condition caused in whole or in part by a specific gene variant or set of gene variants. Several lists of genes and gene variants currently known to contribute to diseases or conditions are known to the art. For example, a number of online databases of disease alleles and associated diseases and conditions are described in U.S. application Ser. No. 12/157,967, filed Jun. 13, 2008; First Inventor Kazuhiro Sakurada, which is herein incorporated by reference in its entirety. It is understood that the number of known alleles that contribute to diseases or conditions will continue to increase and that the methods described herein are also applicable to disease or condition-associated alleles as yet undescribed.

Sometimes, a particular gene therapy approach may be deleterious in and of itself if applied to a whole individual. A particular advantage of the present methods is that the gene therapy can be performed outside the body and targeted only to a specific cell-type or tissue. For example, rheumatoid arthritis is a common chronic systemic autoimmune disease whose pathogenesis is not fully understood. The disease is associated with, among other symptoms, severe inflammation and pain in the joints of the body. In one embodiment, iPSCs are generated from an autologous, related, or unrelated donor and subjected to forced expression of HTs that downregulate the autoimmune reaction. iPSCs are differentiated into cells and tissue of the affected area and administered to the patient. HTs that can downregulate an autoimmune reaction are known to those skilled in the art (see Expert Opinion on Therapeutic Targets, Volume 4, Number 4, August 2000, pp. 481-495(15)). Other HTs that might be used to mitigate a disease or condition include but are not limited to: apolipoprotein E, cystic fibrosis transmembrane conductance regulator, insulin, hemoglobin, dystrophin, breast cancer 1 early onset, breast cancer 2 early onset, adenosine deaminase, factor VIII, or factor IX.

The successful introduction of HTs may be confirmed by an assay for presence or expression of the transgene. This assay may involve i) the detection of the polypeptide encoded by the transgene by techniques known to the art including but not limited to blotting, enzyme assay, immunoassay or mass spectrometry, ii) detection of the ribonucleic acid message encoded by the transgene by techniques known to the art including but not limited to quantitative pcr, SAGE, or blotting, microarray, or iii) detection of a co-transfected marker gene that confers a detectable phenotype including but not limited to: resistance to the drug G418, fluorescence as in the case of green fluorescent protein, or an enzyme activity. In some cases the co-transfected marker gene is present on the same vector as the beneficial transgene, in other cases it is on a separate vector. In some cases, more than one transgene is introduced into the cells.

In other cases, the transgene may provide a cell-fate determining function to ensure that iPSCs differentiate into a specific cell-type or tissue. For example, i) transcription factors including but not limited to: Isl-1, en-1, en-2, nurr-1, myoD, myogenin, or forkhead box proteins, ii) growth factors including but not limited to: hedgehog, wnt genes, transforming growth factor beta, granulocyte colony stimulating factor, granulocyte macrophage stimulating factor, nerve growth factor, neurotrophin, platelet-derived growth factor, erythropoeitin, thrombopoietin, myostatin, growth differentiation factor 9, acidic fibroblast growth factor, basic fibroblast growth factor, epidermal growth factor, insulin like growth factor, or hepatocyte growth factor, and iii) growth factor receptors. In some cases those skilled in the art may wish to use a variant or mutation of a transgene to provide the cell-fate determining function. In still other cases multiple HTs may be used to provide the cell-fate determining function.

Forced expression of HTs may include introducing one or more mammalian expression vectors encoding the desired transgene to a population of cells. The HTs may be introduced into the cells as exogenous genes. In some cases, the exogenous genes are integrated into the genome of a host cell and its progeny. In other cases, the exogenous genes are integrated into the genome of a host cell and its progeny and replace an endogenous variant of that gene. In still other cases the exogenous genes persist in an episomal state in the host cell and its progeny. Exogenous genes may be genes that are transfected into the cell from an external source. In some cases, a natural version of the gene may already exist in the cell but an additional "exogenous gene" is added to the cell to induce polypeptide expression. A single mammalian expression vector may contain two or more HTs. In other cases, one or more expression vectors encoding a transgene polypeptide are used. In some embodiments, each of the HTs to be expressed is encoded on a separate mammalian expression vector.

Examples of suitable mammalian expression vectors include but are not limited to one or more of the following: recombinant viruses, nucleic acid vectors, such as plasmids, bacterial artificial chromosomes, yeast artificial chromosomes, human artificial chromosomes, cDNA, cRNA, and PCR product expression cassettes. Examples of suitable promoters for driving expression of HTs include: the natural promoter of the transgene; retroviral LTR elements; constitutive promoters such as CMV, HSV1-TK, SV40, EF-1α, β-actin; PGK, and inducible promoters, such as those containing Tet-operator elements. In some cases, one or more of the mammalian expression vectors encodes, in addition to an HT, a marker gene that facilitates identification or selection of cells that have been transfected or infected. Examples of marker genes include, but are not limited to, fluorescent protein genes, e.g., for EGFP, DS-Red, YFP, and CFP; proteins conferring resistance to a selection agent, e.g., the neoR gene, and the blasticidin resistance gene.

In some cases, the HTs are genetically fused in frame with a transport protein amino acid sequence, e.g., that of a VP22 polypeptide as described in, e.g., U.S. Pat. Nos. 6,521,455, 6,251,398, and 6,017,735. Such VP22 sequences confer intercellular transport of VP22 fusion polypeptides from cells that have been transfected with a VP22 fusion polypeptide expression vector to neighboring cells that have not been transfected or transduced. See, e.g., Lemken et al (2007), Mol Ther, 15(2):310-319. Accordingly, the use of HT-VP22 fusion polypeptides can significantly increase the functional efficiency of transfected mammalian expression vectors in the regenerative medicine methods of the present invention.

The methods of the present invention are not limited to any particular gene therapy methods. Gene therapy methods contemplated by the present invention include but are not limited to the use of recombinant viruses, proteoliposomes, nucleic acid vectors. These gene therapy methods may be used to treat any diseases or disorders of the present invention.

D. Differentiation of iPSCs

Induced stem cells may be differentiated into cell-types of various lineages as deemed necessary or advantageous for running the regenerative medicine business or other stem cell technology business. Methods of differentiating iSCs, iPSCs, or iMSCs into cell types of various lineages include but are not limited to the addition of growth factors, hormones, or cell culture media additives, the use of spent media, co-culture of iSCs in the presence of other cells, and the use of alternative culture conditions such as lower or higher temperature. Specific methods for differentiation of iPSCs are more fully provided in U.S. application Ser. No. 12/157,967, filed Jun. 13, 2008; First Inventor Kazuhiro Sakurada, which is herein incorporated by reference in its entirety.

Differentiated cell types, tissues, and organs of the present invention include but are not limited to differentiation of iPSCs into neural stem cells, cardiac stem cells, and hepatic stem cells. Differentiated cell types further include but are not limited to neurons, oligodendrocytes, astrocytes, fibroblasts, cardiomyocytes, pancreatic beta cells, hepatocytes, and myocytes. Differentiation of iPSCs is also understood to include the generation of tissues and organs. It is also understood that the methods of the present invention may apply to methods of differentiating iPSCs that are currently unknown to the art. Differentiated cells of the present invention may also be purified from cells that are not successfully differentiated into the desired cell-type using a variety of methods including but not limited to cell sorting, and magnetic separation.

In some cases a kit is marketed and sold which includes a means for generation of differentiated cells from iPSCs, and optionally a means for administering the cells to an individual. In some cases, the donor, a third party, or a payee thereof, may be billed for the generation of differentiated cells from iSCs.

The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

The differentiated cells derived from the induced cells may be terminally differentiated cells, or they may be capable of giving rise to cells of a specific lineage. For example, induced cells can be differentiated into a variety of multipotent cell types, e.g., neural stem cells, cardiac stem cells, or hepatic stem cells. The stem cells may then be further differentiated into new cell types, e.g., neural stem cells may be differentiated into neurons; cardiac stem cells may be differentiated into cardiomyocytes; and hepatic stem cells may be differentiated into hepatocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

Any known method of generating neural stem cells from ES cells may be used to generate neural stem cells from induced cells, See, e.g., Reubinoff et al., (2001), Nat, Biotechnol., 19(12): 1134-40. For example, neural stem cells may be generated by culturing the induced cells as floating aggregates in the presence of noggin, or other bone morphogenetic protein antagonist, see e.g., Itsykson et al., (2005), Mol, Cell Neurosci., 30(1):24-36. In another example, neural stem cells may be generated by culturing the induced cells in suspension to form aggregates in the presence of growth factors, e.g., FGF-2, Zhang et al., (2001), Nat. Biotech., (19): 1129-1133. In some cases, the aggregates are cultured in serum-free medium containing FGF-2. In another example, the induced cells are co-cultured with a mouse stromal cell line, e.g., PA6 in the presence of serum-free medium comprising FGF-2. In yet another example, the induced cells are directly transferred to serum-free medium containing FGF-2 to directly induce differentiation.

Neural stems derived from the induced cells may be differentiated into neurons, oligodendrocytes, or astrocytes. Often, the conditions used to generate neural stem cells can also be used to generate neurons, oligodendrocytes, or astrocytes.

Dopaminergic neurons play a central role in Parkinson's Disease and other neurodegenerative diseases and are thus of particular interest. In order to promote differentiation into dopaminergic neurons, induced cells may be co-cultured with a PA6 mouse stromal cell line under serum-free conditions, see, e.g., Kawasaki et al., (2000) Neuron, 28(1):31-40. Other methods have also been described, see, e.g., Pomp et al., (2005), Stem Cells 23(7):923-30; U.S. Pat. No. 6,395,546, e.g., Lee et al., (2000), Nature Biotechnol., 18:675-679

Oligodendrocytes may also be generated from the induced cells. Differentiation of the induced cells into oligodendrocytes may be accomplished by known methods for differentiating ES cells or neural stem cells into oligodendrocytes. For example, oligodendrocytes may be generated by co-culturing induced cells or neural stem cells with stromal cells, e.g., Hermann et al. (2004), J Cell Sci. 117(Pt 19):4411-22. In another example, oligodendrocytes may be generated by culturing the induced cells or neural stem cells in the presence of a fusion protein, in which the iterleukin (IL)-6 receptor, or derivative, is linked to the IL-6 cytokine, or derivative thereof. Oligodendrocytes can also be generated from the induced cells by other methods known in the art, see, e.g. Kang et al., (2007) Stem Cells 25, 419-424.

Astrocytes may also be produced from the induced cells. Astrocytes may be generated by culturing induced cells or neural stem cells in the presence of neurogenic medium with bFGF and EGF, see e.g., Brustle et al., (1999), Science, 285: 754-756.

Induced cells may be differentiated into pancreatic beta cells by methods known in the art, e.g., Lumelsky et al., (2001) Science, 292:1389-1394; Assady et al., (2001), Diabetes, 50:1691-1697; D'Amour et al., (2006), Nat. Biotechnol., 24:1392-1401; D'Amour et al., (2005), Nat. Biotechnol. 23:1534-1541. The method may comprise culturing the induced cells in serum-free medium supplemented with Activin A, followed by culturing in the presence of serum-free medium supplemented with all-trans retinoic acid, followed by culturing in the presence of serum-free medium supplemented with bFGF and nicotinamide, e.g., Jiang et al., (2007), Cell Res., 4:333-444. In other examples, the method comprises culturing the induced cells in the presence of serum-free medium, activin A, and Wnt protein from about 0.5 to about 6 days, e.g., about 0.5, 1, 2, 3, 4, 5, 6, days; followed by culturing in the presence of from about 0.1% to about 2%, e.g., 0.2%, FBS and activin A from about 1 to about 4 days, e.g., about 1, 2, 3, or 4 days; followed by culturing in the presence of 2% FBS, FGF-10, and KAAD-cyclopamine (keto-N-aminoethylaminocaproyl dihydro cinnamoylcyclopamine) and retinoic acid from about 1 to about 5 days, e.g., 1, 2, 3, 4, or 5 days; followed by culturing with 1% B27, gamma secretase inhibitor and extendin-4 from about 1 to about 4 days, e.g., 1, 2, 3, or 4 days; and finally culturing in the presence of 1% B27, extendin-4, IGF-1, and HGF for from about 1 to about 4 days, e.g., 1, 2, 3, or 4 days.

Hepatic cells or hepatic stem cells may be differentiated from the induced cells. For example, culturing the induced cells in the presence of sodium butyrate may generate hepatocytes, see e.g., Rambhatla et al., (2003), Cell Transplant, 12: 1-11. In another example, hepatocytes may be produced by culturing the induced cells in serum-free medium in the presence of Activin A, followed by culturing the cells in fibroblast growth factor-4 and bone morphogenetic protein-2, e.g., Cai et al., (2007), Hepatology, 45(5): 1229-39. In an exemplary embodiment, the induced cells are differentiated into hepatic cells or hepatic stem cells by culturing the induced cells in the presence of Activin A from about 2 to about 6 days, e.g., about 2, about 3, about 4, about 5, or about 6 days, and then culturing the induced cells in the presence of hepatocyte growth factor (HGF) for from about 5 days to about 10 days, e.g., about 5, about 6, about 7, about 8, about 9, or about 10 days.

The induced cells may also be differentiated into cardiac muscle cells. Inhibition of bone morphogenetic protein (BMP) signaling may result in the generation of cardiac muscle cells (or cardiomyocytes), see, e.g., Yuasa et al., (2005), Nat. Biotechnol., 23(5):607-11. Thus, in an exemplary embodiment, the induced cells are cultured in the presence of noggin for from about two to about six days, e.g., about 2, about 3, about 4, about 5, or about 6 days, prior to allowing formation of an embryoid body, and culturing the embryoid body for from about 1 week to about 4 weeks, e.g., about 1, about 2, about 3, or about 4 weeks.

In other examples, cardiomyocytes may be generated by culturing the induced cells in the presence of leukemia inhibitory factor (LIF), or by subjecting them to other methods known in the art to generate cardiomyocytes from ES cells, e.g., Bader et al., (2000), Circ. Res., 86:787-794, Kehat et al., (2001), J. Clin. Invest., 108:407-414; Mummery et al., (2003), Circulation, 107:2733-2740.

Examples of methods to generate other cell-types from induced cells include: (1) culturing induced cells in the presence of retinoic acid, leukemia inhibitory factor (LIF), thyroid hormone (T3), and insulin in order to generate adipocytes, e.g., Dani et al., (1997), J. Cell Sci., 110: 1279-1285; (2) culturing induced cells in the presence of BMP-2 or BMP-4 to generate chondrocytes, e.g., Kramer et al., (2000), Mech. Dev., 92:193-205; (3) culturing the induced cells under conditions to generate smooth muscle, e.g., Yamashita et al., (2000), Nature, 408:92-96; (4) culturing the induced cells in the presence of beta-1 integrin to generate keratinocytes, e.g., Bagutti et al., (1996), Dev. Biol., 179:184-196; (5) culturing the induced cells in the presence of Interleukin-3(IL-3) and macrophage colony stimulating factor to generate macrophages, e.g., Lieschke and Dunn (1995), Exp. Hemat., 23:328-334; (6) culturing the induced cells in the presence of IL-3 and stem cell factor to generate mast cells, e.g., Tsai et al., (2000), Proc. Natl. Acad. Sci. USA, 97:9186-9190; (7) culturing the induced cells in the presence of dexamethasone and stromal cell layer, steel factor to generate melanocytes, e.g., Yamane et al., (1999), Dev. Dyn., 216:450-458; (8) co-culturing the induced cells with fetal mouse osteoblasts in the presence of dexamethasone, retinoic acid, ascorbic acid, beta-glycerophosphate to generate osteoblasts, e.g., Buttery et al., (2001), Tissue Eng., 7:89-99; (9) culturing the induced cells in the presence of osteogenic factors to generate osteoblasts, e.g., Sottile et al., (2003), Cloning Stem Cells, 5:149-155; (10) overexpressing insulin-like growth factor-2 in the induced cells and culturing the cells in the presence of dimethyl sulfoxide to generate skeletal muscle cells, e.g., Prelle et al., (2000), Biochem. Biophys. Res. Commun., 277:631-638; (11) subjecting the induced cells to conditions for generating white blood cells; or (12) culturing the induced cells in the presence of BMP4 and one or more: SCF, FLT3, IL-3, IL-6, and GCSF to generate hematopoietic progenitor cells, e.g., Chadwick et al., (2003), Blood, 102:906-915.

In some cases, sub-populations of differentiated cells may be purified or isolated. In some cases, one or more monoclonal antibodies specific to the desired cell type are incubated with the cell population and those bound cells are isolated. In other cases, the desired subpopulation of cells expresses a reporter gene that is under the control of a cell type specific promoter.

In a specific embodiment, the hygromycin B phosphotransferase-EGFP fusion protein is expressed in a cell type specific manner. The method of purifying comprises sorting the cells to select green fluorescent cells and reiterating the sorting as necessary, in order to obtain a population of cells enriched for cells expressing the construct (e.g., hygromycin B phosphotransferase-EGFP) in a cell-type-dependent manner. Selection of desired sub-populations of cells may also be accomplished by negative selection of proliferating cells with the herpes simplex virus thymidine kinase/ganciclovir (HS-Vtk/GCV) suicide gene system or by positive selection of cells expressing a bicistronic reporter, e.g., Anderson et al. (2007) Mol Ther. (11):2027-2036.

E. Drug Discovery and Testing

One method of the regenerative medicine business or stem-cell technology business may be to provide libraries or panels of cells or tissues for screening of drugs or compounds for toxicity or efficacy in a reproducible manner. These panels may be used, for example, in a clinical or pre-clinical trial. These uses include determining dose response curves, effective concentrations, maximum tolerated dose, and minimum effective concentration. Methods and compositions related to generation and use of the panels are described in U.S. application Ser. No. 12/157,967, filed Jun. 13, 2008; First Inventor Kazuhiro Sakurada, which is herein incorporated by reference in its entirety and in U.S. Application, filed Jun. 12, 2009, First Inventor Kazuhiro Sakurada, which is herein incorporated by reference in its entirety.

The regenerative medicine business or stem-cell technology business may involve screening of agents, such as nucleotides, peptides, and small molecules for the ability to alter the developmental potential of a cell, for example a somatic cell. The altered cell may be transformed into, for example, a multipotent stem cell, progenitor cell, or pluripotent stem cell. Methods of screening for agents are further described, for example, in US application filed on Jun. 13, 2008; US application filed on Jun. 13, 2008; and US application filed on Jun. 12, 2009, First Inventor Kazuhiro Sakurada, which is hereby incorporated by reference.

In another embodiment, iSCs (e.g., iPSCs or iMSCs) generated from a subject, or cells differentiated from iSCs, may be tested against candidate drugs or therapies to determine a personalized drug efficacy and safety profile. For example, a subject may suffer from a condition such as depression, or any of the diseases or conditions described herein, that can be treated by several different drugs. Each drug may exhibit different pharmacokinetic parameters. In addition, each drug may interact with the subject in unpredictable ways and be tolerated to differing degrees. Said subject may provide a biological sample to a stem cell technology business. The business may then generate hepatocytes and neurons from the biological sample after induction of iPSCs. These hepatocytes may then for example be tested for toxicity of the candidate drugs, while the neurons are tested for efficacy. In other cases, the iPSCs are differentiated into cardiomyocytes, which are used in toxicity studies.

Panels of Induced Pluripotent Stem Cell Lines

In some cases, the methods described herein utilize a panel of iPSC lines or a panel of cells differentiated from iPSC lines. A panel of iPSC lines comprises multiple iPSC lines or iSC cell lines, e.g., multipotent or pluripotent iSC lines, that meet certain selection criteria. Also provided herein are panels of cells differentiated from iPSC or iMSC lines as described herein. Such panels of differentiated cells include, but are not limited to, panels of neural stem cells, neurons, retinal cells, glial progenitor cells, glial cells, cardiac progenitor cells, cardiomyocytes, pancreatic progenitor cells, pancreatic beta cells, hepatic stem cells, hepatocytes or lung progenitor cells. In some cases, the selection criteria for inclusion of an iPSC line in a panel of iPSC lines are determined prior to generating the iPSC lines that will constitute the panel. In other cases, the selection criteria are applied to iPSC lines generated before hand, e.g., a bank of iPSC lines. Selection criteria include, but are not limited to, the presence or absence of a particular health condition in an iPSC donor, a positive drug response in an iPSC donor, negative, positive, or adverse drug responses in an iPSC donor, the presence or absence of a particular phenotype in an iPSC line or in cells differentiated from the iPSC line, and the presence or absence of one or more polymorphic alleles in the cell lines or their corresponding donors.

In some embodiments, where selection criteria include the presence or absence of one or more polymorphic alleles, the panel includes genetically diverse human iSC (e.g., iPSC or iMSC) lines in which each iSC (e.g., iPSC or iMSC) line carries at least one polymorphic allele that is unique among the iSCs (e.g., iPSC or iMSC) to be included in the panel, e.g., 5 to 10, 20 to 50, 50 to 200, 200 to 500, 500 to 1000, 1000 to 5000, 5000 to 20000, or 20000 to 50000 polymorphic alleles that are unique within the panel of iSC (e.g., iPSC or iMSC) lines. Such polymorphic alleles may include, e.g., a SNP allele, a promoter allele, or a protein-encoding allele. Polymorphic alles can be screened and scored for by genotyping using any of a number of known genotyping assays. In some cases, the genotyping assay is a multiplexed genotyping assay, e.g., a nucleic acid microarray assay platform such as a "SNP chip." In some cases, the one or more polymorphic alleles are pre-selected. In some embodiments, the one or more preselected alleles are polymorphic alleles associated with a health condition or a predisposition to a health condition. Examples of polymorphic alleles associated with a health condition or a predisposition to a health condition, include, but are not limited to, polymorphic alleles associated with a neurodegenerative disorder, a neurological disorder, an eye disease, a mood disorder, a respiratory disease, a cardiovascular disease, an immunological disorder, a hematological disease, a metabolic disorder, or a drug sensitivity condition. Some examples of polymorphic alleles associated with a health condition are provided in Table 3 above. Polymorphic alleles may include polymorphic alleles in an encoded protein or a regulatory sequence affecting the expression of the encoded protein. In some cases, the encoded protein is a drug target. Examples of drug target proteins include, but are not limited to, GPCRs, ion channels, kinases, enzymes, and transcription factors.

In other embodiments, the one or more polymorphic alleles are pre-selected based on the presence of a high degree of surrounding linkage disequilibrium in the genome, which has been proposed as a signature of genomic loci that are likely to impact many common health conditions. Methods for identifying SNPs having a high surrounding linkage disequilibrium and genes near such SNPs are described in, e.g., Wang et al (2006), Proc Natl Acad Sci USA, 103(1):135-140.

In some cases, a panel of iSC (e.g., iPSC or iMSC) lines includes lines generated from subjects that are diagnosed as suffering from one or more health conditions. The one or more health conditions may be one or more health conditions that are common to all of the iSC donors (e.g., iPSC or iMSC), or they may be health conditions that are different between the iSC (e.g., iPSC or iMSC) donors.

In certain cases, a panel of iSC (e.g., iPSC or iMSC) lines includes iSC (e.g., iPSC or iMSC) lines generated from subjects that are both diagnosed as suffering from a health condition and carry a polymorphic allele associated with a health condition, e.g., a polymorphic allele associated with the diagnosed health condition.

A panel of iSC (e.g., iPSC or iMSC) lines may include iSC (e.g., iPSC or iMSC) lines from at least about 10 individuals to at least about 50,000 individuals, e.g., 10 to 50, 20 to 100, 50 to 250, 100 to 1000, 250, to 2000, 500 to 5000, 1000 to 10,000, 2500 to 20,000, 10,000, to 30,000, 20,000 to 40,000, or 30,000 to 50,000 individuals.

A panel of iSC (e.g., iPSC or iMSC) lines may include iSC (e.g., iPSC or iMSC) lines from at least two ethnic groups, e.g., 3, 4, 5, 6, 7, 8, 9, 10, 12, 15, 20, 25, 30, or 50 ethnic groups. Examples of ethnic groups include, but are not limited to, Europeans, Japanese, Chinese, and the Yoruba of Nigeria, and ethnic groups listed in Table 4.

TABLE 4

| Exemplary Ethnic Groups |
| --- |
| Africa |
| Bantu |
| Biaka |
| Mandenka |
| Mbuti pygmy |
| Mozabite |
| San |
| Yoruba |
| Native America |
| Colombian |
| Karitiana |
| Mava |
| Pima |
| Surui |
| Asia Ctrl/South |
| Balochi |
| Brahui |
| Burusho |
| Hazara |
| Kalash |
| Makrani |
| Pathan |
| Sindhi |
| Uyghur |
| Western Asia |
| Bedouin |
| Druze |
| Eastern Asia |
| Cambodian |
| Dai |
| Daur |
| Han (N. China) |
| Han (S. China) |
| Hezhen |
| Japanese |
| Lahu |
| Miao |
| Mongola |
| Naxi |
| Oroqen |
| She |
| Tu |
| Tujia |
| Xibo |
| Yakut |
| Yi |
| Europe |
| Adygei |
| Basque |
| French |
| North Italian |
| Orcadian |
| Russian |
| Sardinian |
| Tuscan |
| Oceania |
| Melanesian |
| Papuan |

V. Database Construction Operation and Access

It may be advantageous to construct or maintain a database related to customers, potential customers, donors, and samples of the regenerative medicine business or stem cell technology business. Such a database may be useful for tracking customers, tracking samples, searching for suitable samples for customers and potential customers, and marketing to customers and potential customers.

A representative or agent of the regenerative medicine business or stem cell technology business, an individual, a donor, a customer, or third party such as medical professional, a genetic counselor, a licensee, a health care provider, an insurance provider, a testing facility, or any individual or entity to whom the regenerative medicine business or stem cell technology business grants database access to, herein referred to as a database user, may search a database of the present invention that contains descriptions of donors, customers, stored cells, and tissues to identify suitable samples for use in a therapy or as a research tool.

Sample information referring to harvested donor samples, cultured cells, iSCs, differentiated cells, and tissues derived thereof may be entered into the database. In some cases the information is entered into the database by an employee or agent of the business. In other cases the information is entered into the database by a database user. The act of logging in samples can be understood to mean entering data relating to the sample, the donor, or both into the database, or collecting or recording the data.

Information in the database can include but is not limited to one or more of the following: a unique identification, any information determined during analysis of the donor or sample, presence of transgenes, whether the sample is part of a panel as described herein, and the price for purchase or manipulation of the sample.

The database may be a computer database or set of computer databases or modules. The generic technique of constructing a computer database is known to the art, e.g. U.S. Pat. No. 7,370,366. The information may be entered into the database using a computer. In some cases, the database is accessed via the internet or other form of electronic information exchange such as a telephone or a secure network. Database access may be restricted to employees of the regenerative medicine business or stem cell technology business, donors, customers, licensees, prospective customers, or third parties. Alternatively, some access to the database may be available to any individual or entity. In some cases, restriction of access to the database is performed via the use of a unique user identification and password. Database users may be grouped according to a hierarchical level of allowed information access, e.g. a donor may access all the information pertaining to the samples stored for that donor, but cannot access information about other donor samples or clients. In some cases, a database user may have access to some information about all the samples in the database, but cannot access information that would violate privacy laws or enable competitive business practices. In other cases, a database user may purchase different levels of database access.

A database user may search the database based on one or more criteria. Such criteria may be but are not limited to one or more of the following: donor age, disease state, HLA-type, cell-type, genomic data, disease state, SNP data, or any information stored in the database. A representative of the business or third party such as a medical professional, or genetic counselor may perform the search on behalf of a customer or potential customer. The results of any such search described may provide enough information to motivate the customer or potential customer to purchase a product or service from the business. In some cases, the donor, a third party, or payee thereof, may be billed for the access to the database regardless of the results of any search. Billing may be based on a per-computer (per seat) license, a per search license, a per-month of access license, a per minute of use license, or any method known to the art of billing for access to a database.

In one example, a potential customer may access the database through a world-wide-web interface to search for samples that match one or more criteria such as a given HLA-type. Identification numbers corresponding to matching samples in the database are provided and the results may be searched with additional criteria to further narrow the number of matches. The potential customer may at this point order cells or tissues generated from the sample from the business, be billed, and pay for services and materials.

The database user interface may include a computer form or a web page including a means for a user to login, and a means for new user registration. The user interface may further include a form or set of forms containing search criteria, and a means to input values for the search criteria. Said search criteria may include but are not limited to any information that may be contained in the database. In some cases, the search criteria that may be displayed by the interface or filled in by the user may be restricted according to the level of database access available to that user. If a small number of possible values are available for a given search criterion, the interface may include a set of choices for filling that particular search criterion such as in the form of a drop down menu. In other cases, the interface may include an example specifying a valid format for a given search criteria value. Said search criteria values may be filled in by the database user and transmitted to a server. Said transmission may be interpreted as a search query by the server. The search query may then be performed on the database. The database may reside on the server, or may reside on another computer. The results of any search by a database user may then be transmitted and displayed as a web page on the database user's computer. Said results may then be further refined by including additional or alternative search criteria. A customer or potential customer may access the database by electronic communication such as over a computer network. Alternatively, the database user may access the database by contacting a representative of the business or a third party to perform the database search.

VI. Kits

Kits anticipated by the present invention include one or more of the following: 1) a kit for the acquisition, storage and transportation of a donor sample, 2) a kit for the generation of iPSCs, or of cells on some stage of developing towards iPSCs, 3) a kit for the differentiation of iPSCs into cells or tissues, and 3) a kit providing iPSCs, cells, or tissues for administering to an individual. A kit for acquisition and storage of samples may comprise: (a) a means for obtaining a sample of somatic cells from a donor; (b) reagents and materials for storage of somatic cells in a manner suitable for induction of iSCs; and (c) instructions for use of the kit. The kit may also include a means of transporting the sample to a storage facility; a means for recording donor and sample information; a means to input donor and sample information into a database In some cases, a kit may comprise: (a) reagents and materials for culturing somatic cells, iPSCs and cells derived thereof including one or more of the following: cell culture media, antibiotics, and cell culture dishes; and (b) a means for generating iPSCs from somatic cells including one or more of the following: plasmids encoding IFs, transfection reagents, and recombinant viruses. In some cases, a kit includes a temporary license for the use of iPSC technology; in some cases a kit includes instructions for use of the kit. For example, the kit may include instructions how to care for the biological sample, or how to use the reagents provided in order to generate iPSCs from the biological sample.

In some cases, a kit for providing iPSCs, or cell, tissues, or organs differentiated from iPSCs includes: (a) a means for administering a therapeutic amount of biological material to an individual; and (b) a container containing iSCs or cells, tissues or organs derived thereof. In some cases, the kit also includes instructions for administering the biological material to an individual.

VII. Business Methods (a) Reaching the Target Market

A robust marketing strategy may enable greater market share, and decrease time to profitability in the nascent field of regenerative medicine. The overall marketing strategy may be broken up into several modules including but not limited to: 1) marketing of sample acquisition and storage, 2) marketing of generation of iSCs, 3) marketing of product delivery for use as a therapeutic agent, 4) marketing of research products, 5) marketing of kits of the regenerative medicine business or stem cell technology business, 6) marketing of database access and use, and 7) marketing of core technology and use licenses for core technologies and intellectual property.

The target audience for the marketing modules can be any individual or entity. The target audience for 1) 2) and 3) may be further divided into groups including but not limited to: medical professionals, genetic counselors, veterinarians, those who are suffering from a disease or condition, those who anticipate suffering from a disease or condition, the elderly, expectant mothers, or parents, or any individual interested in or potentially interested products and services of the regenerative medicine business or stem cell technology business. The target market for 4) includes but is not limited to researchers, universities, research laboratories, drug development companies, contract research organizations, government entities such as the National Institutes of Health, or any individual or entity interested in obtaining a panel of iSCs, or cells or tissues derived thereof. The target market for 7) may consist of independent entities that may be interested in gaining access to the use of iSC technology such as independent cell-banking companies or regenerative medicine businesses or stem cell technology business. The target market for 4) and 5) may consist of any of the individuals or entities previously listed.

Methods of marketing to a target audience may be facilitated by marketing to members of disease support groups or advocacy groups. Such groups include but are not limited to: the Multiple Sclerosis Society, the Muscular Dystrophy Association, the Cystic Fibrosis Foundation, the American Diabetes Association, the Alzheimer's Association, or the National Hemophilia Foundation. Additional disease support and advocacy groups can be found at http://www.kumc.edu/gec/support/, which is hereby incorporated by reference.

Methods of marketing to a target audience may further include marketing to individuals within a group, or groups as a whole, whose members represent a desirable demographic. Said groups include but are not limited to: members of the AARP; subscribers to parenting and pregnancy magazines such as *Parenting, Fit Pregnancy, Parents, Baby Talk, American Baby*, or *Exceptional Parent*; subscribers to health, lifestyle, or fitness magazines including but not limited to *Men's Health, Women's Health, Boomer, Arthritis Today, Body and Soul, Cooking Light, Diabetic Cooking, Diabetic Living, Healthy and Fit Magazine, Life Extension, Nutrition Today, Prevention, Self; Shape*, or *totalhealth*; subscribers to science or technology magazines including but not limited to *Scientific American*, or *Wired*; readers of internet web pages, discussion groups, social networking groups, or blogs that relate to medicine, health, illnesses, or longevity including but not limited to members of the Daily Strength social networking site, members of Facebook or Myspace groups, readers of www.stemcellnews.com, or readers of http://www.webMD.com. In some cases however, it may be beneficial to reach potential customers of the business by placing advertisements in the general media such as for example newspapers, general interest magazines, or television commercials.

Individuals of certain groups may more effectively be marketed to by entering into collaborative agreements with the groups. Such collaborative agreements may include payment of a fee for access to members, provision of a discount for members in exchange for access to members, or any agreement which increases awareness of the products, services and benefits offered by the regenerative medicine business or stem cell technology business. Member access may take the form of provision of a list of member names and contact information such as address, electronic mail address, or telephone number. Alternatively, member access may take the form of scheduling informational sessions for group members. Such informational session may take the form of seminars or town-hall style meetings to discuss the benefits of the regenerative medicine business or stem cell technology business.

Marketing may take the form of print, television, or radio media, informational sessions, internet presence such as a webpage of the business, or any form which increases awareness of the products, services, and benefits offered by the regenerative medicine business or stem cell technology business. In some cases, marketing media may take the form of essays or articles in print media written by a representative of the business, a medical professional, or a third party such as a journalist, or a medical professional, describing aspects of the regenerative medicine business or stem cell technology business.

In the case of a webpage of the regenerative medicine business or stem cell technology business, marketing may include a discussion forum. Said discussion forum may be moderated to keep discussions on topic and to remove inflammatory speech. The webpage may further include a means for individuals to register contact information such as a phone number, address, or e-mail address. Said contact information may be used to disseminate information about the products and services of the regenerative medicine business or stem cell technology business.

It is further anticipated that the marketing methods of the business may further include a media relations department for contact with independent media outlets. Such a media relations department could consist of at least one individual who: discusses aspects of the regenerative medicine business or stem cell technology business with independent media outlets; and manages contact between spokespersons for the business, independent media outlets, and outside experts. Said outside experts may or may not be provided a fee for discussing aspects of the regenerative medicine business or stem cell technology business with independent media outlets.

Marketing may further include methods of marketing the products and services of the regenerative medicine business or stem cell technology business and benefits thereof by purchasing the rights to keyword search terms. Said keyword search terms when used by an individual in an internet search engine would trigger the display of an advertisement for the regenerative medicine business or stem cell technology business. Such keywords or phrases may include but are not limited to: words that are related to diseases or conditions actually or potentially cured or mitigated by the use of iSC technology such as Alzheimer's disease, or organ failure; or words related to target marketing audiences such as pregnancy, child, or new parent.

It may also be beneficial to the regenerative medicine business or stem cell technology business to market to individuals or entities that may service potential customers. Such individuals or entities include but are not limited to medical professionals, genetic counselors, fertility clinics, cell banking facilities, health spas, hospitals, insurance companies, cord blood banks, mid-wives, or blood banks. Marketing to such individuals or entities may be performed directly or through marketing to professional groups such as the American Medical Association, marketing to trade groups such as the American Society for Reproductive Medicine, or marketing to subscribers of vocational journals such as The Journal of the American Medical Association, Midwifery Today, The Journal of Genetic Counseling, or any other vocational journal.

Marketing of the products and services of the regenerative medicine business or stem cell technology business to individuals or entities that may service potential customers may also take the form of educational seminars or workshops. These workshops may provide sufficient training to allow the target audience to practice aspects of the regenerative medicine business or stem cell technology business as a franchisee or licensee.

In another embodiment, marketing may be performed based on the results analyses performed on donors or samples. For example, a donor may provide a sample to the business. This sample may then be analyzed prior to or after storage. The analysis may indicate a hereditary disease or condition. The business may then use this information to market products and services of the business that may be of interest to the donor in light of the results of the analysis. Similarly, new genetic factors of diseases or conditions may become known. The database of the business may then be searched for the presence of these new genetic factors. Donors may be identified that have these genetic factors and marketed to.

(b) Marketing and Selling Products and Services

Business methods of the present invention provide marketing of the products and services of the regenerative medicine business or stem cell technology business. One embodiment of the present invention provides marketing and selling of a sample acquisition and storage service as described herein. This service may or may not be done by the regenerative medicine business or stem cell technology business of the present invention. For example, the service may be performed by a third party cell banking company.

The methods of the present invention also provide marketing and selling the service of generating iSCs. Similarly, iSCs may be generated by third parties licensed to use the iSC technology of the present invention. This may be advantageous in cases where the customer is geographically distant from the location of the regenerative medicine business or stem cell technology business. The iPSCs may be generated using a kit sold by the regenerative medicine business or stem cell technology business.

In other cases, the present invention includes marketing and selling the service of differentiating iSCs into differentiated cells and tissues. As described previously for generation of iSCs, the actual differentiation steps may be outsourced to a third party. These differentiated cells and tissues include multipotent stem cells, somatic cells, fully differentiated cells, tissues, and organs. The methods of the present invention further provide marketing and selling iSCs, iMSCs, iPSCs, and differentiated cells and tissues.

The kits of the present invention may also be marketed and sold using the methods of the present invention.

The present invention also includes the business method of achieving approval from government entities for the marketing and selling of the products and services of the regenerative medicine business or stem cell technology business.

Billing

The method of the present disclosure provides a means for billing customers, third parties or payees thereof such as an insurance provider or government entity (e.g. Medicaid) for products and services of the regenerative medicine business or stem cell technology business. Said billing methods may include one or more of the following: billing for access or an increased level of access to the database of the present invention, billing for delivery of samples of the present invention, billing for license to practice iSC technology or license to run a regenerative medicine business or stem cell technology business based on iSC technology, or billing for delivery of kits of the present disclosure. In any case, billing events and or payments may be recorded in the database of the business. The regenerative medicine business or stem cell technology business may take as payment personal checks, money orders, credit cards, debit cards, wire transfers, or any other means known by which a payment may be made by those skilled in the art.

The term billing may include any act in which a customer or payee is informed of the amount owed the regenerative medicine business or stem cell technology business. In some cases, billing includes a notice mailed to a customer or payee including an itemized list of the products and services rendered. In other cases, billing may be performed by sending an electronic communication to a customer or payee. This communication may take the form of an electronic document or an e-mail notice to a customer to log into the database or web page of the business and retrieve a statement.

Some customers of the regenerative medicine business or stem cell technology business may also generate credits due to use of samples provided by one customer for another unrelated customer. This mechanism of providing credit to a customer for making sample available may be used to provide incentives for individuals to donate samples.

Billing events may be initiated by changes in the database. For example, a donor sample is obtained and sample information is added to the database. Said sample includes information about the medical insurance provider. This change in the database may for example automatically initiate billing to the donor or insurance provider for services and products related to sample acquisition, analysis and storage. Alternatively, billing may be initiated by a representative or agent of the business as a condition of providing a product or service of the business. In other cases, billing is performed on a recurring basis, such as monthly, for sample maintenance and storage.

In another embodiment of the present invention, billing is performed by a third party or licensee of the regenerative medicine business or stem cell technology business; for example, a physician or third party such as a cell-banking facility licensed to obtain and store samples for induction of stem cells. Said cell-banking facility may obtain a sample from a donor, input donor and sample information into the database, and bill the donor or insurance provider for materials and services rendered. Payment of the bill may then be passed onto the regenerative medicine business or stem cell technology business, and a differential retained by the third party or licensee.

EXAMPLES

Prophetic Example 1

This example illustrates the use of the products and services of the regenerative medicine business by a customer, herein referred to as subject A. Subject A first provides a biological sample, which is stored cryogenically by the regenerative medicine business. Optionally, induced pluripotent stem cells (iPSCs) may be derived from the biological sample by forcing the expression of induction factors such as Oct3/4, Sox2 and Klf4. The cells are induced to become pluripotent by following any method known in the art, e.g., a method described in U.S. application Ser. No. 12/157,967, filed Jun. 13, 2008, First Inventor Kazuhiro Sakurada, filed Jun. 12, 2009. Such iPSCs are then cryogenically stored for later use. At a later point in time, subject A suffers organ damage via liver failure. Subject A is deemed by those skilled in the art to require a liver transplant. Ordinarily, a liver transplant might require a long wait to identify a suitable donor, during which subject A might die. Even if a suitable donor were to be found, subject A would then have to look forward to a lifetime of immunosuppressive therapy.

In this case however, subject A or his physician contacts the regenerative medicine business and requests that an autologous liver, hepatocytes, or liver progenitor cells be generated from the stored donor sample. Said donor sample is identified by the business from the database by searching for the donor's name or other identifying information. The sample, or a portion thereof, is then thawed and cultured for a limited period of time such as one day to four months. During which time, cells from the donor sample are expanded. A portion of the expanded cells are stored cryogenically frozen in aliquots. Another portion is then used to generate induced pluripotent stem cells, which are then differentiated into liver (hepatic) stem cells. Said liver stem cells are then expanded to provide a therapeutic number of cells for subject A. The liver stem cells are analyzed for malignant or premalignant changes in genomic or gene expression profiles. The liver stem cells are then provided to subject A or subject A's physician in a kit suitable for administering to subject A. Suitable matrices, or pharmaceutical carriers for encouraging successful engraftment of hepatocytes or liver stem cells are known to those skilled in the art. It is also understood that this example is meant to apply to other materials or techniques for encouraging successful engraftment that may become known in the future.

The database of the business may be updated at each step to reflect changes to subject A's condition, changes to subject A's sample history, addition of new samples derived from subject A via expansion, induction, or differentiation, or billing events. Further each step of the business, or change in the database, may generate a billing event for subject A, or his insurance provider.

Prophetic Example 2

This example illustrates the use of the products and services of the regenerative medicine business by a customer, herein referred to as subject B. Subject B does not provide a sample to the regenerative medicine business. In this case, subject B also suffers liver failure due to trauma, and requires a transplant for which a suitable donor cannot be timely found. Subject B's physician obtains a kit provided by the regenerative medicine business for acquiring a suitable sample of biological material from subject B and transporting the sample to the regenerative medicine business. Upon receipt of the sample by the business, cells are analyzed, cultured and expanded. On the basis of donor and sample analysis, subject B is considered free of known diseases or conditions. A portion of expanded cells are stored cryogenically in individual aliquots for future use. A portion of expanded cells are also used to generate liver stem cells, which are then provided in the manner previously described.

Prophetic Example 3

This example illustrates the use of the products and services of the regenerative medicine business by a customer herein referred to as subject C. Subject C does not provide a sample to the regenerative medicine business. In this case, subject C suffers from a hereditary leukemia rendering an autologous transplant inadvisable because any autologous material contains the same hereditary factor that contributed to the leukemia.

Subject C's high resolution HLA type is determined by methods described herein from a sample of biological material, which is subsequently stored. The database of the regenerative medicine business is then searched to find an HLA serotype (low resolution HLA-type) match. Potential matches are then ranked according to donor and sample characteristics such as age of the donor (cells from younger donors are preferable), race or ethnic background of the donor (individuals of similar race or ethnic background are likely to have similar HLA-types), and disease state of the donor (donor's suffering from hereditary diseases may be less desirable), or CMV serologic status. Suitable donor samples are identified and further analyzed by high resolution HLA-type. A matching sample is then identified. If the matching sample comprises differentiated cells, induced pluripotent stem cells (iPSCs) are generated from the matching sample. Optionally, the matching sample may already include iPSCs. In the next step, the iPSCs are differentiated into hematopoietic stem cells. The hematopoietic stem cells are analyzed for malignant or premalignant changes, and provided to subject C, or subject C's physician for administering to subject C. Subject C's insurance provider is then billed for products and services rendered.

Prophetic Example 4

This example illustrates the use of the products and services of a stem cell technology business by a customer herein referred to as customer D. Customer D is a researcher developing new therapies for hereditary leukemias. In this case, customer D wishes to test possible therapies against (1) human leukemia cell lines, (2) human primary lymphocyte cells from individuals who are at risk of developing leukemia due to hereditary factors, and (3) disease free primary human lymphocyte cells. In addition, Customer D wishes to be able to reproducibly obtain genetically identical primary human cell lines in perpetuity for the purposes of testing new potential therapeutic agents as they become known to the art.

In this case, the regenerative medicine business or stem cell technology business possesses a panel of primary human lymphocytes from subject C (2) and subject B (3). Said cells of (2) and (3) are then provided to customer D for research purposes. Customer D or a third party payee is billed for products and services. Primary human cell lines ordinarily do not replicate for prolonged periods of time; therefore, customer D requires that primary human cell lines are generated using iPSC technology using samples from subject C and subject B and provided on a continuing basis. In this case, the regenerative medicine business or stem cell technology business generates and stores a large number of iPSCs that are generated from samples from subject C and subject B.

Customer D publishes or makes known the findings of his research involving primary human cell lines derived from subject C and subject B. Other researchers wish to reproduce the work of Customer D, or perform similar experiments using the same cells. These other researchers, therefore contact the regenerative medicine business or stem cell technology business to obtain the panel of cells described by customer D consisting of (2) and (3).

Prophetic Example 5

This example illustrates the use of the products and services of the regenerative medicine business by a customer herein referred to as Subject E. Subject E is an expectant mother. Subject E learns of the products and services of the regenerative medicine business by reading an advertisement in Pregnancy Magazine. Subject E wishes to have a sample from her child obtained and stored for possible future use. Subject E registers as a new user on the website of the regenerative medicine business, and purchases a neonatal sample collection kit paid for by credit card. Subject E provides the sample collection kit to her obstetrician for the purpose of collecting neonatal tissue from her child shortly after birth. The kit includes a means for obtaining, storing, and transporting blood cells from the umbilical cord of the neonate. The kit further includes a means for updating the database of the business to provide donor and sample information. The obstetrician follows the instructions included in the kit and obtains a suitable sample from Subject E's child. The sample is then transported to a third party cell-banking facility for cryogenic storage. The database of the regenerative medicine business is then updated to include donor and sample information. Subject E is then billed for sample handling and storage fees by the cell-banking facility. The cell banking facility remits a portion of Subject E's payment to the regenerative medicine business.

Prophetic Example 6

This example illustrates a method of marketing the products and services of the regenerative medicine business or stem cell technology business. In this example a website is constructed that includes 1) a home page in which a potential customer can access general information concerning the products and services of the regenerative medicine business or stem cell technology business including but not limited one or more of the following: a) methods of accessing the products and services, b) methods of contacting an agent or representative of the business, c) lists of diseases or conditions that may be mitigated by products and services or the business, d) information about collaborative partners of the business such as a third party cell banking facility that may obtain and store samples, e) information about products such as kits that may be ordered or are available from a store, and f) a means for registering as a new user to gain database access, and 2) a means for accessing the database of the regenerative medicine business or stem cell technology business to search for desirable samples such as those that match a particular HLA-type.

In this example, a potential client finds the website of the business through a variety of means such as by searching for keywords "stem" and "cell" using an internet search engine. The potential client explores whether there are samples that match the potential client's HLA-type, by registering as a new user, obtaining a login and password, logging in, and searching the database. The results of a database search reveals information such as specific samples of interest sorted by degree of match, information as to potential uses of the matching samples, and information as to how to obtain the samples. Additionally, the results of the database search market the advantages of providing an autologous sample.

Prophetic Example 7

This example illustrates the use of the products and services of a stem cell technology (SCT) business by a customer herein referred to as customer F. Customer F is an agent for a pharmaceutical company focused on developing assays for identifying molecules that improve molecular or cellular disease phenotypes in motor neurons, particularly molecules with the potential to treat patients suffering from spinal muscular atrophy (SMA). SMA is a neuromuscular degenerative disease that is among the leading causes of childhood paralysis and mortality. The disease exhibits a wide range of severity affecting infants through adults, and is subdivided into types I-IV based on the age of onset and severity of symptoms: Type I "Infantile" onset at ages 0-6 months and generally fatal); Type II "Intermediate," onset at ages 7-15 months; inability to stand or walk, but some ability to maintain a sitting position; Type III "Juvenile" onset at ages 18 months to 17 years, with some ability to walk, though potentially transient; Type IV "Adult," some muscle weakness, but no genetic basis known.

The molecular basis of SMA is linked to the Survival Motor Neuron (SMN) gene. The region of chromosome 5 that contains the SMN (survival motor neuron) gene has a large duplication. A large sequence that contains several genes occurs twice—i.e. once in each of the adjacent segments. The two copies of the gene—known as SMN1 and SMN2—differ by only a few base pairs. The SMN2 gene contains a mutation that occurs at the splice junction of intron 6 to exon 7 resulting in about 90% of SMN2 pre-mRNA transcripts being spliced into a form that excludes exon 7. This shorter mRNA transcript codes for a truncated SMN protein, which is rapidly degraded. About 10% of pre-mRNA transcript from SMN2 is spliced into the full length transcript that codes for the fully functional SMN protein. This splicing defect occurs in multiple cell types, although, for unknown reasons, the survival of motor neurons appear to be particularly affected.

SMA results from the loss of the SMN1 gene from both chromosomes, and its severity, ranging from SMA 1 to SMA 3, largely depends on whether the level of SMN2E7 transcript can make up for low levels or absence of exon 7-inclusive SMN 1 transcript. The mutations that cause the loss of SMN 1 are of two types. One type is deletion mutations, in which both copies of the SMN1 are missing. The other type of mutation is a conversion mutation in which both copies of the SMN1 gene have a point mutation resulting in the same splicing pattern as the SMN2 gene. As an initial step towards developing an in vitro assay for identifying molecules that can increase levels of exon 7-inclusive SMN2 (SMN2E7) transcript, we generated several iPSC lines from Coriell fibroblast lines established from three SMN1 −/− SMA patients and from two healthy SMN1−/+ subjects.

The molecular basis of SMA is linked to the Survival Motor Neuron (SMN) gene. The region of chromosome 5 that contains the SMN (survival motor neuron) gene has a large duplication. A large sequence that contains several genes occurs twice—i.e. once in each of the adjacent segments. A second change that is found only in humans is that the two copies of the gene—known as SMN1 and SMN2—differ by only a few base pairs. The important change in the SMN2 gene, for the purposes of SMA, is a silent mutation that occurs at the splice junction of intron 6 to exon 7. This affects splicing of the SMN2 pre-RNA, resulting in about 90% of the transcripts being inappropriately spliced into a form that excludes exon 7. This shorter mRNA transcript codes for a shorter SMN protein, which is rapidly degraded. About 10% of the mRNA transcript from SMN2 is spliced into the full length transcript that codes for the fully functional SMN protein.

The stem cell technology (SCT) business houses large numbers of panels of iPSCs (or of somatic cells that can be used to generate iPSCs) as well as panels of cells (e.g., neurons, motor neurons, hepatocytes, cardiomyocytes) differentiated from iPSCs. SCT may obtain the iPSCs from numerous sources. For some panels, the SCT business obtains tissue from participants in a clinical trial; the SCT business then generates panels of iPSCs. Each panel of iPSCs is used to generate differentiated cells. Some panels of iPSCs are used to generate several types of differentiated cells. In some services, the SCT provides panels of neurons (including dopaminergic neurons and motor neurons), hepatocytes, and cardiomyocytes all generated from the same panel of iPSCs. Customer F locates the web-site of the stem cell technology (SCT) business on the world wide web, or internet. Customer F then uses the "search" function on the web-site to locate lists of panels of cells currently available at SCT. Customer F may also use a function on the web-site to custom design sets of panels. Customer F desires the following panels of cells: (1) a panel of motor neurons differentiated from iPSCs derived from greater than 500 donors who display Type I SMA; (2) a panel of motor neurons differentiated from iPSCs derived from greater than 500 donors who display Type II SMA; (3) a panel of motor neurons differentiated from iPSCs derived from greater than 500 donors who display Type III SMA; (4) a panel of motor neurons differentiated from iPSCs derived from greater than 500 donors who display Type IV SMA; (5)-(8) panels of hepatocytes differentiated from iPSCs derived from the sets of donors described in (1)-(4); (9)-(12) panels of cardiomyocytes differentiated from iPSCs derived from the sets of donors described in (1)-(4); (13) panels of neurons differentiated from the sets of donors described in (1)-(4), where such sets are further modified to exclude all male donors; and (14) panels of neurons differentiated from the sets of donors described in (1)-(4), where such sets are further modified to exclude all female donors.

Customer searches the SCT site for panels matching his criteria. He succeeds with respect to panels (1) through (12) listed above. He adds (1) through (12) to his shopping basket. He then proceeds to the custom panel page and designs the panels described in (13) and (14). He next proceeds to the check out screen to complete his order, which may involve providing billing information, delivery address; delivery date, and other purchasing information.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for providing mammalian iPSC-derived differentiated cells to a customer, comprising:
    (a) expanding mammalian iPSCs and stocking the expanded iPSCs in an iPSC bank, wherein the iPSCs are obtained from a plurality of different iPSCs, each of the iPSCs being derived from a sample of mammalian somatic cells obtained from a donor having a disease or condition or genetically predisposed to a disease or condition;
    (b) obtaining criteria from a customer for selection of an iPSC based on one or more of of the diseases or conditions suffered by donor or for which the donor is genetically predisposed;
    (c) searching a database comprising sample information for each of the plurality of different iPSCs in an iPSC bank, said different iPSCs having genetic material from different donors, said sample information comprising one or more of said criteria;
    (d) identifying suitable iPSCs matching the criteria from the customer in said iPSC bank; and
    (e) differentiating a part of the iPSCs stocked in step (a) and identified in step (d) to produce the mammalian iPSC-derived differentiated cells; and
    (f) providing the mammalian iPSC-derived differentiated cells to the customer.

2. The method of claim 1, further comprising a step of selecting a desired subpopulation of iPSCs-derived differentiated cells obtained in step (e); wherein the desired subpopulation is identified by one or more of: a monoclonal antibody specific to a desired cell type, expression of a reporter gene in a cell type specific manner, negative selection of proliferating cells with the herpes simplex virus thymidine kinase/ganciclovir suicide gene system, and positive selection of cells expressing a bicistronic reporter.

3. The method of claim 1, wherein the iPSCs are differentiated to produce one or more cell types selected from the group consisting of: neural stem cells, cardiac stem cells, hepatic stem cells, hematopoietic stem cells, ectodermal cells, mesodermal cells, endodermal cells, neurons, oligodendrocytes, astrocytes, motor neurons, fibroblasts, cardiomyocytes, pancreatic progenitor cells, pancreatic beta cells, hepatocytes, myocytes, dopaminergic neurons, adipocytes, chondrocytes, smooth muscle cells, keratinocytes, macrophages, mast cells, melanocytes, osteoblasts, skeletal muscle cells, retinal cells, glial progenitor cells, glial cells, lung progenitor cells and white blood cells.

4. The method of claim 1, wherein the disease or condition is selected from the group consisting of: a neurodegenerative disorder, a neurological disorder, an eye disease, a mood disorder, a respiratory disease, an auditory disease, a cardiovascular disease, an immunological disorder, a hematological disease, a metabolic disorder, a kidney disease, a proliferative disorder, a genetic disorder, an autoimmune disease, a drug sensitivity condition, a cognitive impairment, depression, deafness, osteoporosis, diabetes, macular degeneration, obesity, Alexander's disease, Alper's disease, Alzheimer's disease, amyotrophic lateral sclerosis, ataxia telangiectasia, Batten disease, Canavan disease, Cockayne syndrome, corticobasal degeneration, Creutzfeldt-Jakob disease, Huntington's disease, HIV-associated dementia, Kennedy's disease, Krabbe's disease, lewy body dementia, Machado-Joseph disease, multiple sclerosis, multiple system atrophy, narcolepsy, neuroborreliosis, Parkinson's disease, Pelizaeus-Merzbacher Disease, Pick's disease, primary lateral sclerosis, a prion disease, Refsum's disease, Sandhoffs disease, Schilder's disease, subacute combined degeneration of spinal cord secondary to pernicious anaemia, schizophrenia, spinocerebellar ataxia, spinal muscular atrophy (SMA), Steele-Richardson-Olszewski disease, tabes dorsalis, acquired immune deficiency, leukemia, lymphoma, a hypersensitivity (allergy), severe combined immune deficiency, acute disseminated encephalomyelitis, addison's disease, ankylosing spondylitis, antiphospholipid antibody syndrome, autoimmune hemolytic anemia, autoimmune hepatitis, bullous pemphigoid, coeliac disease, dermatomyositis, diabetes mellitus type 1, diabetes mellitus type 2, Goodpasture's syndrome, Graves' disease, Guillain-Barre syndrome, Hashimoto's disease, idiopathic thrombocytopenic purpura, lupus erythematosus, myasthenia gravis, pemphigus, pernicious anaemia, polymyositis, primary biliary cirrhosis, rheumatoid arthritis, Sjogren's syndrome, temporal arthritis, vasculitis, Wegener's granulomatosis, aneurysm, angina, arrhythmia, atherosclerosis, cardiomyopathy, calcific aortic valve disease (CAVD), cerebrovascular accident (stroke), cerebrovascular disease, congenital heart disease, congestive heart failure, myocarditis, valve disease coronary, cardiomyopathy, diastolic dysfunction, endocarditis, hypertension, hypertrophic cardiomyopathy, mitral valve prolapse, myocardial infarction, venous thromboembolism, acid lipase disease, amyloidosis, Barth Syndrome, biotinidase deficiency, carnitine palmitoyl transferase deficiency type II, central pontine myelinolysis, muscular dystrophy, Farber's Disease, glucose-6-phosphate dehydrogenase deficiency, gangliosidoses, trimethylaminuria, Lesch-Nyhan syndrome, lipid storage diseases, metabolic myopathies, methylmalonic aciduria, mitochondrial myopathies, mucopolysaccharidoses, mucolipidoses, mucolipidoses, mucopolysaccharidoses, multiple CoA carboxylase deficiency, nonketotic hyperglycinemia, Pompe disease, propionic acidemia, type I glycogen storage disease, urea cycle disorders, hyperoxaluria, oxalosis, carcinoma, sarcoma, germ cell tumors, blastic tumors, prostate cancer, lung cancer, colorectal cancer, bladder cancer, cutaneous melanoma, breast cancer, endometrial cancer, and ovarian cancer.

* * * * *